(12) United States Patent
Masumoto et al.

(10) Patent No.: US 8,680,328 B2
(45) Date of Patent: Mar. 25, 2014

(54) METHOD FOR PRODUCING OPTICALLY ACTIVE CYCLOPROPANE CARBOXYLIC ACID ESTER COMPOUND, ASYMMETRIC COPPER COMPLEX, AND OPTICALLY ACTIVE SALICYLIDENEAMINOALCOHOL COMPOUND

(75) Inventors: Katsuhisa Masumoto, Ibaraki (JP); Kouji Yoshikawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 18 days.

(21) Appl. No.: 13/062,288

(22) PCT Filed: Sep. 7, 2009

(86) PCT No.: PCT/JP2009/065973
§ 371 (c)(1),
(2), (4) Date: Mar. 4, 2011

(87) PCT Pub. No.: WO2010/030017
PCT Pub. Date: Mar. 18, 2010

(65) Prior Publication Data
US 2011/0166372 A1 Jul. 7, 2011

(30) Foreign Application Priority Data
Sep. 10, 2008 (JP) .................................. 2008-231921

(51) Int. Cl.
*C07C 61/04* (2006.01)

(52) U.S. Cl.
USPC ....................................................... 562/506

(58) Field of Classification Search
None
See application file for complete search history.

(56) References Cited

U.S. PATENT DOCUMENTS

| | | | |
|---|---|---|---|
| 7,705,165 | B2 | 4/2010 | Itagaki et al. |
| 7,928,253 | B2 * | 4/2011 | Hirata et al. ................. 549/462 |
| 2002/0177718 | A1 | 11/2002 | Yamamoto et al. |
| 2006/0211879 | A1 | 9/2006 | Itagaki |
| 2008/0275268 | A1 | 11/2008 | Masumoto et al. |
| 2009/0048450 | A1 | 2/2009 | Itagaki |
| 2010/0168463 | A1 | 7/2010 | Hirata et al. |

FOREIGN PATENT DOCUMENTS

| | | | |
|---|---|---|---|
| JP | 2003-12675 | A | 1/2003 |
| JP | 2007-308473 | A | 1/2003 |
| JP | 2004-51499 | A | 2/2004 |
| JP | 2004051499 | * | 2/2004 |
| JP | 2006-45194 | A | 2/2006 |

OTHER PUBLICATIONS

Li et al., Tetrahedron: Asymmetry (2000), 11(5), 1157-1163.*
Li et al., Journal of Molecular Catalysis A: Chemical (2001), 165(1-2), 67-71.*

(Continued)

Primary Examiner — Karl J Puttlitz
(74) Attorney, Agent, or Firm — Birch, Stewart, Kolasch & Birch, LLP

(57) ABSTRACT

A process for producing an optically active cyclopropanecarboxylic acid ester compound represented by the formula (4):

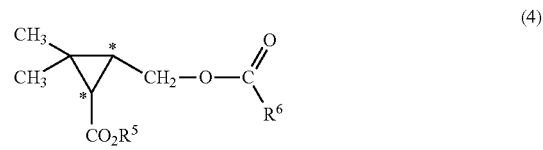

(wherein $R^5$, $R^6$ and * each represents the same meaning as defined below), comprising reacting a diazoacetic acid ester represented by the formula (2):

$$N_2CHCO_2R^5 \quad (2)$$

(wherein $R^5$ represents an alkyl group having 1 to 15 carbon atoms or the like) with a compound represented by the formula (3):

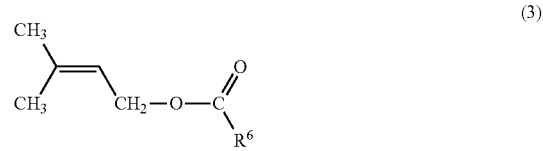

(wherein $R^6$ represents an alkyl group having 1 to 15 carbon atoms or the like), in the presence of an asymmetric copper complex obtained by reacting a copper compound and an optically active salicylideneaminoalcohol compound represented by the formula (1):

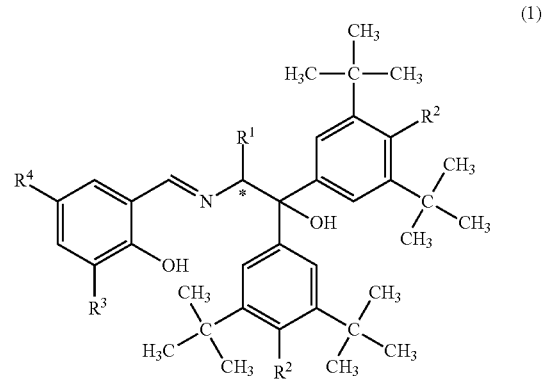

(wherein $R^1$ represents an alkyl group having 1 to 4 carbon atoms or the like, $R^2$ represents a hydrogen atom or the like, $R^3$ and $R^4$ independently represent a hydrogen atom or the like, and * represents an asymmetric center).

11 Claims, No Drawings

(56) References Cited

OTHER PUBLICATIONS

International Preliminary Report on Patentability and the Written Opinion of the International Searching Authority dated Apr. 19, 2011, for Application No. PCT/JP2009/065973.
Li et al., "Asymmetric cyclopropanation catalyzed by copper-Schiff's base complexes", Journal of Molecular Catalysis A: Chemical 165, 2001, pp. 67-71.
Li et al., "Highly efficient and enantioselective cyclopropanation of styrene with diazoacetates using a new copper-(Schiff-base) catalyst", Tetrahedron: Asymmetry, vol. 11, 2000. pp. 1157-1163.
Russo et al., "Asymmetric Epoxidation of trans-Chalcones Organocatalyzed by •-Amino Alcohols", Eur. J. Org. Chem., 2008, pp. 2767-2773.
Lebel et al., "Stereoselective Cyclopropanation Reactions," Chem. Rev., vol. 103, No. 4, 2003, pp. 977-1050.

* cited by examiner

METHOD FOR PRODUCING OPTICALLY ACTIVE CYCLOPROPANE CARBOXYLIC ACID ESTER COMPOUND, ASYMMETRIC COPPER COMPLEX, AND OPTICALLY ACTIVE SALICYLIDENEAMINOALCOHOL COMPOUND

TECHNICAL FIELD

The present invention relates to a process for producing an optically active cyclopropanecarboxylic acid ester compound, and an asymmetric copper complex and an optically active salicylideneaminoalcohol compound.

BACKGROUND ART

In an optically active cyclopropanecarboxylic acid ester compound represented by the formula (4):

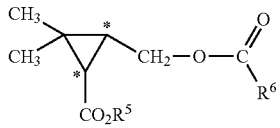
(4)

(wherein $R^5$ represents an alkyl group having 1 to 15 carbon atoms or an aryl group having 6 to 10 carbon atoms, $R^6$ represents an alkyl group having 1 to 15 carbon atoms, an aryl group having 6 to 10 carbon atoms or an aralkyl group having 7 to 20 carbon atoms, and * represents an asymmetric center), a cis form in which a group represented by —$CO_2R^5$ and a group represented by $R^6COOCH_2$— are on the same side relative to a cyclopropane ring plane, and a trans form in which those groups are on opposite sides are present, and these forms are useful as an intermediate for synthesizing medicaments and agrochemicals such as pyrethroid compounds.

JP-A No. 2004-51499 discloses a process for producing such an optically active cyclopropanecarboxylic acid ester compound by reacting a diazoacetic acid ester represented by the formula (2):

(2)

(wherein $R^5$ represents the same meaning as defined above) with a compound represented by the formula (3):

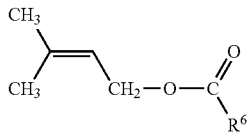
(3)

[wherein $R^6$ represents the same meaning as defined above] in the presence of an asymmetric copper complex obtained by reacting a copper compound and an optically active salicylideneaminoalcohol compound.

DISCLOSURE OF THE INVENTION

The present invention provides:
<1> A process for producing an optically active cyclopropanecarboxylic acid ester compound represented by the formula (4):

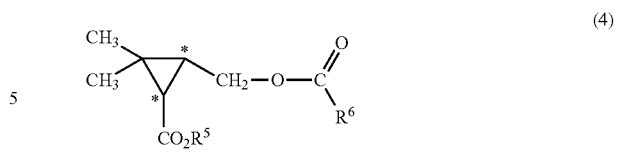
(4)

(wherein $R^5$, $R^6$ and * each represents the same meaning as defined below), comprising reacting a diazoacetic acid ester represented by the formula (2):

(2)

(wherein $R^5$ represents an alkyl group having 1 to 15 carbon atoms or an aryl group having 6 to 10 carbon atoms) with a compound represented by the formula (3):

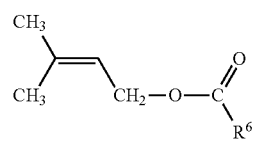
(3)

(wherein $R^6$ represents an alkyl group having 1 to 15 carbon atoms, an aryl group having 6 to 10 carbon atoms or an aralkyl group having 7 to 20 carbon atoms), in the presence of an asymmetric copper complex obtained by reacting a copper compound and an optically active salicylideneaminoalcohol compound represented by the formula (1):

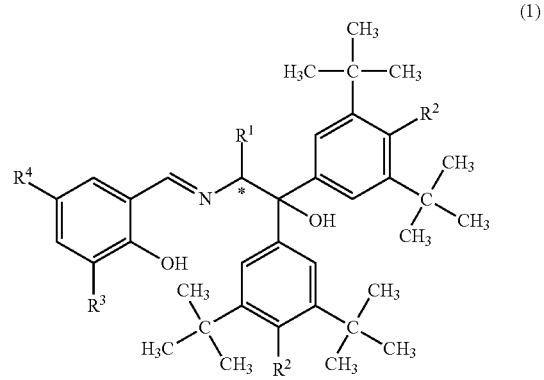
(1)

(wherein $R^1$ represents an alkyl group having 1 to 4 carbon atoms, an aryl group having 6 to 10 carbon atoms or an aralkyl group having 7 to 20 carbon atoms, $R^2$ represents a hydrogen atom, an alkyl group having 1 to 4 carbon atoms or an alkoxy group having 1 to 10 carbon atoms, $R^3$ and $R^4$ independently represent a hydrogen atom or an electron withdrawing group, and * represents an asymmetric center).
<2> The production process according to <1>, wherein the copper compound is a divalent copper compound.
<3> The production process according to <1>, wherein the copper compound is copper acetate.
<4> The production process according to any one of <1> to <3>, wherein $R^4$ is a nitro group.
<5> The production process according to any one of <1> to <4>, wherein $R^2$ is a hydrogen atom.
<6> The production process according to any one of <1> to <5>, wherein $R^5$ is an ethyl group, and $R^6$ is a methyl group.

<7> The production process according to any one of <1> to <6>, wherein the reaction of the diazoacetic acid ester represented by the formula (2) with the compound represented by the formula (3) is performed in the presence of a Lewis acid.
<8> The production process according to <7>, wherein the Lewis acid is a metal alkoxide having Lewis acidity.
<9> The production process according to any one of <1> to <8>, wherein the reaction of the diazoacetic acid ester represented by the formula (2) with the compound represented by the formula (3) is performed in the presence of a lithium compound.
<10> The production process according to <9>, wherein the lithium compound is a lithium alkoxide having 1 to 4 carbon atoms.
<11> An asymmetric copper compound obtained by reacting a copper compound and an optically active salicylideneaminoalcohol compound represented by the formula (1):

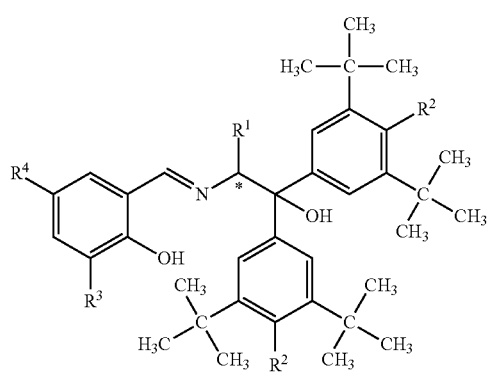

(wherein $R^1$ is an alkyl group having 2 to 4 carbon atoms, an aryl group having 6 to 10 carbon atoms or an aralkyl group having 7 to 20 carbon atoms, $R^2$ is a hydrogen atom, an alkyl group having 1 to 4 carbon atoms or an alkoxy group having 1 to 10 carbon atoms, $R^3$ and $R^4$ independently represent a hydrogen atom or an electron withdrawing group, and * represents an asymmetric center).
<12> An optically active salicylideneaminoalcohol compound represented by the formula (1):

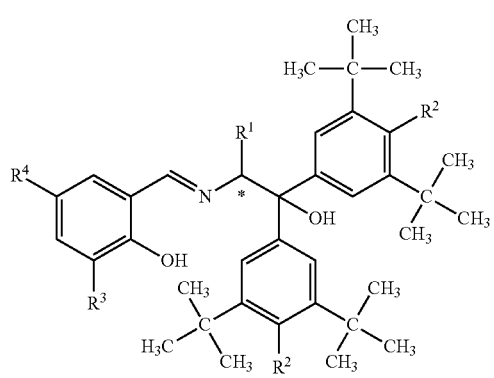

(wherein $R^1$ is an alkyl group having 2 to 4 carbon atoms, an aryl group having 6 to 10 carbon atoms, or an aralkyl group having 7 to 20 carbon atoms, $R^2$ is a hydrogen atom, an alkyl group having 1 to 4 carbon atoms or an alkoxy group having 1 to 10 carbon atoms, $R^3$ and $R^4$ independently represent a hydrogen atom or an electron withdrawing group, and * represents an asymmetric center).
<13> A mixture of a cis form and a trans form of an optically active cyclopropanecarboxylic acid ester compound represented by the formula (4):

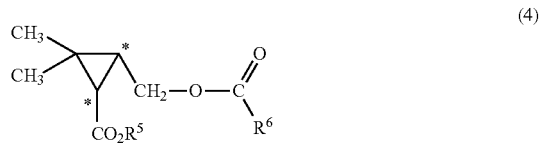

(wherein $R^5$ represents an alkyl group having 1 to 15 carbon atoms or an aryl group having 6 to 10 carbon atoms, $R^6$ represents an alkyl group having 1 to 15 carbon atoms, an aryl group having 6 to 10 carbon atoms or an aralkyl group having 7 to 20 carbon atoms, and * represents an asymmetric center), wherein a ratio of the cis form relative to the total of the cis form and the trans form is 80% or more.

BEST MODE FOR CARRYING OUT THE INVENTION

First, the asymmetric copper complex obtained by reacting a copper compound with an optically active salicylideneaminoalcohol compound represented by the formula (1):

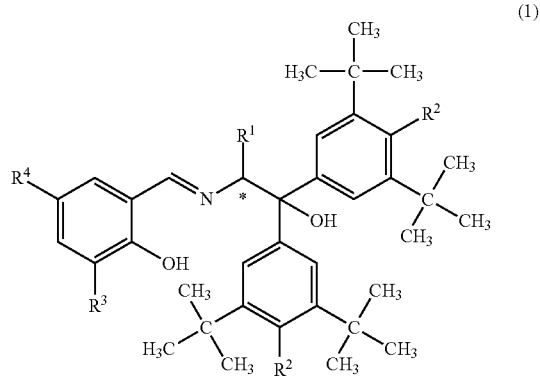

(hereinafter, abbreviated as optically active salicylideneaminoalcohol (1)) will be described.

The copper compound may be a monovalent copper compound, or may be a divalent copper compound. The divalent copper compound is preferable. Examples of the copper compound include copper organic carboxylate having 2 to 15 carbon atoms such as copper (I) acetate, copper (II) acetate, copper (II) naphthenate or copper (II) 2-ethylhexanoate, copper haloalkanesulfonate having 1 to 4 carbon atoms such as copper (I) trifluoromethanesulfonate or copper (II) trifluoromethanesulfonate, halogenated copper such as copper (I) chloride, copper (II) chloride, copper (I) bromide or copper (II) bromide, copper (I) nitrate, copper (II) nitrate, copper (II) carbonate and copper (II) hydroxide. The copper organic carboxylate having 2 to 15 carbon atoms is preferable, and copper (II) acetate is more preferable. Such copper compounds may be used alone, or two or more kinds thereof may be used by mixing them. The copper compound may be an anhydride, or a hydrate. As such a copper compound, a commercially available copper compound may be used, or a copper compound prepared according to a known method may be used.

In the formula (1), R¹ represents an alkyl group having 1 to 4 carbon atoms, an aryl group having 6 to 10 carbon atoms or an aralkyl group having 7 to 20 carbon atoms, and an alkyl group having 2 to 4 carbon atoms, an aryl group having 6 to 10 carbon atoms or an aralkyl group having 7 to 20 carbon atoms is preferable.

Examples of the alkyl group having 1 to 4 carbon atoms include a methyl group, an ethyl group, a n-propyl group, an isopropyl group, a n-butyl group, an isobutyl group, a sec-butyl group and a tert-butyl group. Examples of the aryl group having 6 to 10 carbon atoms include a phenyl group and a naphthyl group. Examples of the aralkyl group having 7 to 20 carbon atoms include a group constituted by the alkyl group having 1 to 4 carbon atoms and the aryl group having 6 to 10 carbon atoms such as a benzyl group or a trityl group. It is more preferable that R¹ is an alkyl group having 2 to 4 carbon atoms, a phenyl group or a benzyl group.

In the formula (1), R² represents a hydrogen atom, an alkyl group having 1 to 4 carbon atoms or an alkoxy group having 1 to 10 carbon atoms. Examples of the alkyl group having 1 to 4 carbon atoms include a methyl group, an ethyl group, a n-propyl group, a n-butyl group and an isobutyl group. Examples of the alkoxy group having 1 to 10 carbon atoms include a methoxy group, an ethoxy group, a n-propoxy group, a n-butoxy group, a n-pentyloxy group, a n-hexyloxy group, a n-octyloxy group, an isooctyloxy group and a n-decyloxy group, and an alkoxy group having 1 to 4 carbon atoms is preferable. R² is preferably a hydrogen atom or an alkoxy group having 1 to 4 carbon atoms, more preferably a hydrogen atom.

In the formula (1), R³ and R⁴ independently represent a hydrogen atom or an electron withdrawing group. Examples of the electron withdrawing group include a nitro group; a halogen atom such as a fluorine atom, a chlorine atom, a bromine atom or an iodine atom; an alkoxycarbonyl group having 2 to 10 carbon atoms such as a methoxycarbonyl group or an ethoxycarbonyl group; a perfluoroalkyl group having 1 to 6 carbon atoms such as a trifluoromethyl group or a heptafluoropropyl group; a cyano group; and an alkanesulfonyl group having 1 to 6 carbon atoms which optionally have a fluorine atom, such as a methanesulfonyl group or a trifluoromethanesulfonyl group. It is preferable that R³ is a hydrogen atom, a nitro group or a halogen atom. R⁴ is preferably an electron withdrawing group, more preferably a nitro group, a fluorine atom or an alkoxycarbonyl group having 2 to 5 carbon atoms, particularly preferably a nitro group.

In the formula (1), * represents an asymmetric center,

As the optically active salicylideneaminoalcohol (1), an optically active salicylideneaminoalcohol (1) in which R¹ is an alkyl group having 1 to 4 carbon atoms, R² is a hydrogen atom, R³ is a hydrogen atom, and R⁴ is a nitro group, an optically active salicylideneaminoalcohol (1) in which R¹ is an alkyl group having 1 to 4 carbon atoms, R² is an alkoxy group having 1 to 4 carbon atoms, R³ is a hydrogen atom, and R⁴ is a nitro group,
an optically active salicylideneaminoalcohol (1) in which R¹ is an alkyl group having 1 to 4 carbon atoms, R² is a hydrogen atom, R³ is a nitro group, and R⁴ is a hydrogen atom, an optically active salicylideneaminoalcohol (1) in which R¹ is an alkyl group having 1 to 4 carbon atoms, R² is a hydrogen atom, R³ is a nitro group, and R⁴ is a nitro group, an optically active salicylideneaminoalcohol (1) in which R¹ is an alkyl group having 1 to 4 carbon atoms, R² is a hydrogen atom, R³ is a halogen atom, and R⁴ is a hydrogen atom, an optically active salicylideneaminoalcohol (1) in which R¹ is an alkyl group having 1 to 4 carbon atoms, R² is a hydrogen atom, R³ is a halogen atom, and R⁴ is a nitro group, an optically active salicylideneaminoalcohol (1) in which R¹ is an alkyl group having 1 to 4 carbon atoms, R² is a hydrogen atom, R³ is a halogen atom, and R⁴ is a halogen group, an optically active salicylideneaminoalcohol (1) in which R¹ is an alkyl group having 1 to 4 carbon atoms, R² is a hydrogen atom, R³ is a hydrogen atom and R⁴ is an alkoxycarbonyl group having 2 to 5 carbon atoms,
an optically active salicylideneaminoalcohol (1) in which R¹ is a benzyl group, R² is a hydrogen atom, R³ is a hydrogen atom, and R⁴ is a nitro group,
an optically active salicylideneaminoalcohol (1) in which R¹ is a benzyl group, R² is a hydrogen atom, R³ is a nitro group, and R⁴ is a nitro group,
an optically active salicylideneaminoalcohol (1) in which R¹ is a phenyl group, R² is a hydrogen atom, R³ is a hydrogen atom, and R⁴ is a nitro group, and
an optically active salicylideneaminoalcohol (1) in which R¹ is a phenyl group, R² is a hydrogen atom, R³ is a nitro group, and R⁴ is a nitro group,
are preferable.

Examples of such an optically active salicylideneaminoalcohol (1) include:
optically active N-(5-nitrosalicylidene)-2-amino-1,1-di(3,5-di-tert-butylphenyl)-1-propanol, optically active
N-(5-nitrosalicylidene)-2-amino-1,1-di(3,5-di-tert-butylphenyl)-3-phenyl-1-propanol, optically active
N-(5-nitrosalicylidene)-2-amino-1,1-di(3,5-di-tert-butylphenyl)-1-butanol, optically active
N-(5-nitrosalicylidene)-2-amino-1,1-di(3,5-di-tert-butylphenyl)-3-methyl-1-butanol, optically active
N-(5-nitrosalicylidene)-2-amino-1,1-di(3,5-di-tert-butylphenyl)-4-methyl-1-pentanol, optically active
N-(5-nitrosalicylidene)-2-amino-1,1-di(3,5-di-tert-butylphenyl)-3-methyl-1-pentanol,
optically active
N-(3-nitrosalicylidene)-2-amino-1,1-di(3,5-di-tert-butylphenyl)-1-propanol, optically active
N-(3-nitrosalicylidene)-2-amino-1,1-di(3,5-di-tert-butylphenyl)-3-phenyl-1-propanol, optically active
N-(3-nitrosalicylidene)-2-amino-1,1-di(3,5-di-tert-butyphenyl)-1-butanol, optically active
N-(3-nitrosalicylidene)-2-amino-1,1-di(3,5-di-tert-butyphenyl)-3-methyl-1-butanol, optically active
N-(3-nitrosalicylidene)-2-amino-1,1-di(3,5-di-tert-butyphenyl)-4-methyl-1-pentanol, optically active
N-(3-nitrosalicylidene)-2-amino-1,1-di(3,5-di-tert-butylphenyl)-3-methyl-1-pentanol,
optically active
N-(3-bromo-5-nitrosalicylidene)-2-amino-1,1-di(3,5-di-tert-butylphenyl)-1-propanol, optically active
N-(3-bromo-5-nitrosalicylidene)-2-amino-1,1-di(3,5-di-tert-butylphenyl)-3-phenyl-1-propanol, optically active
N-(3-bromo-5-nitrosalicylidene)-2-amino-1,1-di(3,5-di-tert-butylphenyl)-1-butanol, optically active
N-(3-bromo-5-nitrosalicylidene)-2-amino-1,1-di(3,5-di-tert-butylphenyl)-3-methyl-1-butanol, optically active
N-(3-bromo-5-nitrosalicylidene)-2-amino-1,1-di(3,5-di-tert-butylphenyl)-4-methyl-1-pentanol, optically active
N-(3-bromo-5-nitrosalicylidene)-2-amino-1,1-di(3,5-di-tert-butylphenyl)-3-methyl-1-pentanol,
optically active
N-(3,5-dinitrosalicylidene)-2-amino-1,1-di(3,5-di-tert-butylphenyl)-1-propanol, optically active
N-(3,5-dinitrosalicylidene)-2-amino-1,1-di(3,5-di-tert-butylphenyl)-3-phenyl-1-propanol, optically active N-(3,5-dinitrosalicylidene)-2-amino-1,1-di(3,5-di-tert-butylphenyl)-1-butanol, optically active
N-(3,5-dinitrosalicylidene)-2-amino-1,1-di(3,5-di-tert-butylphenyl)-3-methyl-1-butanol, optically active
N-(3,5-dinitrosalicylidene)-2-amino-1,1-di(3,5-di-tert-butylphenyl)-4-methyl-1-pentanol, optically active
N-(3,5-dinitrosalicylidene)-2-amino-1,1-di(3,5-di-tert-butylphenyl)-3-methyl-1-pentanol, optically active
N-(3-fluorosalicylidene)-2-amino-1,1-di(3,5-di-tert-butylphenyl)-1-propanol, optically active
N-(3-fluorosalicylidene)-2-amino-1,1-di(3,5-di-tert-butylphenyl)-3-phenyl-1-propanol, optically active
N-(3-fluorosalicylidene)-2-amino-1,1-di(3,5-di-tert-butylphenyl)-1-butanol, optically active
N-(3-fluorosalicylidene)-2-amino-1,1-di(3,5-di-tert-butylphenyl)-3-methyl-1-butanol, optically active
N-(3-fluorosalicylidene)-2-amino-1,1-di(3,5-di-tert-butylphenyl)-4-methyl-1-pentanol, optically active
N-(3-fluorosalicylidene)-2-amino-1,1-di(3,5-di-tert-butylphenyl)-3-methyl-1-pentanol, optically active
N-(5-fluorosalicylidene)-2-amino-1,1-di(3,5-di-tert-butylphenyl)-1-propanol, optically active
N-(5-fluorosalicylidene)-2-amino-1,1-di(3,5-di-tert-butylphenyl)-3-phenyl-1-propanol, optically active
N-(5-fluorosalicylidene)-2-amino-1,1-di(3,5-di-tert-butylphenyl)-1-butanol, optically active
N-(5-fluorosalicylidene)-2-amino-1,1-di(3,5-di-tert-butylphenyl)-3-methyl-1-butanol, optically active
N-(5-fluorosalicylidene)-2-amino-1,1-di(3,5-di-tert-butylphenyl)-4-methyl-1-pentanol, optically active
N-(5-fluorosalicylidene)-2-amino-1,1-di(3,5-di-tert-butylphenyl)-3-methyl-1-pentanol, optically active
N-(3,5-difluorosalicylidene)-2-amino-1,1-di(3,5-di-terylphenyl)-1-propanol, optically active
N-(3,5-difluorosalicylidene)-2-amino-1,1-di(3,5-di-tert-butylphenyl)-3-phenyl-1-propanol, optically active
N-(3,5-difluorosalicylidene)-2-amino-1,1-di(3,5-di-tert-butylphenyl)-1-butanol, optically active
N-(3,5-difluorosalicylidene)-2-amino-1,1-di(3,5-di-tert-butylphenyl)-3-methyl-1-butanol, optically active
N-(3,5-difluorosalicylidene)-2-amino-1,1-di(3,5-di-tert-butylphenyl)-4-methyl-1-pentanol, optically active
N-(3,5-difluorosalicylidene)-2-amino-1,1-di(3,5-di-tert-butylphenyl)-3-methyl-1-pentanol, optically active
N-[5-(methoxycarbonyl)salicylidene]-2-amino-1,1-di(3,5-di-tert-butylphenyl)-1-propanol, optically active
N-[5-(methoxycarbonyl)salicylidene]-2-amino-1,1-di(3,5-di-tert-butylphenyl)-3-phenyl-1-propanol, optically active
N-[5-(methoxycarbonyl)salicylidene]-2-amino-1,1-di(3,5-di-tert-butylphenyl)-1-butanol, optically active
N-[5-(methoxycarbonyl)salicylidene]-2-amino-1,1-di(3,5-di-tert-butylphenyl)-3-methyl-1-butanol, optically active
N-[5-(methoxycarbonyl)salicylidene]-2-amino-1,1-di(3,5-di-tert-butylphenyl)-4-methyl-1-pentanol, optically active
N-[5-(methoxycarbonyl)salicylidene]-2-amino-1,1-di(3,5-di-tert-butylphenyl)-3-methyl-1-pentanol, optically active
N-(5-trifluoromethylsalicylidene)-2-amino-1,1-di(3,5-di-tert-butylphenyl)-1-propanol, optically active
N-(5-trifluoromethylsaylcylidene)-2-amino-1,1-di(3,5-di-tert-butylphenyl)-3-phenyl-1-propanol, optically active
N-(5-trifluoromethylsalicylidene)-2-amino-1,1-di(3,5-di-tert-butylphenyl)-1-butanol, optically active
N-(5-trifluoromethylsalicylidene)-2-amino-1,1-di(3,5-di-tert-butylphenyl)-3-methyl-1-butanol, optically active
N-(5-trifluoromethylsalicylidene)-2-amino-1,1-di(3,5-di-tert-butylphenyl)-4-methyl-1-pentanol, optically active
N-(5-trifluoromethylsalicylidene)-2-amino-1,1-di(3,5-di-tert-butylphenyl)-3-methyl-1-pentanol, optically active
N-(5-cyanosalicylidene)-2-amino-1,1-di(3,5-di-tert-butyphenyl)-1-propanol, optically active
N-(5-cyanosalicylidene)-2-amino-1,1-di(3,5-di-tert-butyphenyl)-3-phenyl-1-propanol, optically active
N-(5-cyanosalicylidene)-2-amino-1,1-di(3,5-di-tert-butylphenyl)-1-butanol, optically active
N-(5-cyanosalicylidene)-2-amino-1,1-di(3,5-di-tert-butyphenyl)-3-methyl-1-butanol, optically active
N-(5-cyanosalicylidene)-2-amino-1,1-di(3,5-di-tert-butylphenyl)-4-methyl-1-pentanol, optically active
N-(5-cyanosalicylidene)-2-amino-1,1-di(3,5-di-tert-butyphenyl)-3-methyl-1-pentanol, optically active
N-(5-nitrosalicylidene)-2-amino-1,1-di(4-methoxy-3,5-di-tert-butylphenyl)-1-propanol, optically active
N-(5-nitrosalicylidene)-2-amino-1,1-di(4-methoxy-3,5-di-tert-butylphenyl)-3-phenyl-1-propanol, optically active
N-(5-nitrosalicylidene)-2-amino-1,1-di(4-methoxy-3,5-di-tert-butylphenyl)-1-butanol, optically active
N-(5-nitrosalicylidene)-2-amino-1,1-di(4-methoxy-3,5-di-tert-butylphenyl)-3-methyl-1-butanol, optically active
N-(5-nitrosalicylidene)-2-amino-1,1-di(4-methoxy-3,5-di-tert-butylphenyl)-4-methyl-1-pentanol, optically active
N-(5-nitrosalicylidene)-2-amino-1,1-di(4-methoxy-3,5-di-tert-butylphenyl)-3-methyl-1-pentanol, optically active
N-(3-nitrosalicylidene)-2-amino-1,1-di(4-methoxy-3,5-di-tert-butylphenyl)-1-propanol, optically active
N-(3-nitrosalicylidene)-2-amino-1,1-di(4-methoxy-3,5-di-tert-butylphenyl)-3-phenyl-1-propanol, optically active
N-(3-nitrosalicylidene)-2-amino-1,1-di(4-methoxy-3,5-di-tert-butylphenyl)-1-butanol, optically active
N-(3-nitrosalicylidene)-2-amino-1,1-di(4-methoxy-3,5-di-tert-butylphenyl)-3-methyl-1-butanol, optically active
N-(3-nitrosalicylidene)-2-amino-1,1-di(4-methoxy-3,5-di-tert-butylphenyl)-4-methyl-1-pentanol, optically active
N-(3-nitrosalicylidene)-2-amino-1,1-di(4-methoxy-3,5-di-tert-butylphenyl)-3-methyl-1-pentanol, optically active
N-(3-bromo-5-nitrosalicylidene)-2-amino-1,1-di(4-methoxy-3,5-di-tert-butylphenyl)-1-propanol, optically active
N-(3-bromo-5-nitrosalicylidene)-2-amino-1,1-di(4-methoxy-3,5-di-tert-butylphenyl)-3-phenyl-1-propanol, optically active
N-(3-bromo-5-nitrosalicylidene)-2-amino-1,1-di(4-methoxy-3,5-di-tert-butylphenyl)-1-butanol, optically active
N-(3-bromo-5-nitrosalicylidene)-2-amino-1,1-di(4-methoxy-3,5-di-tert-butylphenyl)-3-methyl-1-butanol, optically active
N-(3-bromo-5-nitrosalicylidene)-2-amino-1,1-di(4-methoxy-3,5-di-tert-butylphenyl)-4-methyl-1-pentanol, optically active
N-(3-bromo-5-nitrosalicylidene)-2-amino-1,1-di(4-methoxy-3,5-di-tert-butylphenyl)-3-methyl-1-pentanol, optically active
N-(3,5-dinitrosalicylidene)-2-amino-1,1-di(4-methoxy-3,5-di-tert-butylphenyl)-1-propanol, optically active
N-(3,5-dinitrosalicylidene)-2-amino-1,1-di(4-methoxy-3,5-di-tert-butylphenyl)-3-phenyl-1-propanol, optically active N-(3,5-dinitrosalicylidene)-2-amino-1,1-di(4-methoxy-3,5-di-tert-butylphenyl)-1-butanol, optically active
N-(3,5-dinitrosalicylidene)-2-amino-1,1-di(4-methoxy-3,5-di-tert-butylphenyl)-3-methyl-1-butanol, optically active
N-(3,5-dinitrosalicylidene)-2-amino-1,1-di(4-methoxy-3,5-di-tert-butylphenyl)-4-methyl-1-pentanol, optically active
N-(3,5-dinitrosalicylidene)-2-amino-1,1-di(4-methoxy-3,5-di-tert-butylphenyl)-3-methyl-1-pentanol, optically active
N-(3-fluorosalicylidene)-2-amino-1,1-di(4-methoxy-3,5-di-tert-butylphenyl)-1-propanol, optically active
N-(3-fluorosalicylidene)-2-amino-1,1-di(4-methoxy-3,5-di-tert-butylphenyl)-3-phenyl-1-propanol, optically active
N-(3-fluorosalicylidene)-2-amino-1,1-di(4-methoxy-3,5-di-tert-butylphenyl)-1-butanol, optically active
N-(3-fluorosalicylidene)-2-amino-1,1-di(4-methoxy-3,5-di-tert-butylphenyl)-3-methyl-1-butanol, optically active
N-(3-fluorosalicylidene)-2-amino-1,1-di(4-methoxy-3,5-di-tert-butylphenyl)-4-methyl-1-pentanol, optically active
N-(3-fluorosalicylidene)-2-amino-1,1-di(4-methoxy-3,5-di-tert-butylphenyl)-3-methyl-1-pentanol, optically active
N-(5-fluorosalicylidene)-2-amino-1,1-di(4-methoxy-3,5-di-tert-butylphenyl)-1-propanol, optically active
N-(5-fluorosalicylidene)-2-amino-1,1-di(4-methoxy-3,5-di-tert-butylphenyl)-3-phenyl-1-propanol, optically active
N-(5-fluorosalicylidene)-2-amino-1,1-di(4-methoxy-3,5-di-tert-butylphenyl)-1-butanol, optically active
N-(5-fluorosalicylidene)-2-amino-1,1-di(4-methoxy-3,5-di-tert-butylphenyl)-3-methyl-1-butanol, optically active
N-(5-fluorosalicylidene)-2-amino-1,1-di(4-methoxy-3,5-di-tert-butylphenyl)-4-methyl-1-pentanol, optically active
N-(5-fluorosalicylidene)-2-amino-1,1-di(4-methoxy-3,5-di-tert-butylphenyl)-3-methyl-1-pentanol, optically active
N-(3,5-difluorosalicylidene)-2-amino-1,1-di(4-methoxy-3,5-di-tert-butylphenyl)-1-propanol, optically active
N-(3,5-difluorosalicylidene)-2-amino-1,1-di(4-methoxy-3,5-di-tert-butylphenyl)-3-phenyl-1-propanol, optically active
N-(3,5-difluorosalicylidene)-2-amino-1,1-di(4-methoxy-3,5-di-tert-butylphenyl)-1-butanol, optically active
N-(3,5-difluorosalicylidene)-2-amino-1,1-di(4-methoxy-3,5-di-tert-butylphenyl)-3-methyl-1-butanol, optically active
N-(3,5-difluorosalicylidene)-2-amino-1,1-di(4-methoxy-3,5-di-tert-butylphenyl)-4-methyl-1-pentanol, optically active
N-(3,5-difluorosalicylidene)-2-amino-1,1-di(4-methoxy-3,5-di-tert-butylphenyl)-3-methyl-1-pentanol, optically active
N-[5-(methoxycarbonyl)salicylidene]-2-amino-1,1-di(4-methoxy-3,5-di-tert-butylphenyl)-1-propanol, optically active
N-[5-(methoxycarbonyl)salicylidene]-2-amino-1,1-di(4-methoxy-3,5-di-tert-butylphenyl)-3-phenyl-1-propanol, optically active
N-[5-(methoxycarbonyl)salicylidene]-2-amino-1,1-di(4-methoxy-3,5-di-tert-butylphenyl)-1-butanol, optically active
N-[5-(methoxycarbonyl)salicylidene]-2-amino-1,1-di(4-methoxy-3,5-di-tert-butylphenyl)-3-methyl-1-butanol, optically active
N-[5-(methoxycarbonyl)salicylidene]-2-amino-1,1-di(4-methoxy-3,5-di-tert-butylphenyl)-4-methyl-1-pentanol, optically active
N-[5-(methoxycarbonyl)salicylidene]-2-amino-1,1-di(4-methoxy-3,5-di-tert-butylphenyl)-3-methyl-1-pentanol, optically active
N-(5-trifluoromethylsalicylidene)-2-amino-1,1-di(4-methoxy-3,5-di-tert-butylphenyl)-1-propanol, optically active
N-(5-trifluoromethylsalicylidene)-2-amino-1,1-di(4-methoxy-3,5-di-tert-butylphenyl)-3-phenyl-1-propanol, optically active
N-(5-trifluoromethylsalicylidene)-2-amino-1,1-di(4-methoxy-3,5-di-tert-butylphenyl)-1-butanol, optically active
N-(5-trifluoromethylsalicylidene)-2-amino-1,1-di(4-methoxy-3,5-di-tert-butylphenyl)-3-methyl-1-butanol, optically active
N-(5-trifluoromethylsalicylidene)-2-amino-1,1-di(4-methoxy-3,5-di-tert-butylphenyl)-4-methyl-1-pentanol, optically active
N-(5-trifluoromethylsalicylidene)-2-amino-1,1-di(4-methoxy-3,5-di-tert-butylphenyl)-3-methyl-1-pentanol, optically active
N-(5-cyanosalicylidene)-2-amino-1,1-di(4-methoxy-3,5-di-tert-butylphenyl)-1-propanol, optically active
N-(5-cyanosalicylidene)-2-amino-1,1-di(4-methoxy-3,5-di-tert-butylphenyl)-3-phenyl-1-propanol, optically active
N-(5-cyanosalicylidene)-2-amino-1,1-di(4-methoxy-3,5-di-tert-butylphenyl)-1-butanol, optically active
N-(5-cyanosalicylidene)-2-amino-1,1-di(4-methoxy-3,5-di-tert-butylphenyl)-3-methyl-1-butanol, optically active
N-(5-cyanosalicylidene)-2-amino-1,1-di(4-methoxy-3,5-di-tert-butylphenyl)-4-methyl-1-pentanol, optically active
N-(5-cyanosalicylidene)-2-amino-1,1-di(4-methoxy-3,5-di-tert-butylphenyl)-3-methyl-1-pentanol, optically active
N-(5-nitrosalicylidene)-2-amino-1,1-di(4-n-butoxy-3,5-di-tert-butylphenyl)-1-propanol, optically active
N-(5-nitrosalicylidene)-2-amino-1,1-di(4-n-butoxy-3,5-di-tert-butylphenyl)-3-phenyl-1-propanol, optically active
N-(5-nitrosalicylidene)-2-amino-1,1-di(4-n-butoxy-3,5-di-tert-butylphenyl)-1-butanol, optically active
N-(5-nitrosalicylidene)-2-amino-1,1-di(4-n-butoxy-3,5-di-tert-butylphenyl)-3-methyl-1-butanol, optically active
N-(5-nitrosalicylidene)-2-amino-1,1-di(4-n-butoxy-3,5-di-tert-butylphenyl)-4-methyl-1-pentanol, optically active
N-(5-nitrosalicylidene)-2-amino-1,1-di(4-n-butoxy-3,5-di-tert-butylphenyl)-3-methyl-1-pentanol, optically active
N-(3-nitrosalicylidene)-2-amino-1,1-di(4-n-butoxy-3,5-di-tert-butylphenyl)-1-propanol, optically active
N-(3-nitrosalicylidene)-2-amino-1,1-di(4-n-butoxy-3,5-di-tert-butylphenyl)-3-phenyl-1-propanol, optically active
N-(3-nitrosalicylidene)-2-amino-1,1-di(4-n-butoxy-3,5-di-tert-butylphenyl)-1-butanol, optically active
N-(3-nitrosalicylidene)-2-amino-1,1-di(4-n-butoxy-3,5-di-tert-butylphenyl)-3-methyl-1-butanol, optically active
N-(3-nitrosalicylidene)-2-amino-1,1-di(4-n-butoxy-3,5-di-tert-butylphenyl)-4-methyl-1-pentanol, optically active
N-(3-nitrosalicylidene)-2-amino-1,1-di(4-n-butoxy-3,5-di-tert-butylphenyl)-3-methyl-1-pentanol, optically active
N-(3-bromo-5-nitrosalicylidene)-2-amino-1,1-di(4-n-butoxy-3,5-di-tert-butylphenyl)-1-propanol, optically active
N-(3-bromo-5-nitrosalicylidene)-2-amino-1,1-di(4-n-butoxy-3,5-di-tert-butylphenyl)-3-phenyl-1-propanol, optically active
N-(3-bromo-5-nitrosalicylidene)-2-amino-1,1-di(4-n-butoxy-3,5-di-tert-butylphenyl)-1-butanol, optically active N-(3-bromo-5-nitrosalicylidene)-2-amino-1,1-di(4-n-butoxy-3,5-di-tert-butylphenyl)-3-methyl-1-butanol, optically active
N-(3-bromo-5-nitrosalicylidene)-2-amino-1,1-di(4-n-butoxy-3,5-di-tert-butyphenyl)-4-methyl-1-pentanol, optically active
N-(3-bromo-5-nitrosalicylidene)-2-amino-1,1-di(4-n-butoxy-3,5-di-tert-butylphenyl)-3-methyl-1-pentanol, optically active
N-(3,5-dinitrosalicylidene)-2-amino-1,1-di(4-n-butoxy-3,5-di-tert-butylphenyl)-1-propanol, optically active
N-(3,5-dinitrosalicylidene)-2-amino-1,1-di(4-n-butoxy-3,5-di-tert-butylphenyl)-3-phenyl-1-propanol, optically active
N-(3,5-dinitrosalicylidene)-2-amino-1,1-di(4-n-butoxy-3,5-di-tert-butylphenyl)-1-butanol, optically active
N-(3,5-dinitrosalicylidene)-2-amino-1,1-di(4-n-butoxy-3,5-di-tert-butylphenyl)-3-methyl-1-butanol, optically active
N-(3,5-dinitrosalicylidene)-2-amino-1,1-di(4-n-butoxy-3,5-di-tert-butylphenyl)-4-methyl-1-pentanol, optically active
N-(3,5-dinitrosalicylidene)-2-amino-1,1-di(4-n-butoxy-3,5-di-tert-butylphenyl)-3-methyl-1-pentanol, optically active
N-(3-fluorosalicylidene)-2-amino-1,1-di(4-n-butoxy-3,5-di-tert-butylphenyl)-1-propanol, optically active
N-(3-fluorosalicylidene)-2-amino-1,1-di(4-n-butoxy-3,5-di-tert-butylphenyl)-3-phenyl-1-propanol, optically active
N-(3-fluorosalicylidene)-2-amino-1,1-di(4-n-butoxy-3,5-di-tert-butylphenyl)-1-butanol, optically active
N-(3-fluorosalicylidene)-2-amino-1,1-di(4-n-butoxy-3,5-di-tert-butylphenyl)-3-methyl-1-butanol, optically active
N-(3-fluorosalicylidene)-2-amino-1,1-di(4-n-butoxy-3,5-di-tert-butylphenyl)-4-methyl-1-pentanol, optically active
N-(3-fluorosalicylidene)-2-amino-1,1-di(4-n-butoxy-3,5-di-tert-butylphenyl)-3-methyl-1-pentanol; optically active
N-(5-fluorosalicylidene)-2-amino-1,1-di(4-n-butoxy-3,5-di-tert-butylphenyl)-1-propanol, optically active
N-(5-fluorosalicylidene)-2-amino-1,1-di(4-n-butoxy-3,5-di-tert-butylphenyl)-3-phenyl-1-propanol, optically active
N-(5-fluorosalicylidene)-2-amino-1,1-di(4-n-butoxy-3,5-di-tert-butylphenyl)-1-butanol, optically active
N-(5-fluorosalicylidene)-2-amino-1,1-di(4-n-butoxy-3,5-di-tert-butylphenyl)-3-methyl-1-butanol, optically active
N-(5-fluorosalicylidene)-2-amino-1,1-di(4-n-butoxy-3,5-di-tert-butylphenyl)-4-methyl-1-pentanol, optically active
N-(5-fluorosalicylidene)-2-amino-1,1-di(4-n-butoxy-3,5-di-tert-butylphenyl)-3-methyl-1-pentanol, optically active
N-(3,5-difluorosalicylidene)-2-amino-1,1-di(4-n-butoxy-3,5-di-tert-butylphenyl)-1-propanol, optically active
N-(3,5-difluorosalicylidene)-2-amino-1,1-di(4-n-butoxy-3,5-di-tert-butylphenyl)-3-phenyl-1-propanol, optically active
N-(3,5-difluorosalicylidene)-2-amino-1,1-di(4-n-butoxy-3,5-di-tert-butylphenyl)-1-butanol, optically active
N-(3,5-difluorosalicylidene)-2-amino-1,1-di(4-n-butoxy-3,5-di-tert-butylphenyl)-3-methyl-1-butanol, optically active
N-(3,5-difluorosalicylidene)-2-amino-1,1-di(4-n-butoxy-3,5-di-tert-butylphenyl)-4-methyl-1-pentanol, optically active
N-(3,5-difluorosalicylidene)-2-amino-1,1-di(4-n-butoxy-3,5-di-tert-butylphenyl)-3-methyl-1-pentanol, optically active
N-[5-(methoxycarbonyl)salicylidene]-2-amino-1,1-di(4-n-butoxy-3,5-di-tert-butylphenyl)-1-propanol, optically active
N-[5-(methoxycarbonyl)salicylidene]-2-amino-1,1-di(4-n-butoxy-3,5-di-tert-butylphenyl)-3-phenyl-1-propanol, optically active
N-[5-(methoxycarbonyl)salicylidene]-2-amino-1,1-di(4-n-butoxy-3,5-di-tert-butylphenyl)-1-butanol, optically active
N-[5-(methoxycarbonyl)salicylidene]-2-amino-1,1-di(4-n-butoxy-3,5-di-tert-butylphenyl)-3-methyl-1-butanol, optically active
N-[5-(methoxycarbonyl)salicylidene]-2-amino-1,1-di(4-n-butoxy-3,5-di-tert-butylphenyl)-4-methyl-1-pentanol, optically active
N-[5-(methoxycarbonyl)salicylidene]-2-amino-1,1-di(4-n-butoxy-3,5-di-tert-butylphenyl)-3-methyl-1-pentanol, optically active
N-(5-trifluoromethylsalicylidene)-2-amino-1,1-di(4-n-butoxy-3,5-di-tert-butylphenyl)-1-propanol, optically active
N-(5-trifluoromethylsalicylidene)-2-amino-1,1-di(4-n-butoxy-3,5-di-tert-butylphenyl)-3-phenyl-1-propanol, optically active
N-(5-trifluoromethylsalicylidene)-2-amino-1,1-di(4-n-butoxy-3,5-di-tert-butylphenyl)-1-butanol, optically active
N-(5-trifluoromethylsalicylidene)-2-amino-1,1-di(4-n-butoxy-3,5-di-tert-butylphenyl)-3-methyl-1-butanol, optically active
N-(5-trifluoromethylsalicylidene)-2-amino-1,1-di(4-n-butoxy-3,5-di-tert-butylphenyl)-4-methyl-1-pentanol, optically active
N-(5-trifluoromethylsalicylidene)-2-amino-1,1-di(4-n-butoxy-3,5-di-tert-butylphenyl)-3-methyl-1-pentanol, optically active
N-(5-cyanosalicylidene)-2-amino-1,1-di(4-n-butoxy-3,5-di-tert-butylphenyl)-1-propanol, optically active
N-(5-cyanosalicylidene)-2-amino-1,1-di(4-n-butoxy-3,5-di-tert-butylphenyl)-3-phenyl-1-propanol, optically active
N-(5-cyanosalicylidene)-2-amino-1,1-di(4-n-butoxy-3,5-di-tert-butylphenyl)-1-butanol, optically active
N-(5-cyanosalicylidene)-2-amino-1,1-di(4-n-butoxy-3,5-di-tert-butylphenyl)-3-methyl-1-butanol, optically active
N-(5-cyanosalicylidene)-2-amino-1,1-di(4-n-butoxy-3,5-di-tert-butylphenyl)-4-methyl-1-pentanol, optically active
N-(5-cyanosalicylidene)-2-amino-1,1-di(4-n-butoxy-3,5-di-tert-butylphenyl)-3-methyl-1-pentanol, optically active
N-(5-nitrosalicylidene)-2-amino-1,1-di(4-n-octyloxy-3,5-di-tert-butylphenyl)-1-propanol, optically active
N-(5-nitrosalicylidene)-2-amino-1,1-di(4-n-octyloxy-3,5-di-tert-butylphenyl)-3-phenyl-1-propanol, optically active
N-(5-nitrosalicylidene)-2-amino-1,1-di(4-n-octyloxy-3,5-di-tert-butylphenyl)-1-butanol, optically active
N-(5-nitrosalicylidene)-2-amino-1,1-di(4-n-octyloxy-3,5-di-tert-butylphenyl)-3-methyl-1-butanol, optically active
N-(5-nitrosalicylidene)-2-amino-1,1-di(4-n-octyloxy-3,5-di-tert-butylphenyl)-4-methyl-1-pentanol, optically active
N-(5-nitrosalicylidene)-2-amino-1,1-di(4-n-octyloxy-3,5-di-tert-butylphenyl)-3-methyl-1-pentanol, optically active
N-(3-nitrosalicylidene)-2-amino-1,1-di(4-n-octyloxy-3,5-di-tert-butylphenyl)-1-propanol, optically active
N-(3-nitrosalicylidene)-2-amino-1,1-di(4-n-octyloxy-3,5-di-tert-butylphenyl)-3-phenyl-1-propanol, optically active
N-(3-nitrosalicylidene)-2-amino-1,1-di(4-n-octyloxy-3,5-di-tert-butylphenyl)-1-butanol, optically active
N-(3-nitrosalicylidene)-2-amino-1,1-di(4-n-octyloxy-3,5-di-tert-butylphenyl)-3-methyl-1-butanol, optically active
N-(3-nitrosalicylidene)-2-amino-1,1-di(4-n-octyloxy-3,5-di-tert-butylphenyl)-4-methyl-1-pentanol, optically active N-(3-nitrosalicylidene)-2-amino-1,1-di(4-n-octyloxy-3,5-di-tert-butylphenyl)-3-methyl-1-pentanol, optically active
N-(3-bromo-5-nitrosalicylidene)-2-amino-1,1-di(4-n-octyloxy-3,5-di-tert-butylphenyl)-1-propanol, optically active
N-(3-bromo-5-nitrosalicylidene)-2-amino-1,1-di(4-n-octyloxy-3,5-di-tert-butylphenyl)-3-phenyl-1-propanol, optically active
N-(3-bromo-5-nitrosalicylidene)-2-amino-1,1-di(4-n-octyloxy-3,5-di-tert-butylphenyl)-1-butanol, optically active
N-(3-bromo-5-nitrosalicylidene)-2-amino-1,1-di(4-n-octyloxy-3,5-di-tert-butylphenyl)-3-methyl-1-butanol, optically active
N-(3-bromo-5-nitrosalicylidene)-2-amino-1,1-di(4-n-octyloxy-3,5-di-tert-butylphenyl)-4-methyl-1-pentanol, optically active
N-(3-bromo-5-nitrosalicylidene)-2-amino-1,1-di(4-n-octyloxy-3,5-di-tert-butylphenyl)-3-methyl-1-pentanol, optically active
N-(3,5-dinitrosalicylidene)-2-amino-1,1-di(4-n-octyloxy-3,5-di-tert-butylphenyl)-1-propanol, optically active
N-(3,5-dinitrosalicylidene)-2-amino-1,1-di(4-n-octyloxy-3,5-di-tert-butylphenyl)-3-phenyl-1-propanol, optically active
N-(3,5-dinitrosalicylidene)-2-amino-1,1-di(4-n-octyloxy-3,5-di-tert-butylphenyl)-1-butanol, optically active
N-(3,5-dinitrosalicylidene)-2-amino-1,1-di(4-n-octyloxy-3,5-di-tert-butylphenyl)-3-methyl-1-butanol, optically active
N-(3,5-dinitrosalicylidene)-2-amino-1,1-di(4-n-octyloxy-3,5-di-tert-butylphenyl)-4-methyl-1-pentanol, optically active
N-(3,5-dinitrosalicylidene)-2-amino-1,1-di(4-n-octyloxy-3,5-di-tert-butylphenyl)-3-methyl-1-pentanol, optically active
N-(3-fluorosalicylidene)-2-amino-1,1-di(4-n-octyloxy-3,5-di-tert-butylphenyl)-1-propanol, optically active
N-(3-fluorosalicylidene)-2-amino-1,1-di(4-n-octyloxy-3,5-di-tert-butylphenyl)-3-phenyl-1-propanol, optically active
N-(3-fluorosalicylidene)-2-amino-1,1-di(4-n-octyloxy-3,5-di-tert-butylphenyl)-1-butanol, optically active
N-(3-fluorosalicylidene)-2-amino-1,1-di(4-n-octyloxy-3,5-di-tert-butylphenyl)-3-methyl-1-butanol, optically active
N-(3-fluorosalicylidene)-2-amino-1,1-di(4-n-octyloxy-3,5-di-tert-butylphenyl)-4-methyl-1-pentanol, optically active
N-(3-fluorosalicylidene)-2-amino-1,1-di(4-n-octyloxy-3,5-di-tert-butylphenyl)-3-methyl-1-pentanol, optically active
N-(5-fluorosalicylidene)-2-amino-1,1-di(4-n-octyloxy-3,5-di-tert-butylphenyl)-1-propanol, optically active
N-(5-fluorosalicylidene)-2-amino-1,1-di(4-n-octyloxy-3,5-di-tert-butylphenyl)-3-phenyl-1-propanol, optically active
N-(5-fluorosalicylidene)-2-amino-1,1-di(4-n-octyloxy-3,5-di-tert-butylphenyl)-1-butanol, optically active
N-(5-fluorosalicylidene)-2-amino-1,1-di(4-n-octyloxy-3,5-di-tert-butylphenyl)-3-methyl-1-butanol, optically active
N-(5-fluorosalicylidene)-2-amino-1,1-di(4-n-octyloxy-3,5-di-tert-butylphenyl)-4-methyl-1-pentanol, optically active
N-(5-fluorosalicylidene)-2-amino-1,1-di(4-n-octyloxy-3,5-di-tert-butylphenyl)-3-methyl-1-pentanol, optically active
N-(3,5-difluorosalicylidene)-2-amino-1,1-di(4-n-octyloxy-3,5-di-tert-butylphenyl)-1-propanol, optically active
N-(3,5-difluorosalicylidene)-2-amino-1,1-di(4-n-octyloxy-3,5-di-tert-butylphenyl)-3-phenyl-1-propanol, optically active
N-(3,5-difluorosalicylidene)-2-amino-1,1-di(4-n-octyloxy-3,5-di-tert-butylphenyl)-1-butanol, optically active
N-(3,5-difluorosalicylidene)-2-amino-1,1-di(4-n-octyloxy-3,5-di-tert-butylphenyl)-3-methyl-1-butanol, optically active
N-(3,5-difluorosalicylidene)-2-amino-1,1-di(4-n-octyloxy-3,5-di-tert-butylphenyl)-4-methyl-1-pentanol, optically active
N-(3,5-difluorosalicylidene)-2-amino-1,1-di(4-methoxy-3,5-di-tert-butylphenyl)-3-methyl-1-pentanol, optically active
N-[5-(methoxycarbonyl)salicylidene]-2-amino-1,1-di(4-n-octyloxy-3,5-di-tert-butylphenyl)-1-propanol, optically active
N-[5-(methoxycarbonyl)salicylidene]-2-amino-1,1-di(4-n-octyloxy-3,5-di-tert-butylphenyl)-3-phenyl-1-propanol, optically active
N-[5-(methoxycarbonyl)salicylidene]-2-amino-1,1-di(4-n-octyloxy-3,5-di-tert-butylphenyl)-1-butanol, optically active
N-[5-(methoxycarbonyl)salicylidene]-2-amino-1,1-di(4-n-octyloxy-3,5-di-tert-butylphenyl)-3-methyl-1-butanol, optically active
N-[5-(methoxycarbonyl)salicylidene]-2-amino-1,1-di(4-n-octyloxy-3,5-di-tert-butyphenyl)-4-methyl-1-pentanol, optically active
N-[5-(methoxycarbonyl)salicylidene]-2-amino-1,1-di(4-n-octyloxy-3,5-di-tert-butylphenyl)-3-methyl-1-pentanol, optically active
N-(5-trifluoromethylsalicylidene)-2-amino-1,1-di(4-n-octyloxy-3,5-di-tert-butylphenyl)-1-propanol, optically active
N-(5-trifluoromethylsalicylidene)-2-amino-1,1-di(4-n-octyloxy-3,5-di-tert-butylphenyl)-3-phenyl-1-propanol, optically active
N-(5-trifluoromethylsalicylidene)-2-amino-1,1-di(4-n-octyloxy-3,5-di-tert-butylphenyl)-1-butanol, optically active
N-(5-trifluoromethylsalicylidene)-2-amino-1,1-di(4-n-octyloxy-3,5-di-tert-butylphenyl)-3-methyl)-3-methyl-1-butanol, optically active
N-(5-trifluoromethylsalicylidene)-2-amino-1,1-di(4-n-octyloxy-3,5-di-tert-butylphenyl)-4-methyl-1-pentanol, optically active
N-(5-trifluoromethylsalicylidene)-2-amino-1,1-di(4-n-octyloxy-3,5-di-tert-butylphenyl)-3-methyl-1-pentanol, optically active
N-(5-cyanosalicylidene)-2-amino-1,1-di(4-n-octyloxy-3,5-di-tert-butylphenyl)-1-propanol, optically active
N-(5-cyanosalicylidene)-2-amino-1,1-di(4-n-octyloxy-3,5-di-tert-butylphenyl)-3-phenyl-1-propanol, optically active
N-(5-cyanosalicylidene)-2-amino-1,1-di(4-n-octyloxy-3,5-di-tert-butylphenyl)-1-butanol, optically active
N-(5-cyanosalicylidene)-2-amino-1,1-di(4-n-octyloxy-3,5-di-tert-butylphenyl)-3-methyl-1-butanol, optically active
N-(5-cyanosalicylidene)-2-amino-1,1-di(4-n-octyloxy-3,5-di-tert-butylphenyl)-4-methyl-1-pentanol, and optically active
N-(5-cyanosalicylidene)-2-amino-1,1-di(4-n-octyloxy-3,5-di-tert-butylphenyl)-3-methyl-1-pentanol.

In the optically active salicylideneaminoalcohol (1), two optical isomers of an R form and an S form are present, and any of them may be used.

The optically active salicylideneaminoalcohol (1) can be prepared by reacting an amino acid ester represented by the formula (6):

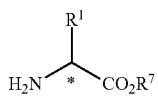

(6)

(wherein R¹ and * represent the same meaning as defined above, and R⁷ represents an alkyl group having 1 to 12 carbon atoms or an aralkyl group having 7 to 12 carbon atoms) or a salt thereof with a compound represented by the formula (7):

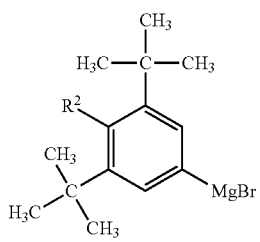

(7)

(wherein R² represents the same meaning as defined above) at −20 to 50° C. to obtain an optically active aminoalcohol represented by the formula (5):

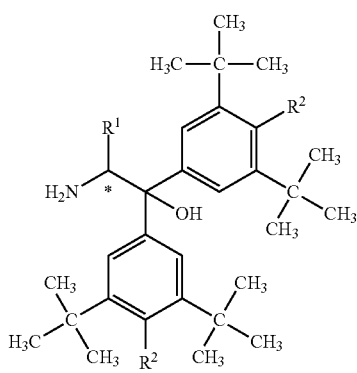

(5)

(wherein R¹, R² and * represent the same meaning as defined above), and reacting the resulting optically active aminoalcohol represented by the formula (5) and an aldehyde represented by the formula (8):

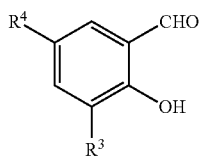

(8)

(wherein R³ and R⁴ represent the same meaning as defined above) at −20 to 50° C.

Examples of the alkyl group having 1 to 12 carbon atoms represented by R⁷ include a methyl group and an ethyl group, and examples of the aralkyl group having 7 to 12 carbon atoms include a benzyl group.

Examples of the optically active aminoalcohol compound represented by the formula (5) include:
optically active 2-amino-1,1-di(3,5-di-tert-butylphenyl)-1-propanol, optically active 2-amino-1,1-di(3,5-di-tert-butylphenyl)-3-phenyl-propanol, optically active 2-amino-1,1-di(3,5-di-tert-butylphenyl)-1-butanol, optically active 2-amino-1,1-di(3,5-di-tert-butylphenyl)-3-methyl-1-butanol, optically active 2-amino-1,1-di(3,5-di-tert-butylphenyl)-4-methyl-1-pentanol, optically active 2-amino-1,1-di(3,5-di-tert-butylphenyl)-3-methyl-1-pentanol,
optically active 2-amino-1,1-di(4-methoxy-3,5-di-tert-butylphenyl)-1-propanol, optically active 2-amino-1,1-di(4-methoxy-3,5-di-tert-butylphenyl)-3-phenyl-1-propanol, optically active 2-amino-1,1-di(4-methoxy-3,5-di-tert-butylphenyl)-1-butanol, optically active 2-amino-1,1-di(4-methoxy-3,5-di-tert-butylphenyl)-3-methyl-1-butanol, optically active 2-amino-1,1-di(4-methoxy-3,5-di-tert-butylphenyl)-4-methyl-1-pentanol, optically active 2-amino-1,1-di(4-methoxy-3,5-di-tert-butylphenyl)-3-methyl-1-pentanol,
optically active 2-amino-1,1-di(4-n-butoxy-3,5-di-tert-butylphenyl)-1-propanol, optically active 2-amino-1,1-di(4-n-butoxy-3,5-di-tert-butylphenyl)-3-phenyl-1-propanol, optically active 2-amino-1,1-di(4-n-butoxy-3,5-di-tert-butylphenyl)-1-butanol, optically active 2-amino-1,1-di(4-n-butoxy-3,5-di-tert-butylphenyl)-3-methyl-1-butanol, optically active 2-amino-1,1-di(4-n-butoxy-3,5-di-tert-butylphenyl)-4-methyl-1-pentanol, optically active 2-amino-1,1-di(4-n-butoxy-3,5-di-tert-butylphenyl)-3-methyl-1-pentanol,
optically active 2-amino-1,1-di(4-n-octyloxy-3,5-di-tert-butylphenyl)-1-propanol, 2-amino-1,1-di(4-n-octyloxy-3,5-di-tert-butylphenyl)-3-phenyl-1-propanol, optically active 2-amino-1,1-di(4-n-octyloxy-3,5-di-tert-butylphenyl)-1-butanol, optically active 2-amino-1,1-di(4-n-octyloxy-3,5-di-tert-butylphenyl)-3-methyl-1-butanol, optically active 2-amino-1,1-di(4-n-octyloxy-3,5-di-tert-butylphenyl)-4-methyl-1-pentanol and optically active 2-amino-1,1-di(4-n-octyloxy-3,5-di-tert-butylphenyl)-3-methyl-1-pentanol.

Examples of the aldehyde represented by the formula (8) include 5-nitrosalicylaldehyde, 3-nitrosalicylaldehyde, 3-bromo-5-nitrosalicylaldehyde, 3,5-dinitrosalicylaldehyde, 3-fluorosalicylaldehyde, 5-fluorosalicylaldehyde, 3,5-difluorosalicylaldehyde, 5-(methoxycarbonyl)salicylaldehyde, 5-(ethoxycarbonyl)salicylaldehyde, 5-trifluoromethylsalicylaldehyde, 5-heptafluoropropylsalicylaldehyde, 5-cyanosalicylaldehyde, 5-methanesulfonylsalicylaldehyde and 5-trifluoromethanesulfonylsalicylaldehyde.

An asymmetric copper complex can be prepared by reacting the optically active salicylideneaminoalcohol (1) and the copper compound. The amount of the optically active salicylideneaminoalcohol (1) used is usually 0.5 to 2 moles based on 1 mole of the copper compound.

The reaction between the copper compound and the optically active salicylideneaminoalcohol (1) is usually performed in an organic solvent. Examples of the organic solvent include aromatic hydrocarbons such as toluene and xylene, halogenated hydrocarbons such as dichloromethane, chloroform and dichloroethane, esters such as ethyl acetate. Two or more kinds of the organic solvents may be used by mixing them. The amount of the organic solvent used is not limited.

The reaction temperature is usually 20 to 150° C., preferably 20 to 120° C.

The reaction can be more smoothly progressed by reacting the copper compound and the optically active salicylideneaminoalcohol (1) in the presence of an alkali metal alcoholate such as sodium methylate. The amount of the alkali metal alcoholate used is usually 1 mole or more based on 1 mole of the optically active salicylideneaminoalcohol (1). When a divalent copper compound is used, it is preferable that 2 moles or more of the alkali metal alcoholate is used based on 1 mole of the optically active salicylideneaminoalcohol (1). There is no upper limit of the amount of the alkali metal alcoholate used, but since when the amount is too large, it leads to an economical disadvantage, actually, the amount of the alkali metal alcoholate is 10 moles or less based on 1 mole of the optically active salicylideneaminoalcohol (1).

Thus, a mixture containing the asymmetric copper complex is obtained, and the mixture may be used as it is for a reaction between a diazoacetic acid ester represented by the formula (2):

$$N_2CHCO_2R^5 \qquad (2)$$

(wherein $R^5$ represents an alkyl group having 1 to 15 carbon atoms or an aryl group having 6 to 10 carbon atoms)
(hereinafter, abbreviated as diazoacetic acid ester (2)) with a compound represented by the formula (3):

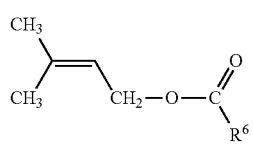

(3)

(wherein $R^6$ represents an alkyl group having 1 to 15 carbon atoms, an aryl group having 6 to 10 carbon atoms or an aralkyl group having 7 to 20 carbon atoms)
(hereinafter, abbreviated as compound (3)), or the mixture containing the asymmetric copper complex may be filtered or washed, and used in the reaction between the diazoacetic acid ester (2) and the compound (3). Further, the asymmetric copper complex is taken out by concentrating the mixture containing the asymmetric copper complex, and the asymmetric copper complex taken out may be used in the reaction between the diazoacetic acid ester (2) and the compound (3). The asymmetric copper complex taken out may be purified by a normal purification means such as washing and recrystallization.

The asymmetric copper complex can be usually taken out in the form of a copper binuclear complex including two copper atoms and two optically active salicylideneaminoalcohols (1). It is preferable to use the asymmetric copper complex taken out in the reaction between the diazoacetic acid ester (2) and the compound (3).

As the asymmetric copper complex,
an asymmetric copper complex obtained by reacting the optically active salicylideneaminoalcohol (1) in which $R^1$ is an alkyl group having 1 to 4 carbon atoms, $R^2$ is a hydrogen atom, $R^3$ is a hydrogen atom, and $R^4$ is a nitro group, and the copper compound, an asymmetric copper complex obtained by reacting the optically active salicylideneaminoalcohol (1) in which $R^1$ is an alkyl group having 1 to 4 carbon atoms, $R^2$ is an alkoxy group having 1 to 4 carbon atoms, $R^3$ is a hydrogen atom, and $R^4$ is a nitro group, and the copper compound, an asymmetric copper complex obtained by reacting the optically active salicylideneaminoalcohol (1) in which $R^1$ is an alkyl group having 1 to 4 carbon atoms, $R^2$ is a hydrogen atom, $R^3$ is a nitro group, and $R^4$ is a hydrogen atom, and the copper compound, an asymmetric copper complex obtained by reacting the optically active salicylideneaminoalcohol (1) in which $R^1$ is an alkyl group having 1 to 4 carbon atoms, $R^2$ is a hydrogen atom, $R^3$ is a nitro group, and $R^4$ is a nitro group, and the copper compound, an asymmetric copper complex obtained by reacting the optically active salicylideneaminoalcohol (1) in which $R^1$ is an alkyl group having 1 to 4 carbon atoms, $R^2$ is a hydrogen atom, $R^3$ is a halogen atom, and $R^4$ is a hydrogen atom, and the copper compound, an asymmetric copper complex obtained by reacting the optically active salicylideneaminoalcohol (1) in which $R^1$ is an alkyl group having 1 to 4 carbon atoms, $R^2$ is a hydrogen atom, $R^3$ is a halogen atom, and $R^4$ is a nitro group, and the copper compound, an asymmetric copper complex obtained by reacting the optically active salicylideneaminoalcohol (1) in which $R^1$ is an alkyl group having 1 to 4 carbon atoms, $R^2$ is a hydrogen atom, $R^3$ is a halogen atom, and $R^4$ is a halogen atom, and the copper compound, an asymmetric copper complex obtained by reacting the optically active salicylideneaminoalcohol (1) in which $R^1$ is an alkyl group having 1 to 4 carbon atoms, $R^2$ is a hydrogen atom, $R^3$ is a hydrogen atom, and $R^4$ is an alkoxycarbonyl group having 2 to 5 carbon atoms, and the copper compound, an asymmetric copper complex obtained by reacting the optically active salicylideneaminoalcohol (1) in which $R^1$ is a benzyl group, $R^2$ is a hydrogen atom, $R^3$ is a hydrogen atom, and $R^4$ is a nitro group, and the copper compound, an asymmetric copper complex obtained by reacting the optically active salicylideneaminoalcohol (1) in which $R^1$ is a benzyl group, $R^2$ is a hydrogen atom, $R^3$ is a nitro group, and $R^4$ is a nitro group, and the copper compound, an asymmetric copper complex obtained by reacting the optically active salicylideneaminoalcohol (1) in which $R^1$ is a phenyl group, $R^2$ is a hydrogen atom, $R^3$ is a hydrogen atom, and $R^4$ is a nitro group, and the copper compound, and an asymmetric copper complex obtained by reacting the optically active salicylideneaminoalcohol (1) in which $R^1$ is a phenyl group, $R^2$ is a hydrogen atom, $R^3$ is a nitro group, and $R^4$ is a nitro group, and the copper compound,
are preferable.

Among them, the asymmetric copper complex obtained by reacting the optically active salicylideneaminoalcohol (1) in which $R^1$ is an alkyl group having 2 to 4 carbon atoms, $R^2$ is a hydrogen atom, $R^3$ is a hydrogen atom, and $R^4$ is a nitro group, and the copper compound, the asymmetric copper complex obtained by reacting the optically active salicylideneaminoalcohol (1) in which $R^1$ is a benzyl group, $R^2$ is a hydrogen atom, $R^3$ is a hydrogen atom, and $R^4$ is a nitro group, and the copper compound, the asymmetric copper complex obtained by reacting the optically active salicylideneaminoalcohol (1) in which $R^1$ is an alkyl group having 2 to 4 carbon atoms, $R^2$ is a hydrogen atom, $R^3$ is a nitro group, and $R^4$ is a hydrogen atom, and the copper compound, the asymmetric copper complex obtained by reacting the optically active salicylideneaminoalcohol (1) in which $R^1$ is an alkyl group having 2 to 4 carbon atoms, $R^2$ is a hydrogen atom, $R^3$ is a nitro group, and $R^4$ is a nitro group, and the copper compound, the asymmetric copper complex obtained by reacting the optically active salicylideneaminoalcohol (1) in which $R^1$ is an alkyl group having 2 to 4 carbon atoms, $R^2$ is a hydrogen atom, $R^3$ is a halogen atom, and $R^4$ is a nitro group, and the copper compound, and the asymmetric copper complex obtained by reacting the optically active salicylideneaminoalcohol (1) in which $R^1$ is an alkyl group having 2 to 4 carbon atoms, $R^2$ is a hydrogen atom, $R^3$ is a halogen atom, and $R^4$ is a halogen atom, and the copper compound, are more preferable.

Examples of the asymmetric copper complex include:
a complex of optically active N-(5-nitrosalicylidene)-2-amino-1,1-di(3,5-di-tert-butylphenyl)-1-propanol and copper, a complex of optically active
N-(5-nitrosalicylidene)-2-amino-1,1-di(3,5-di-tert-butylphenyl)-3-phenyl-1-propanol and copper, a complex of optically active
N-(5-nitrosalicylidene)-2-amino-1,1-di(3,5-di-tert-butylphenyl)-1-butanol and copper, a complex of optically active
N-(5-nitrosalicylidene)-2-amino-1,1-di(3,5-di-tert-butylphenyl)-3-methyl-1-butanol and copper, a complex of optically active
N-(5-nitrosalicylidene)-2-amino-1,1-di(3,5-di-tert-butylphenyl)-4-methyl-1-pentanol and copper, a complex of optically active
N-(5-nitrosalicylidene)-2-amino-1,1-di(3,5-di-tert-butylphenyl)-3-methyl-1-pentanol and copper,
a complex of optically active
N-(3-nitrosalicylidene)-2-amino-1,1-di(3,5-di-tert-butylphenyl)-1-propanol and copper, a complex of optically active
N-(3-nitrosalicylidene)-2-amino-1,1-di(3,5-di-tert-butylphenyl)-3-phenyl-1-propanol and copper, a complex of optically active
N-(3-nitrosalicylidene)-2-amino-1,1-di(3,5-di-tert-butylphenyl)-1-butanol and copper, a complex of optically active
N-(3-nitrosalicylidene)-2-amino-1,1-di(3,5-di-tert-butylphenyl)-3-methyl-1-butanol and copper, a complex of optically active
N-(3-nitrosalicylidene)-2-amino-1,1-di(3,5-di-tert-butylphenyl)-4-methyl-1-pentanol and copper, a complex of optically active
N-(3-nitrosalicylidene)-2-amino-1,1-di(3,5-di-tert-butylphenyl)-3-methyl-1-pentanol and copper,
a complex of optically active
N-(3-bromo-5-nitrosalicylidene)-2-amino-1,1-di(3,5-di-tert-butylphenyl)-1-propanol and copper, a complex of optically active
N-(3-bromo-5-nitrosalicylidene)-2-amino-1,1-di(3,5-di-tert-butylphenyl)-3-phenyl-1-propanol and copper, a complex of optically active
N-(3-bromo-5-nitrosalicylidene)-2-amino-1,1-di(3,5-di-tert-butylphenyl)-1-butanol and copper, a complex of optically active
N-(3-bromo-5-nitrosalicylidene)-2-amino-1,1-di(3,5-di-tert-butylphenyl)-3-methyl-1-butanol and copper, a complex of optically active
N-(3-bromo-5-nitrosalicylidene)-2-amino-1,1-di(3,5-di-tert-butylphenyl)-4-methyl-1-pentanol and copper, a complex of optically active
N-(3-bromo-5-nitrosalicylidene)-2-amino-1,1-di(3,5-di-tert-butylphenyl)-3-methyl-1-pentanol and copper,
a complex of optically active
N-(3,5-dinitrosalicylidene)-2-amino-1,1-di(3,5-di-tert-butylphenyl)-1-propanol and copper, a complex of optically active
N-(3,5-dinitrosalicylidene)-2-amino-1,1-di(3,5-di-tert-butylphenyl)-3-phenyl-1-propanol and copper, a complex of optically active
N-(3,5-dinitrosalicylidene)-2-amino-1,1-di(3,5-di-tert-butylphenyl)-1-butanol and copper, a complex of optically active
N-(3,5-dinitrosalicylidene)-2-amino-1,1-di(3,5-di-tert-butylphenyl)-3-methyl-1-butanol and copper, a complex of optically active
N-(3,5-dinitrosalicylidene)-2-amino-1,1-di(3,5-di-tert-butylphenyl)-4-methyl-1-pentanol and copper, a complex of optically active
N-(3,5-dinitrosalicylidene)-2-amino-1,1-di(3,5-di-tert-butylphenyl)-3-methyl-1-pentanol and copper,
a complex of optically active
N-(3-fluorosalicylidene)-2-amino-1,1-di(3,5-di-tert-butylphenyl)-1-propanol and copper, a complex of optically active N-(3-fluorosalicylidene)-2-amino-1,1-di(3,5-di-tert-butylphenyl)-3-phenyl-1-propanol and copper, a complex of optically active
N-(3-fluorosalicylidene)-2-amino-1,1-di(3,5-di-tert-butylphenyl)-1-butanol and copper, a complex of optically active
N-(3-fluorosalicylidene)-2-amino-1,1-di(3,5-di-tert-butylphenyl)-3-methyl-1-butanol and copper, a complex of optically active
N-(3-fluorosalicylidene)-2-amino-1,1-di(3,5-di-tert-butylphenyl)-4-methyl-1-pentanol and copper, a complex of optically active
N-(3-fluorosalicylidene)-2-amino-1,1-di(3,5-di-tert-butylphenyl)-3-methyl-1-pentanol and copper,
a complex of optically active
N-(5-fluorosalicylidene)-2-amino-1,1-di(3,5-di-tert-butylphenyl)-1-propanol and copper, a complex of optically active
N-(5-fluorosalicylidene)-2-amino-1,1-di(3,5-di-tert-butylphenyl)-3-phenyl-1-propanol and copper, a complex of optically active
N-(5-fluorosalicylidene)-2-amino-1,1-di(3,5-di-tert-butylphenyl)-1-butanol and copper, a complex of optically active
N-(5-fluorosalicylidene)-2-amino-1,1-di(3,5-di-tert-butylphenyl)-3-methyl-1-butanol and copper, a complex of optically active
N-(5-fluorosalicylidene)-2-amino-1,1-di(3,5-di-tert-butylphenyl)-4-methyl-1-pentanol and copper, a complex of optically active
N-(5-fluorosalicylidene)-2-amino-1,1-di(3,5-di-tert-butylphenyl)-3-methyl-1-pentanol and copper,
a complex of optically active
N-(3,5-difluorosalicylidene)-2-amino-1,1-di(3,5-di-tert-butylphenyl)-1-propanol and copper, a complex of optically active N-(3,5-difluorosalicylidene)-2-amino-1,1-di(3,5-di-tert-butylphenyl)-3-phenyl-1-propanol and copper, a complex of optically active N-(3,5-difluorosalicylidene)-2-amino-1,1-di(3,5-di-tert-butylphenyl)-1-butanol and copper, a complex of optically active N-(3,5-difluorosalicylidene)-2-amino-1,1-di(3,5-di-tert-butylphenyl)-3-methyl-1-butanol and copper, a complex of optically active N-(3,5-difluorosalicylidene)-2-amino-1,1-di(3,5-di-tert-butylphenyl)-4-methyl-1-pentanol and copper, a complex of optically active N-(3,5-difluorosalicylidene)-2-amino-1,1-di(3,5-di-tert-butylphenyl)-3-methyl-1-pentanol and copper, a complex of optically active N-[5-(methoxycarbonyl)salicylidene]-2-amino-1,1-di(3,5-di-tert-butylphenyl)-1-propanol and copper, a complex of optically active N-[5-(methoxycarbonyl)salicylidene]-2-amino-1,1-di(3,5-di-tert-butylphenyl)-3-phenyl-1-propanol and copper, a complex of optically active N-[5-(methoxycarbonyl)salicylidene]-2-amino-1,1-di(3,5-di-tert-butylphenyl)-1-butanol and copper, a complex of optically active N-[5-(methoxycarbonyl)salicylidene]-2-amino-1,1-di(3,5-di-tert-butylphenyl)-3-methyl-1-butanol and copper, a complex of optically active N-[5-(methoxycarbonyl)salicylidene]-2-amino-1,1-di(3,5-di-tert-butylphenyl)-4-methyl-1-pentanol and copper, a complex of optically active N-[5-(methoxycarbonyl)salicylidene]-2-amino-1,1-di(3,5-di-tert-butylphenyl)-3-methyl-1-pentanol and copper, a complex of optically active N-(5-trifluoromethylsalicylidene)-2-amino-1,1-di(3,5-di-tert-butylphenyl)-1-propanol and copper, a complex of optically active N-(5-trifluoromethylsalicylidene)-2-amino-1,1-di(3,5-di-tert-butylphenyl)-3-phenyl-1-propanol and copper, a complex of optically active N-(5-trifluoromethylsalicylidene)-2-amino-1,1-di(3,5-di-tert-butylphenyl)-1-butanol and copper, a complex of optically active N-(5-trifluoromethylsalicylidene)-2-amino-1,1-di(3,5-di-tert-butylphenyl)-3-methyl-1-butanol and copper, a complex of optically active N-(5-trifluoromethylsalicylidene)-2-amino-1,1-di(3,5-di-tert-butylphenyl)-4-methyl-1-pentanol and copper, a complex of optically active N-(5-trifluoromethylsalicylidene)-2-amino-1,1-di(3,5-di-tert-butylphenyl)-3-methyl-1-pentanol and copper, a complex of optically active N-(5-cyanosalicylidene)-2-amino-1,1-di(3,5-di-tert-butylphenyl)-1-propanol and copper, a complex of optically active N-(5-cyanosalicylidene)-2-amino-1,1-di(3,5-di-tert-butylphenyl)-3-phenyl-1-propanol and copper, a complex of optically active N-(5-cyanosalicylidene)-2-amino-1,1-di(3,5-di-tert-butylphenyl)-1-butanol and copper, a complex of optically active N-(5-cyanosalicylidene)-2-amino-1,1-di(3,5-di-tert-butylphenyl)-3-methyl-1-butanol and copper, a complex of optically active N-(5-cyanosalicylidene)-2-amino-1,1-di(3,5-di-tert-butylphenyl)-4-methyl-1-pentanol and copper, a complex of optically active N-(5-cyanosalicylidene)-2-amino-1,1-di(3,5-di-tert-butylphenyl)-3-methyl-1-pentanol and copper, a complex of optically active N-(5-nitrosalicylidene)-2-amino-1,1-di(4-methoxy-3,5-di-tert-butylphenyl)-1-propanol and copper, a complex of optically active N-(5-nitrosalicylidene)-2-amino-1,1-di(4-methoxy-3,5-di-tert-butylphenyl)-3-phenyl-1-propanol and copper, a complex of optically active N-(5-nitrosalicylidene)-2-amino-1,1-di(4-methoxy-3,5-di-tert-butylphenyl)-1-butanol and copper, a complex of optically active N-(5-nitrosalicylidene)-2-amino-1,1-di(4-methoxy-3,5-di-tert-butylphenyl)-3-methyl-1-butanol and copper, a complex of optically active N-(5-nitrosalicylidene)-2-amino-1,1-di(4-methoxy-3,5-di-tert-butylphenyl)-4-methyl-1-pentanol and copper, a complex of optically active N-(5-nitrosalicylidene)-2-amino-1,1-di(4-methoxy-3,5-di-tert-butylphenyl)-3-methyl-1-pentanol and copper, a complex of optically active N-(3-nitrosalicylidene)-2-amino-1,1-di(4-methoxy-3,5-di-tert-butylphenyl)-1-propanol and copper, a complex of optically active N-(3-nitrosalicylidene)-2-amino-1,1-di(4-methoxy-3,5-di-tert-butylphenyl)-3-phenyl-1-propanol and copper, a complex of optically active N-(3-nitrosalicylidene)-2-amino-1,1-di(4-methoxy-3,5-di-tert-butylphenyl)-1-butanol and copper, a complex of optically active N-(3-nitrosalicylidene)-2-amino-1,1-di(4-methoxy-3,5-di-tert-butylphenyl)-3-methyl-1-butanol and copper, a complex of optically active N-(3-nitrosalicylidene)-2-amino-1,1-di(4-methoxy-3,5-di-tert-butylphenyl)-4-methyl-1-pentanol and copper, a complex of optically active N-(3-nitrosalicylidene)-2-amino-1,1-di(4-methoxy-3,5-di-tert-butylphenyl)-3-methyl-1-pentanol and copper, a complex of optically active N-(3-bromo-5-nitrosalicylidene)-2-amino-1,1-di(4-methoxy-3,5-di-tert-butylphenyl)-1-propanol and copper, a complex of optically active N-(3-bromo-5-nitrosalicylidene)-2-amino-1,1-di(4-methoxy-3,5-di-tert-butylphenyl)-3-phenyl-1-propanol and copper, a complex of optically active N-(3-bromo-5-nitrosalicylidene)-2-amino-1,1-di(4-methoxy-3,5-di-tert-butylphenyl)-1-butanol and copper, a complex of optically active N-(3-bromo-5-nitrosalicylidene)-2-amino-1,1-di(4-methoxy-3,5-di-tert-butylphenyl)-3-methyl-1-butanol and copper, a complex of optically active N-(3-bromo-5-nitrosalicylidene)-2-amino-1,1-di(4-methoxy-3,5-di-tert-butylphenyl)-4-methyl-1-pentanol and copper, a complex of optically active N-(3-bromo-5-nitrosalicylidene)-2-amino-1,1-di(4-methoxy-3,5-di-tert-butylphenyl)-3-methyl-1-pentanol and copper, a complex of optically active N-(3,5-dinitrosalicylidene)-2-amino-1,1-di(4-methoxy-3,5-di-tert-butylphenyl)-1-propanol and copper, a complex of optically active N-(3,5-dinitrosalicylidene)-2-amino-1,1-di(4-methoxy-3,5-di-tert-butylphenyl)-3-phenyl-1-propanol and copper, a complex of optically active N-(3,5-dinitrosalicylidene)-2-amino-1,1-di(4-methoxy-3,5-di-tert-butylphenyl)-1-butanol and copper, a complex of optically active N-(3,5-dinitrosalicylidene)-2-amino-1,1-di(4-methoxy-3,5-di-tert-butylphenyl)-3-methyl-1-butanol and copper, a complex of optically active N-(3,5-dinitrosalicylidene)-2-amino-1,1-di(4-methoxy-3,5-di-tert-butylphenyl)-4-methyl-1-pentanol and copper, a complex of optically active N-(3,5-dinitrosalicylidene)-2-amino-1,1-di(4-methoxy-3,5-di-tert-butylphenyl)-3-methyl-1-pentanol and copper, a complex of optically active N-(3-fluorosalicylidene)-2-amino-1,1-di(4-methoxy-3,5-di-tert-butylphenyl)-1-propanol and copper, a complex of optically active N-(3-fluorosalicylidene)-2-amino-1,1-di(4-methoxy-3,5-di-tert-butylphenyl)-3-phenyl-1-propanol and copper, a complex of optically active N-(3-fluorosalicylidene)-2-amino-1,1-di(4-methoxy-3,5-di-tert-butylphenyl)-1-butanol and copper, a complex of optically active N-(3-fluorosalicylidene)-2-amino-1,1-di(4-methoxy-3,5-di-tert-butylphenyl)-3-methyl-1-butanol and copper, a complex of optically active N-(3-fluorosalicylidene)-2-amino-1,1-di(4-methoxy-3,5-di-tert-butylphenyl)-4-methyl-1-pentanol and copper, a complex of optically active N-(3-fluorosalicylidene)-2-amino-1,1-di(4-methoxy-3,5-di-tert-butylphenyl)-3-methyl-1-pentanol and copper, a complex of optically active N-(5-fluorosalicylidene)-2-amino-1,1-di(4-methoxy-3,5-di-tert-butylphenyl)-1-propanol and copper, a complex of optically active N-(5-fluorosalicylidene)-2-amino-1,1-di(4-methoxy-3,5-di-tert-butylphenyl)-3-phenyl-1-propanol and copper, a complex of optically active N-(5-fluorosalicylidene)-2-amino-1,1-di(4-methoxy-3,5-di-tert-butylphenyl)-1-butanol and copper, a complex of optically active N-(5-fluorosalicylidene)-2-amino-1,1-di(4-methoxy-3,5-di-tert-butylphenyl)-3-methyl-1-butanol and copper, a complex of optically active N-(5-fluorosalicylidene)-2-amino-1,1-di(4-methoxy-3,5-di-tert-butylphenyl)-4-methyl-1-pentanol and copper, a complex of optically active N-(5-fluorosalicylidene)-2-amino-1,1-di(4-methoxy-3,5-di-tert-butylphenyl)-3-methyl-1-pentanol and copper, a complex of optically-active N-(3,5-difluorosalicylidene)-2-amino-1,1-di(4-methoxy-3,5-di-tert-butylphenyl)-1-propanol and copper, a complex of optically active N-(3,5-difluorosalicylidene)-2-amino-1,1-di(4-methoxy-3,5-di-tert-butylphenyl)-3-phenyl-1-propanol and copper, a complex of optically active N-(3,5-difluorosalicylidene)-2-amino-1,1-di(4-methoxy-3,5-di-tert-butylphenyl)-1-butanol and copper, a complex of optically active N-(3,5-difluorosalicylidene)-2-amino-1,1-di(4-methoxy-3,5-di-tert-butylphenyl)-3-methyl-1-butanol and copper, a complex of optically active N-(3,5-difluorosalicylidene)-2-amino-1,1-di(4-methoxy-3,5-di-tert-butylphenyl)-4-methyl-1-pentanol and copper, a complex of optically active N-(3,5-difluorosalicylidene)-2-amino-1,1-di(4-methoxy-3,5-di-tert-butylphenyl)-3-methyl-1-pentanol and copper, a complex of optically active N-[5-(methoxycarbonyl)salicylidene]-2-amino-1,1-di(4-methoxy-3,5-di-tert-butylphenyl)-1-propanol and copper, a complex of optically active N-[5-(methoxycarbonyl)salicylidene]-2-amino-1,1-di(4-methoxy-3,5-di-tert-butylphenyl)-3-phenyl-1-propanol and copper, a complex of optically active N-[5-(methoxycarbonyl)salicylidene]-2-amino-1,1-di(4-methoxy-3,5-di-tert-butylphenyl)-1-butanol and copper, a complex of optically active N-[5-(methoxycarbonyl)salicylidene]-2-amino-1,1-di(4-methoxy-3,5-di-tert-butylphenyl)-3-methyl-1-butanol and copper, a complex of optically active N-[5-(methoxycarbonyl)salicylidene]-2-amino-1,1-di(4-methoxy-3,5-di-tert-butylphenyl)-4-methyl-1-pentanol and copper, a complex of optically active N-[5-(methoxycarbonyl)salicylidene]-2-amino-1,1-di(4-methoxy-3,5-di-tert-butylphenyl)-3-methyl-1-pentanol and copper, a complex of optically active N-(5-trifluoromethylsalicylidene)-2-amino-1,1-di(4-methoxy-3,5-di-tert-butylphenyl)-1-propanol and copper, a complex of optically active N-(5-trifluoromethylsalicylidene)-2-amino-1,1-di(4-methoxy-3,5-di-tert-butylphenyl)-3-phenyl-1-propanol and copper, a complex of optically active N-(5-trifluoromethylsalicylidene)-2-amino-1,1-di(4-methoxy-3,5-di-tert-butylphenyl)-1-butanol and copper, a complex of optically active N-(5-trifluoromethylsalicylidene)-2-amino-1,1-di(4-methoxy-3,5-di-tert-butylphenyl)-3-methyl-1-butanol and copper, a complex of optically active N-(5-trifluoromethylsalicylidene)-2-amino-1,1-di(4-methoxy-3,5-di-tert-butylphenyl)-4-methyl-1-pentanol and copper, a complex of optically active N-(5-trifluoromethylsalicylidene)-2-amino-1,1-di(4-methoxy-3,5-di-tert-butylphenyl)-3-methyl-1-pentanol and copper, a complex of optically active N-(5-cyanosalicylidene)-2-amino-1,1-di(4-methoxy-3,5-di-tert-butylphenyl)-1-propanol and copper, a complex of optically active N-(5-cyanosalicylidene)-2-amino-1,1-di(4-methoxy-3,5-di-tert-butylphenyl)-3-phenyl-1-propanal and copper, a complex of optically active N-(5-cyanosalicylidene)-2-amino-1,1-di(4-methoxy-3,5-di-tert-butylphenyl)-1-butanol and copper, a complex of optically active N-(5-cyanosalicylidene)-2-amino-1,1-di(4-methoxy-3,5-di-tert-butylphenyl)-3-methyl-1-butanol and copper, a complex of optically active N-(5-cyanosalicylidene)-2-amino-1,1-di(4-methoxy-3,5-di-tert-butylphenyl)-4-methyl-1-pentanol and copper, a complex of optically active N-(5-cyanosalicylidene)-2-amino-1,1-di(4-methoxy-3,5-di-tert-butylphenyl)-3-methyl-1-pentanol and copper, a complex of optically active N-(5-nitrosalicylidene)-2-amino-1,1-di(4-n-butoxy-3,5-di-tert-butylphenyl)-1-propanol and copper, a complex of optically active N-(5-nitrosalicylidene)-2-amino-1,1-di(4-n-butoxy-3,5-di-tert-butylphenyl)-3-phenyl-1-propanol and copper, a complex of optically active N-(5-nitrosalicylidene)-2-amino-1,1-di(4-n-butoxy-3,5-di-tert-butylphenyl)-1-butanol and copper, a complex of optically active N-(5-nitrosalicylidene)-2-amino-1,1-di(4-n-butoxy-3,5-di-tert-butylphenyl)-3-methyl-1-butanol and copper, a complex of optically active N-(5-nitrosalicylidene)-2-amino-1,1-di(4-n-butoxy-3,5-di-tert-butylphenyl)-4-methyl-1-pentanol and copper, a complex of optically active N-(5-nitrosalicylidene)-2-amino-1,1-di(4-n-butoxy-3,5-di-tert-butylphenyl)-3-methyl-1-pentanol and copper, a complex of optically active N-(3-nitrosalicylidene)-2-amino-1,1-di(4-n-butoxy-3,5-di-tert-butylphenyl)-1-propanol and copper, a complex of optically active N-(3-nitrosalicylidene)-2-amino-1,1-di(4-n-butoxy-3,5-di-tert-butylphenyl)-3-phenyl-1-propanol and copper, a complex of optically active N-(3-nitrosalicylidene)-2-amino-1,1-di(4-n-butoxy-3,5-di-tert-butylphenyl)-1-butanol and copper, a complex of optically active N-(3-nitrosalicylidene)-2-amino-1,1-di(4-n-butoxy-3,5-di-tert-butylphenyl)-3-methyl-1-butanol and copper, a complex of optically active N-(3-nitrosalicylidene)-2-amino-1,1-di(4-n-butoxy-3,5-di-tert-butylphenyl)-4-methyl-1-pentanol and copper, a complex of optically active N-(3-nitrosalicylidene)-2-amino-1,1-di(4-n-butoxy-3,5-di-tert-butylphenyl)-3-methyl-1-pentanol and copper, a complex of optically active N-(3-bromo-5-nitrosalicylidene)-2-amino-1,1-di(4-n-butoxy-3,5-di-tert-butylphenyl)-1-propanol and copper, a complex of optically active N-(3-bromo-5-nitrosalicylidene)-2-amino-1,1-di(4-n-butoxy-3,5-di-tert-butylphenyl)-3-phenyl-1-propanol and copper, a complex of optically active N-(3-bromo-5-nitrosalicylidene)-2-amino-1,1-di(4-n-butoxy-3,5-di-tert-butylphenyl)-1-butanol and copper, a complex of optically active N-(3-bromo-5-nitrosalicylidene)-2-amino-1,1-di(4-n-butoxy-3,5-di-tert-butylphenyl)-3-methyl-1-butanol and copper, a complex of optically active N-(3-bromo-5-nitrosalicylidene)-2-amino-1,1-di(4-n-butoxy-3,5-di-tert-butylphenyl)-4-methyl-1-pentanol and copper, a complex of optically active N-(3-bromo-5-nitrosalicylidene)-2-amino-1,1-di(4-n-butoxy-3,5-di-tert-butylphenyl)-3-methyl-1-pentanol and copper, a complex of optically active N-(3,5-dinitrosalicylidene)-2-amino-1,1-di(4-n-butoxy-3,5-di-tert-butylphenyl)-1-propanol and copper, a complex of optically active N-(3,5-dinitrosalicylidene)-2-amino-1,1-di(4-n-butoxy-3,5-di-tert-butylphenyl)-3-phenyl-1-propanol and copper, a complex of optically active N-(3,5-dinitrosalicylidene)-2-amino-1,1-di(4-n-butoxy-3,5-di-tert-butylphenyl)-1-butanol and copper, a complex of optically active N-(3,5-dinitrosalicylidene)-2-amino-1,1-di(4-n-butoxy-3,5-di-tert-butylphenyl)-3-methyl-1-butanol and copper, a complex of optically active N-(3,5-dinitrosalicylidene)-2-amino-1,1-di(4-n-butoxy-3,5-di-tert-butylphenyl)-4-methyl-1-pentanol and copper, a complex of optically active N-(3,5-dinitrosalicylidene)-2-amino-1,1-di(4-n-butoxy-3,5-di-tert-butylphenyl)-3-methyl-1-pentanol and copper, a complex of optically active N-(3-fluorosalicylidene)-2-amino-1,1-di(4-n-butoxy-3,5-di-tert-butylphenyl)-1-propanol and copper, a complex of optically active N-(3-fluorosalicylidene)-2-amino-1,1-di(4-n-butoxy-3,5-di-tert-butylphenyl)-3-phenyl-1-propanol and copper, a complex of optically active N-(3-fluorosalicylidene)-2-amino-1,1-di(4-n-butoxy-3,5-di-tert-butylphenyl)-1-butanol and copper, a complex of optically active N-(3-fluorosalicylidene)-2-amino-1,1-di(4-n-butoxy-3,5-di-tert-butylphenyl)-3-methyl-1-butanol and copper, a complex of optically active N-(3-fluorosalicylidene)-2-amino-1,1-di(4-n-butoxy-3,5-di-tert-butylphenyl)-4-methyl-1-pentanol and copper, a complex of optically active N-(3-fluorosalicylidene)-2-amino-1,1-di(4-n-butoxy-3,5-di-tert-butylphenyl)-3-methyl-1-pentanol and copper, a complex of optically active N-(5-fluorosalicylidene)-2-amino-1,1-di(4-n-butoxy-3,5-di-tert-butylphenyl)-1-propanol and copper, a complex of optically active N-(5-fluorosalicylidene)-2-amino-1,1-di(4-n-butoxy-3,5-di-tert-butylphenyl)-3-phenyl-1-propanol and copper, a complex of optically active N-(5-fluorosalicylidene)-2-amino-1,1-di(4-n-butoxy-3,5-di-tert-butylphenyl)-1-butanol and copper, a complex of optically active N-(5-fluorosalicylidene)-2-amino-1,1-di(4-n-butoxy-3,5-di-tert-butylphenyl)-3-methyl-1-butanol and copper, a complex of optically active N-(5-fluorosalicylidene)-2-amino-1,1-di(4-n-butoxy-3,5-di-tert-butylphenyl)-4-methyl-1-pentanol and copper, a complex of optically active N-(5-fluorosalicylidene)-2-amino-1,1-di(4-n-butoxy-3,5-di-tert-butylphenyl)-3-methyl-1-pentanol and copper, a complex of optically active N-(3,5-difluorosalicylidene)-2-amino-1,1-di(4-n-butoxy-3,5-di-tert-butylphenyl)-1-propanol and copper, a complex of optically active N-(3,5-difluorosalicylidene)-2-amino-1,1-di(4-n-butoxy-3,5-di-tert-butylphenyl)-3-phenyl-1-propanol and copper, a complex of optically active N-(3,5-difluorosalicylidene)-2-amino-1,1-di(4-n-butoxy-3,5-di-tert-butylphenyl)-1-butanol and copper, a complex of optically active N-(3,5-difluorosalicylidene)-2-amino-1,1-di(4-n-butoxy-3,5-di-tert-butylphenyl)-3-methyl-1-butanol and copper, a complex of optically active N-(3,5-difluorosalicylidene)-2-amino-1,1-di(4-n-butoxy-3,5-di-tert-butylphenyl)-4-methyl-1-pentanol and copper, a complex of optically active N-(3,5-difluorosalicylidene)-2-amino-1,1-di(4-n-butoxy-3,5-di-tert-butylphenyl)-3-methyl-1-pentanol and copper, a complex of optically active N-[5-(methoxycarbonyl)salicylidene]-2-amino-1,1-di(4-n-butoxy-3,5-di-tert-butylphenyl)-1-propanol and copper, a complex of optically active N-[5-(methoxycarbonyl)salicylidene]-2-amino-1,1-di(4-n-butoxy-3,5-di-tert-butylphenyl)-3-phenyl-1-propanol and copper, a complex of optically active N-[5-(methoxycarbonyl)salicylidene]-2-amino-1,1-di(4-n-butoxy-3,5-di-tert-butylphenyl)-1-butanol and copper, a complex of optically active N-[5-(methoxycarbonyl)salicylidene]-2-amino-1,1-di(4-n-butoxy-3,5-di-tert-butylphenyl)-3-methyl-1-butanol and copper, a complex of optically active N-[5-(methoxycarbonyl)salicylidene]-2-amino-1,1-di(4-n-butoxy-3,5-di-tert-butylphenyl)-4-methyl-1-pentanol and copper, a complex of optically active N-[5-(methoxycarbonyl)salicylidene]-2-amino-1,1-di(4-n-butoxy-3,5-di-tert-butylphenyl)-3-methyl-1-pentanol and copper, a complex of optically active N-(5-trifluoromethylsalicylidene)-2-amino-1,1-di(4-n-butoxy-3,5-di-tert-butylphenyl)-1-propanol and copper, a complex of optically active N-(5-trifluoromethylsalicylidene)-2-amino-1,1-di(4-n-butoxy-3,5-di-tert-butylphenyl)-3-phenyl-1-propanol and copper, a complex of optically active N-(5-trifluoromethylsalicylidene)-2-amino-1,1-di(4-n-butoxy-3,5-di-tert-butylphenyl)-1-butanol and copper, a complex of optically active N-(5-trifluoromethylsalicylidene)-2-amino-1,1-di(4-n-butoxy-3,5-di-tert-butylphenyl)-3-methyl-1-butanol and copper, a complex of optically active N-(5-trifluoromethylsalicylidene)-2-amino-1,1-di(4-n-butoxy-3,5-di-tert-butylphenyl)-4-methyl-1-pentanol and copper, a complex of optically active N-(5-trifluoromethylsalicylidene)-2-amino-1,1-di(4-n-butoxy-3,5-di-tert-butylphenyl)-3-methyl-1-pentanol and copper, a complex of optically active N-(5-cyanosalicylidene)-2-amino-1,1-di(4-n-butoxy-3,5-di-tert-butylphenyl)-1-propanol and copper, a complex of optically active N-(5-cyanosalicylidene)-2-amino-1,1-di(4-n-butoxy-3,5-di-tert-butylphenyl)-3-phenyl-1-propanol and copper, a complex of optically active N-(5-cyanosalicylidene)-2-amino-1,1-di(4-n-butoxy-3,5-di-tert-butylphenyl)-1-butanol and copper, a complex of optically active N-(5-cyanosalicylidene)-2-amino-1,1-di(4-n-butoxy-3,5-di-tert-butylphenyl)-3-methyl-1-butanol and copper, a complex of optically active N-(5-cyanosalicylidene)-2-amino-1,1-di(4-n-butoxy-3,5-di-tert-butylphenyl)-4-methyl-1-pentanol and copper, a complex of optically active N-(5-cyanosalicylidene)-2-amino-1,1-di(4-n-butoxy-3,5-di-tert-butylphenyl)-3-methyl-1-pentanol and copper, a complex of optically active N-(5-nitrosalicylidene)-2-amino-1,1-di(4-n-octyloxy-3,5-di-tert-butylphenyl)-1-propanol and copper, a complex of optically active N-(5-nitrosalicylidene)-2-amino-1,1-di(4-n-octyloxy-3,5-di-tert-butylphenyl)-3-phenyl-1-propanol and copper, a complex of optically active N-(5-nitrosalicylidene)-2-amino-1,1-di(4-n-octyloxy-3,5-di-tert-butylphenyl)-1-butanol and copper, a complex of optically active N-(5-nitrosalicylidene)-2-amino-1,1-di(4-n-octyloxy-3,5-di-tert-butylphenyl)-3-methyl-1-butanol and copper, a complex of optically active N-(5-nitrosalicylidene)-2-amino-1,1-di(4-n-octyloxy-3,5-di-tert-butylphenyl)-4-methyl-1-pentanol and copper, a complex of optically active N-(5-nitrosalicylidene)-2-amino-1,1-di(4-n-octyloxy-3,5-di-tert-butylphenyl)-3-methyl-1-pentanol and copper, a complex of optically active N-(3-nitrosalicylidene)-2-amino-1,1-di(4-n-octyloxy-3,5-di-tert-butylphenyl)-1-propanol and copper, a complex of optically active N-(3-nitrosalicylidene)-2-amino-1,1-di(4-n-octyloxy-3,5-di-tert-butylphenyl)-3-phenyl-1-propanol and copper, a complex of optically active N-(3-nitrosalicylidene)-2-amino-1,1-di(4-n-octyloxy-3,5-di-tert-butylphenyl)-1-butanol and copper, a complex of optically active N-(3-nitrosalicylidene)-2-amino-1,1-di(4-n-octyloxy-3,5-di-tert-butylphenyl)-3-methyl-1-butanol and copper, a complex of optically active N-(3-nitrosalicylidene)-2-amino-1,1-di(4-n-octyloxy-3,5-di-tert-butylphenyl)-4-methyl-1-pentanol and copper, a complex of optically active N-(3-nitrosalicylidene)-2-amino-1,1-di(4-n-octyloxy-3,5-di-tert-butylphenyl)-3-methyl-1-pentanol and copper, a complex of optically active N-(3-bromo-5-nitrosalicylidene)-2-amino-1,1-di(4-n-octyloxy-3,5-di-tert-butylphenyl)-1-propanol and copper, a complex of optically active N-(3-bromo-5-nitrosalicylidene)-2-amino-1,1-di(4-n-octyloxy-3,5-di-tert-butylphenyl)-3-phenyl-1-propanol and copper, a complex of optically active N-(3-bromo-5-nitrosalicylidene)-2-amino-1,1-di(4-n-octyloxy-3,5-di-tert-butylphenyl)-1-butanol and copper, a complex of optically active N-(3-bromo-5-nitrosalicylidene)-2-amino-1,1-di(4-n-octyloxy-3,5-di-tert-butylphenyl)-3-methyl-1-butanol and copper, a complex of optically active N-(3-bromo-5-nitrosalicylidene)-2-amino-1,1-di(4-n-octyloxy-3,5-di-tert-butylphenyl)-4-methyl-1-pentanol and copper, a complex of optically active N-(3-bromo-5-nitrosalicylidene)-2-amino-1,1-di(4-n-octyloxy-3,5-di-tert-butylphenyl)-3-methyl-1-pentanol and copper, a complex of optically active N-(3,5-dinitrosalicylidene)-2-amino-1,1-di(4-n-octyloxy-3,5-di-tert-butylphenyl)-1-propanol and copper, a complex of optically active N-(3,5-dinitrosalicylidene)-2-amino-1,1-di(4-n-octyloxy-3,5-di-tert-butylphenyl)-3-phenyl-1-propanol and copper, a complex of optically active N-(3,5-dinitrosalicylidene)-2-amino-1,1-di(4-n-octyloxy-3,5-di-tert-butylphenyl)-1-butanol and copper, a complex of optically active N-(3,5-dinitrosalicylidene)-2-amino-1,1-di(4-n-octyloxy-3,5-di-tert-butylphenyl)-3-methyl-1-butanol and copper, a complex of optically active N-(3,5-dinitrosalicylidene)-2-amino-1,1-di(4-n-octyloxy-3,5-di-tert-butylphenyl)-4-methyl-1-pentanol and copper, a complex of optically active N-(3,5-dinitrosalicylidene)-2-amino-1,1-di(4-n-octyloxy-3,5-di-tert-butylphenyl)-3-methyl-1-pentanol and copper, a complex of optically active N-(3-fluorosalicylidene)-2-amino-1,1-di(4-n-octyloxy-3,5-di-tert-butylphenyl)-1-propanol and copper, a complex of optically active N-(3-fluorosalicylidene)-2-amino-1,1-di(4-n-octyloxy-3,5-di-tert-butylphenyl)-3-phenyl-1-propanol and copper, a complex of optically active N-(3-fluorosalicylidene)-2-amino-1,1-di(4-n-octyloxy-3,5-di-tert-butylphenyl)-1-butanol and copper, a complex of optically active N-(3-fluorosalicylidene)-2-amino-1,1-di(4-n-octyloxy-3,5-di-tert-butylphenyl)-3-methyl-1-butanol and copper, a complex of optically active N-(3-fluorosalicylidene)-2-amino-1,1-di(4-n-octyloxy-3,5-di-tert-butylphenyl)-4-methyl-1-pentanol and copper, a complex of optically active N-(3-fluorosalicylidene)-2-amino-1,1-di(4-n-octyloxy-3,5-di-tert-butylphenyl)-3-methyl-1-pentanol and copper, a complex of optically active N-(5-fluorosalicylidene)-2-amino-1,1-di(4-n-octyloxy-3,5-di-tert-butylphenyl)-1-propanol and copper, a complex of optically active N-(5-fluorosalicylidene)-2-amino-1,1-di(4-n-octyloxy-3,5-di-tert-butylphenyl)-3-phenyl-1-propanol and copper, a complex of optically active N-(5-fluorosalicylidene)-2-amino-1,1-di(4-n-octyloxy-3,5-di-tert-butylphenyl)-1-butanol and copper, a complex of optically active N-(5-fluorosalicylidene)-2-amino-1,1-di(4-n-octyloxy-3,5-di-tert-butylphenyl)-3-methyl-1-butanol and copper, a complex of optically active
N-(5-fluorosalicylidene)-2-amino-1,1-di(4-n-octyloxy-3,5-di-tert-butylphenyl)-4-methyl-1-pentanol and copper, a complex of optically active
N-(5-fluorosalicylidene)-2-amino-1,1-di(4-n-octyloxy-3,5-di-tert-butylphenyl)-3-methyl-1-pentanol and copper, a complex of optically active
N-(3,5-difluorosalicylidene)-2-amino-1,1-di(4-n-octyloxy-3,5-di-tert-butylphenyl)-1-propanol and copper, a complex of optically active
N-(3,5-difluorosalicylidene)-2-amino-1,1-di(4-n-octyloxy-3,5-di-tert-butylphenyl)-3-phenyl-1-propanol and copper, a complex of optically active
N-(3,5-difluorosalicylidene)-2-amino-1,1-di(4-n-octyloxy-3,5-di-tert-butylphenyl)-1-butanol and copper, a complex of optically active
N-(3,5-difluorosalicylidene)-2-amino-1,1-di(4-n-octyloxy-3,5-di-tert-butylphenyl)-3-methyl-1-butanol and copper, a complex of optically active
N-(3,5-difluorosalicylidene)-2-amino-1,1-di(4-n-octyloxy-3,5-di-tert-butylphenyl)-4-methyl-1-pentanol and copper, a complex of optically active
N-(3,5-difluorosalicylidene)-2-amino-1,1-di(4-methoxy-3,5-di-tert-butylphenyl)-3-methyl-1-pentanol and copper, a complex of optically active
N-[5-(methoxycarbonyl)salicylidene]-2-amino-1,1-di(4-n-octyloxy-3,5-di-tert-butylphenyl)-1-propanol and copper, a complex of optically active
N-[5-(methoxycarbonyl)salicylidene]-2-amino-1,1-di(4-n-octyloxy-3,5-di-tert-butylphenyl)-3-phenyl-1-propanol and copper, a complex of optically active
N-[5-(methoxycarbonyl)salicylidene]-2-amino-1,1-di(4-n-octyloxy-3,5-di-tert-butylphenyl)-1-butanol and copper, a complex of optically active
N-[5-(methoxycarbonyl)salicylidene]-2-amino-1,1-di(4-n-octyloxy-3,5-di-tert-butylphenyl)-3-methyl-1-butanol and copper, a complex of optically active
N-[5-(methoxycarbonyl)salicylidene]-2-amino-1,1-di(4-n-octyloxy-3,5-di-tert-butylphenyl)-4-methyl-1-pentanol and copper, a complex of optically active
N-[5-(methoxycarbonyl)salicylidene]-2-amino-1,1-di(4-n-octyloxy-3,5-di-tert-butylphenyl)-3-methyl-1-pentanol and copper, a complex of optically active
N-(5-trifluoromethylsalicylidene)-2-amino-1,1-di(4-n-octyloxy-3,5-di-tert-butylphenyl)-1-propanol and copper, a complex of optically active
N-(5-trifluoromethylsalicylidene)-2-amino-1,1-di(4-n-octyloxy-3,5-di-tert-butylphenyl)-3-phenyl-1-propanol and copper, a complex of optically active
N-(5-trifluoromethylsalicylidene)-2-amino-1,1-di(4-n-octyloxy-3,5-di-tert-butylphenyl)-1-butanol and copper, a complex of optically active
N-(5-trifluoromethylsalicylidene)-2-amino-1,1-di(4-n-octyloxy-3,5-di-tert-butylphenyl)-3-methyl-1-butanol and copper, a complex of optically active
N-(5-trifluoromethylsalicylidene)-2-amino-1,1-di(4-n-octyloxy-3,5-di-tert-butylphenyl)-4-methyl-1-pentanol and copper, a complex of optically active
N-(5-trifluoromethylsalicylidene)-2-amino-1,1-di(4-n-octyloxy-3,5-di-tert-butylphenyl)-3-methyl-1-pentanol and copper, a complex of optically active
N-(5-cyanosalicylidene)-2-amino-1,1-di(4-n-octyloxy-3,5-di-tert-butylphenyl)-1-propanol and copper, a complex of optically active
N-(5-cyanosalicylidene)-2-amino-1,1-di(4-n-octyloxy-3,5-di-tert-butylphenyl)-3-phenyl-1-propanol and copper, a complex of optically active
N-(5-cyanosalicylidene)-2-amino-1,1-di(4-n-octyloxy-3,5-di-tert-butylphenyl)-1-butanol and copper, a complex of optically active
N-(5-cyanosalicylidene)-2-amino-1,1-di(4-n-octyloxy-3,5-di-tert-butylphenyl)-3-methyl-1-butanol and copper, a complex of optically active
N-(5-cyanosalicylidene)-2-amino-1,1-di(4-n-octyloxy-3,5-di-tert-butylphenyl)-4-methyl-1-pentanol and copper, and a complex of optically active
N-(5-cyanosalicylidene)-2-amino-1,1-di(4-n-octyloxy-3,5-di-tert-butylphenyl)-3-methyl-1-pentanol and copper.

Subsequently, a process for producing an optically active cyclopropanecarboxylic acid ester compound represented by the formula (4):

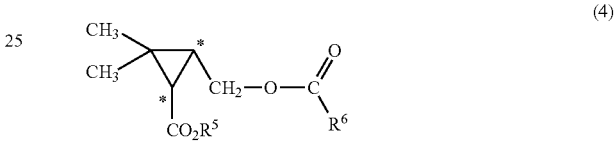

(wherein $R^5$, $R^6$ and * each represents the same meaning as defined above)

(hereinafter, abbreviated as optically active cyclopropanecarboxylic acid ester (4)) by reacting the diazoacetic acid ester (2) and the compound (3) in the presence of the above-obtained asymmetric copper complex will be described.

In the formula (2), $R^5$ represents an alkyl group having 1 to 15 carbon atoms or an aryl group having 6 to 10 carbon atoms. Examples of the alkyl group having 1 to 15 carbon atoms include a methyl group, an ethyl group, a n-propyl group, an isopropyl group, a n-butyl group, an isobutyl group, a sec-butyl group, a tert-butyl group, a n-hexyl group, a n-octyl group, a cyclohexyl group, a menthyl group and a dicyclohexylmethyl group. Examples of the aryl group having 6 to 10 carbon atoms include a phenyl group and a naphthyl group. $R^5$ is preferably an alkyl group having 1 to 15 carbon atoms, more preferably an alkyl group having 1 to 10 carbon atoms, particularly preferably an alkyl group having 1 to 6 carbon atoms.

Examples of the diazoacetic acid ester (2) include methyl diazoacetate, ethyl diazoacetate, n-propyl diazoacetate, isopropyl diazoacetate, n-butyl diazoacetate, tert-butyl diazoacetate, cyclohexyl diazoacetate and menthyl diazoacetate. Such a diazoacetic acid ester (2) can be prepared, for example, by reacting a corresponding amino acid ester and a diazotizing agent such as sodium nitrite.

In the formula (3), $R^6$ represents an alkyl group having 1 to 15 carbon atoms, an aryl group having 6 to 10 carbon atoms or an aralkyl group having 7 to 20 carbon atoms, and examples of each of them include the same groups as those described above.

Examples of the compound (3) include
1-acetoxy-3-methyl-2-butene,
1-propionyloxy-3-methyl-2-butene,
1-butyryloxy-3-methyl-2-butene,
1-isopropylcarbonyloxy-3-methyl-2-butene, 1-benzylcarbonyloxy-3-methyl-2-butene,
1-benzoyloxy-3-methyl-2-butene and
1-tritylcarbonyloxy-3-methyl-2-butene.

Such a compound (3) can be produced, for example, by reacting 3-methyl-2-butene-1-ol and corresponding carboxylic acid halide or a carboxylic acid anhydride in the presence of a base (see e.g. JP-A No. 2006-45190).

The amount of the compound (3) used is usually 1 mole or more based on 1 mole of the diazoacetic acid ester (2), and there is no upper limit and, when the compound (3) is liquid under the reacting condition, the compound (3) may be used as a solvent.

The amount of the asymmetric copper complex used is usually 0.01 to 10% by mole in terms of copper, based on 1 mole of the diazoacetic acid ester (2).

The reaction between the diazoacetic acid ester (2) and the compound (3) is usually performed by mixing the asymmetric copper complex, the diazoacetic acid ester (2) and the compound (3). Preferably, the reaction is performed by a method of adding the diazoacetic acid ester (2) to a mixture of the asymmetric copper complex and the compound (3), or a method of adding the compound (3) and the diazoacetic acid ester (2) to the asymmetric copper complex. The compound (3) and the diazoacetic acid ester (2) may be added continuously or intermittently. The diazoacetic acid ester (2) is added over usually 1 to 100 hours, preferably 4 to 70 hours, more preferably 8 to 50 hours.

The reaction between the diazoacetic acid ester (2) and the compound (3) may be performed under normal pressure, or under pressure.

The reaction temperature is usually −20° C. to 150° C.

The reaction may be performed in the co-presence of a reducing agent such as phenylhydrazine. The reducing agent may be added at preparation of the asymmetric copper complex. The amount of the reducing agent used is usually 0.9 to 1.3 moles based on 1 mole of the copper compound.

The reaction between the diazoacetic acid ester (2) and the compound (3) may be performed in the co-presence of a Lewis acid and, by performing the reaction in the presence of a Lewis acid, there is a tendency that the yield of the optically active cyclopropanecarboxylic acid ester (4) is improved.

Examples of the Lewis acid include a metal alkoxide having Lewis acidity and boron compounds having Lewis acidity such as a boron trifluoride-diethyl ether complex, triethylborane, triphenylborane, triethoxyborane and triisopropoxyborane, and a metal alkoxide having Lewis acidity is preferable. Examples of the metal alkoxide having Lewis acidity include aluminum trialkoxides such as aluminum triethoxide, titanium tetraalkoxides such as titanium tetraisopropoxide, and zirconium tetraalkoxides such as zirconium tetra(n-butoxide) and zirconium tetraisopropoxide, and aluminum triethoxide, titanium tetraisopropoxide and zirconium tetraisopropoxide are preferable. The Lewis acids may be used alone, or two or more kinds thereof may be used in combination.

The amount of the Lewis acid is usually 0.5 to 2 moles based on 1 mole of the copper compound.

The reaction between the diazoacetic acid ester (2) and the compound (3) may be performed in the co-presence of a lithium compound, and there is a tendency that the cis form selectivity of the optically active cyclopropanecarboxylic acid ester (4) is improved by performing the reaction in the co-presence of a lithium compound.

Examples of the lithium compound include lithium salts, the representative of which is lithium halides such as lithium chloride, lithium bromide, lithium iodide and lithium fluoride, lithium alkoxides having 1 to 4 carbon atoms such as lithium methoxide, lithium ethoxide, lithium propoxide and lithium butoxide, and lithium hydroxide. The lithium compounds may be used alone, or two or more kinds thereof may be used in combination. Among them, lithium alkoxide having 1 to 4 carbon atoms is preferable.

The amount of the lithium compound used is usually 0.5 to 2 moles based on 1 mole of the copper compound.

The reaction between the diazoacetic acid ester (2) and the compound (3) is usually performed in the presence of an organic solvent. Examples of the organic solvent include aliphatic hydrocarbons such as hexane, heptane and cyclohexane, aromatic hydrocarbons such as toluene, halogenated hydrocarbons such as dichloromethane and dichloroethane, and esters such as ethyl acetate and butyl acetate. The amount thereof used is not limited, but in view of economic efficiency and volume efficiency, actually, the amount is 100 parts by weight or less based on 1 part by weight of the diazoacetic acid ester (2).

After completion of the reaction, for example, if necessary, the reaction mixture is filtered to remove insolubles, and concentrated, and thus, the optically active cyclopropanecarboxylic acid ester (4) can be taken out. The optically active cyclopropanecarboxylic acid ester (4) taken out may be purified by a usual purification means such as distillation or column chromatography.

The resulting optically active cyclopropane carboxylic acid ester (4) is a mixture of a cis form in which a group represented by —$CO_2R^5$ and a group represented by $R^6COOCH_2$— are on the same side relative to a cyclopropane ring plane, and a trans form in which those groups are on opposite sides and, by the production process of the present invention, a mixture of a cis form and a trans form of the optically active cyclopropanecarboxylic acid ester (4) is obtained in which the cis form ratio (the ratio (%) of the cis form relative to the total of the cis form and the trans form) is usually 80% or more, preferably 85% or more.

In addition, the optical purity of the cis form of the optically active cyclopropanecarboxylic acid ester (4) is different depending on the optical purity of the optically active salicylideneaminoalcohol (1) and, for example, when the optical purity of the optically active salicylideneaminoalcohol (1) is 100% e.e., the optical purity of the cis form is usually 70% e.e. or more, preferably 80% e.e. or more.

Examples of the optically active cyclopropanecarboxylic acid ester (4) include optically active methyl 3-acetoxymethyl-2,2-dimethylcyclopropanecarboxylate, optically active methyl
3-propionyloxymethyl-2,2-dimethylcyclopropanecarboxylate, optically active methyl
3-butyryloxymethyl-2,2-dimethylcyclopropanecarboxylate, optically active methyl
3-isopropylcarbonyloxymethyl-2,2-dimethylcyclopropanecarboxylate, optically active methyl
3-benzylcarbonyloxymethyl-2,2-dimethylcyclopropanecarboxylate, optically active methyl
3-tritylcarbonyloxymethyl-2,2-dimethylcyclopropanecarboxylate, optically active methyl
3-benzoyloxymethyl-2,2-dimethylcyclopropanecarboxylate, optically active ethyl
3-acetoxymethyl-2,2-dimethylcyclopropanecarboxylate, optically active ethyl
3-propionyloxymethyl-2,2-dimethylcyclopropanecarboxylate, optically active ethyl
3-butyryloxymethyl-2,2-dimethylcyclopropanecarboxylate, optically active ethyl
3-isopropylcarbonyloxymethyl-2,2-dimethylcyclopropanecarboxylate, optically active ethyl 3-benzylcarbonyloxymethyl-2,2-dimethylcyclopropanecarboxylate, optically active ethyl
3-tritylcarbonyloxymethyl-2,2-dimethylcyclopropanecarboxylate, optically active ethyl
3-benzoyloxymethyl-2,2-dimethylcyclopropanecarboxylate, optically active tert-butyl
3-acetoxymethyl-2,2-dimethylcyclopropanecarboxylate, optically active tert-butyl
3-propionyloxymethyl-2,2-dimethylcyclopropanecarboxylate, optically active tert-butyl
3-butyryloxymethyl-2,2-dimethylcyclopropanecarboxylate, optically active tert-butyl
3-isopropylcarbonyloxymethyl-2,2-dimethylcyclopropanecarboxylate, optically active tert-butyl
3-benzylcarbonyloxymethyl-2,2-dimethylcyclopropanecarboxylate, optically active tert-butyl
3-tritylcarbonyloxymethyl-2,2-dimethylcyclopropanecarboxylate, optically active tert-butyl
3-benzoyloxymethyl-2,2-dimethylcyclopropanecarboxylate, optically active cyclohexyl
3-acetoxymethyl-2,2-dimethylcyclopropanecarboxylate, optically active cyclohexyl
3-propionyloxymethyl-2,2-dimethylcyclopropanecarboxylate, optically active cyclohexyl
3-butyryloxymethyl-2,2-dimethylcyclopropanecarboxylate, optically active cyclohexyl
3-isopropylcarbonyloxymethyl-2,2-dimethylcyclopropanecarboxylate, optically active cyclohexyl
3-benzylcarbonyloxymethyl-2,2-dimethylcyclopropanecarboxylate, optically active cyclohexyl
3-tritylcarbonyloxymethyl-2,2-dimethylcyclopropanecarboxylate, optically active cyclohexyl
3-benzoyloxymethyl-2,2-dimethylcyclopropanecarboxylate, optically active menthyl
3-acetoxymethyl-2,2-dimethylcyclopropanecarboxylate, optically active menthyl
3-propionyloxymethyl-2,2-dimethylcyclopropanecarboxylate, optically active menthyl
3-butyryloxymethyl-2,2-dimethylcyclopropanecarboxylate, optically active menthyl
3-isopropylcarbonyloxymethyl-2,2-dimethylcyclopropanecarboxylate, optically active menthyl
3-benzylcarbonyloxymethyl-2,2-dimethylcyclopropanecarboxylate, optically active menthyl
3-tritylcarbonyloxymethyl-2,2-dimethylcyclopropanecarboxylate, and optically active menthyl
3-benzoyloxymethyl-2,2-dimethylcyclopropanecarboxylate.

EXAMPLES

The present invention will be described in more detail below by way of examples, but the present invention is not limited by these examples. In the following examples, a cis form means a steric isomer in which an acetoxymethyl group and an ethoxycarbonyl group are on the same side relative to a cyclopropane ring plane, and a trans form means a steric isomer in which an acetoxymethyl group and an ethoxycarbonyl group are on opposite sides relative to a cyclopropane ring plane. A yield was calculated from the results of analysis by a gas chromatography analysis method. A cis form ratio (the ratio (%) of the cis form relative to the total of the cis form and the trans form), and an optical purity were calculated from the results of analysis by a liquid chromatography analysis method (gradient method, eluent: water/acetonitrile, detection wavelength: 210 nm) using an optically active column (two columns of CHIRALCEL OJ-RH (150 mm×4.6 mmφ) manufactured by DAICEL CHEMICAL INDUSTRIES, LTD, were serially connected).

Production Example 1 of Optically Active Aminoalcohol

A 200 mL round-bottom four-neck flask equipped with a Dimroth condenser with a nitrogen introducing tube attached thereto, a thermometer, a magnetic rotator and a dropping funnel was heated under reduced pressure, nitrogen was then introduced into the flask, pressure in the flask was returned to normal pressure, and the flask was cooled to room temperature (about 25° C.). After 0.8472 g of magnesium and a minor amount of iodine were added to the flask, a small amount of a solution obtained by mixing 10.00 g of 3,5-di-tert-butylbromobenzene and 54.0 mL of dehydrated tetrahydrofuran was added dropwise. The flask was heated, and it was confirmed that the Grignard reaction was initiated. Thereafter, the remaining solution was added dropwise to the flask over 20 minutes. The resulting mixture was refluxed for 70 minutes. After the resulting reaction mixture was cooled to −10° C., 0.6206 g of L-alanine methyl ester hydrochloride was added. After the temperature of the resulting mixture was raised to room temperature, the mixture was further refluxed for 4 hours. The resulting reaction mixture was cooled to 0 to 5° C. To the reaction mixture were added dropwise 30 mL of an aqueous saturated ammonium chloride solution, and further 10 mL of water. The resulting mixture was stirred at 20° C. for 30 minutes. The resulting mixture was extracted with 30 mL of diethyl ether three times. The resulting organic layers were mixed, and dried with anhydrous sodium sulfate. Sodium sulfate was removed by filtration, and the resulting filtrate was concentrated. The resulting residue was purified by silica gel column chromatography (ethyl acetate/hexane=2/98~40/60) to obtain 0.6015 g of a white crystal of (S)-2-amino-1,1-di(3,5-di-tert-butylphenyl)-1-propanol.

$^1$H-NMR (300 MHz, CDCl$_3$, tetramethylsilane (TMS) standard)
δ (ppm): 7.53 (2H, d), 7.40 (2H, d), 7.28 to 7.22 (2H, m), 4.14 (1H, m), 4.03 (1H, brs), 1.36 (2H, s), 1.34 (1H, s), 1.32 (18H, s), 0.96 (3H, d)
$^{13}$C-NMR (75 MHz, CDCl$_3$, TMS standard)
δ (ppm): 150.93, 150.43, 146.71, 144.56, 121.03, 120.80, 120.60, 80.07, 53.59, 35.65, 35.58, 32.30, 32.26, 17.93

Production Example 1 of Optically Active Salicylideneaminoalcohol Compound

To a 50 mL round-bottom flask were added 0.570 g of (S)-2-amino-1,1-di(3,5-di-tert-butylphenyl)-1-propanol, 0.226 g of 5-nitrosalicylaldehyde and 4.9 mL of toluene. The resulting mixture was stirred at 80° C. for 1 hour. The resulting mixture was cooled to room temperature, and then concentrated under reduced pressure. To the resulting residue were added 5 mL of n-heptane and 0.5 mL of ethyl acetate, and the mixture was heated to 80° C. The resulting solution was cooled to 20° C., and the precipitated crystal was taken out by filtration. The crystal taken out was dried under reduced pressure to obtain 0.6403 g of a yellow crystal of (S)—N-(5-nitrosalicylidene)-2-amino-1,1-di(3,5-di-tert-butylphenyl)-1-propanol.

$^1$H-NMR (300 MHz, CDCl$_3$, TMS standard)
δ (ppm): 14.60 (1H, brs), 8.12 to 8.08 (1H, m), 7.98 (1H, d), 7.86 (1H, s), 7.36 (3H, s), 7.28 to 7.25 (3H, m), 6.76 (1H, d), 4.53 (1H, m), 3.06 (1H, s), 1.44 (3H, d), 1.33 (18H, s), 1.22 (18H, s)

$^{13}$C-NMR (75 MHz, CDCl$_3$, TMS standard)

δ (ppm): 173.55, 164.40, 151.24, 151.16, 143.65, 142.79, 137.90, 130.17, 129.47, 121.99, 121.88, 121.48, 121.31, 115.94, 81.57, 69.80, 35.68, 35.62, 32.21, 32.11, 17.14

Production Example 1 of Asymmetric Copper Complex

To a 100 mL four-neck flask substituted with nitrogen were added 0.4986 g of (S)—N-(5-nitrosalicylidene)-2-amino-1,1-di(3,5-di-tert-butylphenyl)-1-propanol, 0.1607 g of a copper (II) acetate monohydrate and 32.1 mL of toluene. The resulting mixture was stirred at 80° C. for 1 hour. After the resulting mixture was cooled to room temperature, 0.324 mL of a methanol solution of sodium methylate (sodium methylate content: 28% by weight) was added. The resulting mixture was stirred at room temperature for 30 minutes. The resulting reaction mixture was washed with 9.6 mL of water, and then dried with anhydrous sodium sulfate. After sodium sulfate was removed by filtration, the resulting filtrate was concentrated under reduced pressure. The resulting residue was dissolved in 1 mL of toluene at 80° C., and 6.0 mL of n-heptane was added dropwise to the resulting solution. The resulting mixture was cooled to 10° C., and the precipitated crystal was taken out by filtration. The crystal taken out was washed with 1.5 mL of n-heptane, and then dried under reduced pressure to obtain 0.4913 g of a deep green crystal of a complex of (S)—N-(5-nitrosalicylidene)-2-amino-1,1-di(3,5-di-tert-butylphenyl)-1-propanol and copper.

MS spectrum (FD-MS) m/z: 1325 (100.0%), 1324 (95.1%), 1326 (82.6%), 1323 (66.1%), 1322 (61.6%), 1327 (53.8%), 1329 (15.6%), 1321 (13.7%), 1320 (13.4), 1318 (10.0), 1318 (6.2), 1330 (5.0)

Calculated value of the molecular weight of the copper complex (binuclear complex): 1324.74

Example 1

To a 25 mL Schlenk tube substituted with nitrogen were added 69.7 mg of the complex of (S)—N-(5-nitrosalicylidene)-2-amino-1,1-di(3,5-di-tert-butylphenyl)-1-propanol and copper obtained in Production Example 1 of asymmetric copper complex, 3.8 mL of 1-acetoxy-3-methyl-2-butene and 11.8 μL of phenylhydrazine. The resulting mixture was adjusted to 10° C., and a solution obtained by mixing 1.14 g of ethyl diazoacetate and 1.8 mL of 1-acetoxy-3-methyl-2-butene was added dropwise over 4.6 hours. The resulting mixture was stirred at 10° C. for 30 minutes to obtain a solution containing optically active ethyl 3-acetoxymethyl-2,2-dimethylcyclopropanecarboxylate.

Yield: 80.8%, cis form ratio: 83.5%, optical purity of cis form: 94.7% e.e.

Production Example 2 of Optically Active Aminoalcohol

A 200 mL round-bottom four-neck flask equipped with a Dimroth condenser with a nitrogen introducing tube attached thereto, a thermometer, a magnetic rotator and a dropping funnel was heated under reduced pressure, nitrogen was then introduced into the flask, pressure in the flask was returned to normal pressure, and the flask was cooled to room temperature. After 1.27 g of magnesium and a minor amount of iodine were added to the flask, a small amount of a solution obtained by mixing 15.00 g of 3,5-di-tert-butylbromobenzene and 75.0 mL of dehydrated tetrahydrofuran was added dropwise. The flask was heated, and it was confirmed that the Grignard reaction was initiated. Thereafter, the remaining solution was added dropwise to the flask over 30 minutes. The resulting mixture was refluxed for 1.5 hours. After the resulting reaction mixture was cooled to −10° C., 1.11 g of L-valine methyl ester hydrochloride was added. After the temperature of the resulting mixture was raised to room temperature, the mixture was further refluxed for 4 hours. The resulting reaction mixture was cooled to 0 to 5° C. To the reaction solution were added dropwise 45.0 mL of an aqueous saturated ammonium chloride solution, and further 15.0 mL of water. The resulting mixture was stirred at 20° C. for 30 minutes. The resulting mixture was extracted with 45.0 mL of diethyl ether three times. The resulting organic layers were mixed, and dried with anhydrous sodium sulfate. After sodium sulfate was removed by filtration, the resulting filtrate was concentrated. The resulting residue was purified by silica gel column chromatography (ethyl acetate/hexane=2/98~40/60) to obtain 1.02 g of a colorless crystal of (S)-2-amino-1,1-di(3,5-di-tert-butylphenyl)-3-methyl-1-butanol.

$^1$H-NMR (300 MHz, CDCl$_3$, TMS standard)

δ (ppm): 7.54 (2H, d), 7.43 (2H, d), 7.28 to 7.24 (2H, m), 4.23 (1H, brs), 3.80 (1H, d), 1.77 (1H, m), 1.35 (18H, s), 1.33 (18H, s), 1.32 (2H, s), 0.96 (3H, d), 0.87 (3H, d)

$^{13}$C-NMR (75 MHz, CDCl$_3$, TMS standard)

δ (ppm): 150.86, 150.43, 147.46, 144.67, 121.01, 120.80, 120.76, 120.38, 81.24, 62.12, 35.67, 35.61, 32.33, 32.27, 28.60, 23.88, 17.09

Production Examples 2 of Optically Active Salicylideneaminoalcohol Compound

To a 50 mL round-bottom flask were added 0.9680 g of (S)-2-amino-1,1-di(3,5-di-tert-butylphenyl)-3-methyl-1-butanol, 0.3316 g of 5-nitrosalicylaldehyde and 4.8 mL of toluene. The resulting mixture was stirred at 80° C. for 1 hour. The resulting mixture was cooled to room temperature, and then concentrated under reduced pressure. To the resulting residue were added 8.0 mL of n-heptane and 1.5 mL of ethyl acetate, and the mixture was heated to 80° C. The resulting solution was cooled to 20° C., and the precipitated crystal was taken out by filtration. The crystal taken out was dried under reduced pressure to obtain 1.0829 g of a yellow crystal of (S)—N-(5-nitrosalicylidene)-2-amino-1,1-di(3,5-di-tert-butylphenyl)-3-methyl-1-butanol.

$^1$H-NMR (300 MHz, CDCl$_3$, TMS standard)

δ (ppm): 14.94 (1H, brs), 8.14 to 8.10 (1H, m), 7.98 (1H, d), 7.74 (1H, d), 7.39 (3H, s), 7.28 to 7.22 (3H, m), 6.82 (1H, d), 3.98 (1H, d), 2.82 (1H, s), 2.29 (1H, m), 1.36 (18H, s), 1.20 (18H, s), 1.05 (3H, d), 0.96 (3H, d)

$^{13}$C-NMR (75 MHz, CDCl$_3$, TMS standard)

δ (ppm): 174.50, 165.71, 151.31, 144.13, 143.17, 137.63, 130.29, 129.64, 121.95, 121.81, 121.18, 121.04, 115.70, 82.83, 80.07, 35.73, 35.62, 32.24, 32.10, 29.56, 23.42, 18.94

Production Example 2 of Asymmetric Copper Complex

To a 100 mL four-neck flask substituted with nitrogen were added 0.8001 g of (S)—N-(5-nitrosalicylidene)-2-amino-1,1-di(3,5-di-tert-butylphenyl)-3-methyl-1-butanol, 0.2490 g of a copper (II) acetate monohydrate and 50.0 mL of toluene. The resulting mixture was stirred at 80° C. for 1 hour. After the resulting mixture was cooled to room temperature, 0.50 mL of a methanol solution of sodium methylate (sodium methylate content: 28% by weight) was added. The resulting mixture was stirred at room temperature for 30 minutes. The resulting reaction mixture was washed with 14.9 mL of water, and then dried with anhydrous sodium sulfate. After sodium sulfate was removed by filtration, the resulting filtrate was concentrated under reduced pressure. The resulting residue was dissolved in 3.0 mL of toluene at 80° C. To the resulting solution was added dropwise 10.0 mL of n-heptane. The resulting mixture was cooled to 20° C., and the precipitated crystal was taken out by filtration. The crystal taken out was washed with a mixed solution of 0.5 mL of toluene and 1.5 mL of n-heptane, and then dried under reduced pressure to obtain 0.7544 g of a deep green crystal of a complex of (S)—N-(5-nitrosalicylidene)-2-amino-1,1-di(3,5-di-tert-butylphenyl)-3-methyl-1-butanol and copper.

MS spectrum (FD-MS) m/z; 1381 (100.0%), 1380 (99.1%), 1382 (84.3%), 1383 (64.7%), 1379 (57.4%), 1384 (49.9%), 1385 (25.0%), 1386 (3.5%)

Calculated value of the molecular weight of the copper complex (binuclear complex): 1380.85

Example 2

According to the same manner as in Example 1 except that 72.8 mg of the complex of (S)—N-(5-nitrosalicylidene)-2-amino-1,1-di(3,5-di-tert-butylphenyl)-3-methyl-1-butanol and copper obtained in Production Example 2 of asymmetric copper complex was used in place of 69.7 mg of the complex of (S)—N-(5-nitrosalicylidene)-2-amino-1,1-di(3,5-di-tert-butylphenyl)-1-propanol and copper in Example 1, a solution containing optically active ethyl 3-acetoxymethyl-2,2-dimethylcyclopropanecarboxylate was obtained.

Yield: 67.1%, cis form ratio: 90.6%, optical purity of cis form: 96.7% e.e.

Reference Example 1

To a 50 mL round-bottom four-neck flask equipped with a Dimroth condenser with a nitrogen introducing tube attached thereto, a thermometer, a magnetic rotator and a dropping funnel were added 4.89 g of (S)-2-aminobutyric acid and 15.0 mL of methanol. To the resulting mixture was added dropwise 6.77 g of thionyl chloride at 35° C. over 1 hour. The resulting mixture was stirred for 3 hours. The resulting reaction mixture was concentrated under reduced pressure, and 17.0 mL of toluene was added to the resulting residue at room temperature. The precipitated crystal was taken out by filtration. The crystal taken out was washed with 10.0 mL of diethyl ether, and dried under reduced pressure to obtain 7.12 g of a gray powder of (S)-2-aminobutyric acid methyl ester chloride.

$^1$H-NMR (300 MHz, CD$_3$OD, TMS standard)

δ (ppm): 4.89 (3H, s), 4.05 (1H, t), 3.86 (3H, s), 1.99 (2H, m), 1.06 (3H, t)

$^{13}$C-NMR (75 MHz, CD$_3$OD, TMS standard)

δ (ppm): 170.22, 54.39, 52.90, 24.11, 8.84

Production Example 3 of Optically Active Aminoalcohol

According to the same manner as in Production Example 2 of optically active amino alcohol except that the amount of magnesium used was 1.40 g and, 1.06 g of the (S)-2-aminobutyrid acid methyl ester hydrochloride obtained in Reference Example 1 was used in place of 1.11 g of L-valine methyl ester hydrochloride in Production Example 2 of optically active aminoalcohol, 1.71 g of a white crystal of (S)-2-amino-1,1-di(3,5-di-tert-butylphenyl)-1-butanol was obtained.

$^1$H-NMR (300 MHz, CDCl$_3$, TMS standard)

δ (ppm): 7.50 (2H, d), 7.38 (2H, d), 7.28 to 7.22 (2H, m), 4.12 (1H, brs), 3.79 to 3.75 (1H, m), 1.42 (2H, m), 1.34 (18H, s), 1.33 (2H, s), 1.29 (18H, s)

$^{13}$C-NMR (75 MHz, CDCl$_3$, TMS standard)

δ (ppm): 150.91, 150.43, 146.76, 144.44, 121.01, 120.82, 120.74, 120.53, 80.60, 60.30, 35.65, 35.58, 32.30, 32.26, 24.51, 12.55

Production Example 3 of Optically Active Salicylideneaminoalcohol Compound

To a 50 mL round-bottom flask were added 1.62 g of (S)-2-amino-1,1-di(3,5-di-tert-butylphenyl)-1-butanol, 0.5755 g of 5-nitrosalicylaldehyde and 8.1 mL of toluene. The resulting mixture was stirred at 80° C. for 1 hour. The resulting mixture was cooled to room temperature, and then concentrated under reduced pressure. To the resulting residue were added 16.0 mL of n-heptane and 3.0 mL of ethyl acetate, and the resulting mixture was heated to 80° C. The resulting solution was cooled to 20° C., and the precipitated crystal was taken out by filtration. The crystal taken out was dried under reduced pressure to obtain 1.22 g of a yellow crystal of (S)—N-(5-nitrosalicylidene)-2-amino-1,1-di(3,5-di-tert-butylphenyl)-1-butanol.

$^1$H-NMR (300 MHz, CDCl$_3$, TMS standard)

δ (ppm): 14.57 (1H, brs), 8.11 to 8.06 (1H, m), 7.95 (1H, d), 7.76 (1H, s), 7.34 to 7.21 (6H, m), 6.77 (1H, d), 4.00 (1H, d), 3.06 (1H, s), 1.85 (2H, m), 1.31 (18H, s), 1.20 (18H, s), 0.92 (3H, t)

$^{13}$C-NMR (75 MHz, CDCl$_3$, TMS standard)

δ (ppm): 173.89, 165.40, 151.28, 151.21, 143.77, 142.97, 137.82, 130.22, 129.53, 122.00, 121.85, 121.58, 121.33, 121.19, 115.74, 81.82, 77.74, 35.69, 35.62, 32.22, 32.11, 24.12, 12.24

Production Example 3 of Asymmetric Copper Complex

To a 100 mL four-neck flask substituted with nitrogen were added 1.04 g of (S)—N-(5-nitrosalicylidene)-2-amino-1,1-di(3,5-di-tert-butylphenyl)-1-butanol, 0.2490 g of a copper (II) acetate monohydrate and 66.0 mL of toluene. The resulting mixture was stirred at 80° C. for 1 hour. After the resulting mixture was cooled to room temperature, 0.67 mL of a methanol solution of sodium methylate (sodium methylate content: 28% by weight) was added, and the resulting mixture was stirred at the same temperature for 30 minutes. The resulting reaction mixture was washed with 19.9 mL of water, and then dried with anhydrous sodium sulfate. After sodium sulfate was removed by filtration, the resulting filtrate was concentrated under reduced pressure. The resulting residue was dissolved in 5.0 mL of toluene at 80° C., and 14.0 mL of n-heptane was added dropwise to the resulting solution. The resulting mixture was cooled to 20° C., and the precipitated crystal was taken out by filtration. The crystal taken out was washed with a mixed solution of 0.7 mL of toluene and 2.0 mL of n-heptane, and dried under reduced pressure to obtain 1.01 g of a deep green crystal of a complex of (S)—N-(5-nitrosalicylidene)-2-amino-1,1-di(3,5-di-tert-butylphenyl)-1-butanol and copper.

MS spectrum (FD-MS) m/z: 1353 (100.0%), 1352 (85.0%), 1354 (79.7%), 1351 (76.6%), 1355 (58.0%), 1350 (38.8%), 1356 (37.0%), 1357 (17.8%), 1358 (3.0%)

Calculated value of the molecular weight of the copper complex (binuclear complex): 1352.79

Example 3

According to the same manner as in Example 1 except that 71.2 mg of the complex of (S)—N-(5-nitrosalicylidene)-2-amino-1,1-di(3,5-di-tert-butylphenyl)-1-butanol and copper obtained in Production Example 3 of asymmetric copper complex was used in place of 69.7 mg of the complex of (S)—N-(5-nitrosalicylidene)-2-amino-1,1-di(3,5-di-tert-butylphenyl)-1-propanol and copper in Example 1, a solution containing optically active ethyl 3-acetoxymethyl-2,2-dimethylcyclopropanecarboxylate was obtained.

Yield: 68.7%, cis form ratio: 87.1%, optical purity of cis form: 93.9% e.e.

Production Example 4 of Optically Active Aminoalcohol

According to the same manner as in Production Example 2 of optically active aminoalcohol except that the amount of magnesium used was 1.40 g, and 1.25 g of L-leucine methyl ester hydrochloride was used in place of 1.11 g of L-valine methyl ester hydrochloride in Production Example 2 of optically active aminoalcohol, 1.74 g of a white crystal of (S)-2-amino-1,1-di(3,5-di-tert-butylphenyl)-4-methyl-1-pentanol was obtained.

$^1$H-NMR (300 MHz, CDCl$_3$, TMS standard)

δ (ppm): 7.47 (2H, d), 7.36 (2H, d), 7.24 to 7.19 (2H, m), 3.97 (1H, brs), 3.93 (1H, t), 1.54 (1H, m), 1.30 (20H, s), 1.29 (18H, s), 1.17 (2H, m), 0.90 (3H, d), 0.86 (3H, d)

$^{13}$C-NMR (75 MHz, CDCl$_3$, TMS standard)

δ (ppm): 150.92, 150.40, 146.90, 144.30, 120.99, 120.75, 120.72, 120.55, 80, 71, 56.15, 40.74, 35.65, 35.59, 32.30, 32.27, 26.19, 24.85, 22.42

Production Example 4 of Optically Active Salicylideneaminoalcohol Compound

To a 50 mL round-bottom flask were added 1.70 g of (S)-2-amino-1,1-di(3,5-di-tert-butylphenyl)-4-methyl-1-pentanol, 0.5721 g of 5-nitrosalicylaldehyde and 8.5 mL of toluene. The resulting mixture was stirred at 80° C. for 1 hour. The resulting reaction mixture was cooled to room temperature, and then concentrated under reduced pressure. To the resulting residue were added 16.0 mL of n-heptane and 2.0 mL of ethyl acetate, and the resulting mixture was heated to 80° C. The resulting solution was cooled to 20° C., and the precipitated crystal was taken out by filtration. The crystal taken out was dried under reduced pressure to obtain 1.53 g of a yellow crystal of (S)—N-(5-nitrosalicylidene)-2-amino-1,1-di(3,5-di-tert-butylphenyl)-4-methyl-1-pentanol.

$^1$H-NMR (300 MHz, CDCl$_3$, TMS standard)

δ (ppm): 14.63 (1H, brs), 8.10 to 8.06 (1H, m), 7.93 (1H, d), 7.69 (1H, s), 7.36 to 7.32 (3H, m), 7.26 to 7.20 (3H, m), 6.75 (1H, d), 4.23 (1H, d), 2.98 (1H, s), 1.82 (1H, m), 1.55 (2H, m), 1.32 (18H, s), 1.18 (18H, s), 0.97 (3H, d), 0.87 (3H, d)

$^{13}$C-NMR (75 MHz, CDCl$_3$, TMS standard)

δ (ppm): 174.34, 165.30, 151.33, 151.16, 143.81, 142.56, 137.62, 130.38, 129.59, 122.09, 121.94, 121.79, 121.44, 121.19, 115.58, 81.95, 73.64, 39.41, 35.71, 35.63, 32.23, 32.10, 25.77, 24.54, 22.02

Production Example 4 of Asymmetric Copper Complex

To a 100 mL four-neck flask substituted with nitrogen were added 1.29 g of (S)—N-(5-nitrosalicylidene)-2-amino-1,1-di(3,5-di-tert-butylphenyl)-4-methyl-1-pentanol, 0.3932 g of a copper (II) acetate monohydrate and 78.5 mL of toluene. The resulting mixture was stirred at 80° C. for 1 hour. After the resulting mixture was cooled to room temperature, 0.79 mL of a methanol solution of sodium methylate (sodium methylate content: 28% by weight) was added. The resulting mixture was stirred at room temperature for 30 minutes. The resulting reaction mixture was washed with 23.6 mL of water, and dried with anhydrous sodium sulfate. After sodium sulfate was removed by filtration, the resulting filtrate was concentrated under reduced pressure. The resulting residue was dissolved in 4.7 mL of toluene at 80° C., and 15.7 mL of n-heptane was added dropwise to the resulting solution. The resulting mixture was cooled to 20° C., and the precipitated crystal was taken out by filtration. The crystal taken out was washed with a mixed solution of 0.8 mL of toluene and 2.4 mL of n-heptane, and dried under reduced pressure to obtain 1.29 g of a deep green crystal of a complex of (S)—N-(5-nitrosalicylidene)-2-amino-1,1-di(3,5-di-tert-butylphenyl)-4-methyl-1-pentanol and copper.

MS spectrum (FD-MS) m/z: 1409 (100.0%), 1410 (92.7%), 1411 (62.9%), 1408 (60.5%), 1412 (49.2%), 1413 (19.8%), 1407 (8.0%), 1406 (0.9%)

Calculated value of the molecular weight of the copper complex (binuclear complex): 1408.90

Example 4

According to the same manner as in Example 1 except that 74.2 mg of the complex of (S)—N-(5-nitrosalicylidene)-2-amino-1,1-di(3,5-di-tert-butylphenyl)-4-methyl-1-pentanol and copper obtained in Production Example 4 of asymmetric copper complex was used in place of 69.7 mg of the complex of (S)—N-(5-nitrosalicylidene)-2-amino-1,1-di(3,5-di-tert-butylphenyl)-1-propanol and copper in Example 1, a solution containing optically active ethyl 3-acetoxymethyl-2,2-dimethylcyclopropanecarboxylate was obtained.

Yield: 64.9%, cis form ratio; 90.2%, optical purity of cis form: 92.0% e.e.

Production Example 5 of Optically Active Aminoalcohol

According to the same manner as in Production Example 2 of optically active aminoalcohol except that the amount of magnesium used was 1.48 g, and 1.49 g of L-phenylalanine methyl ester hydrochloride was used in place of 1.1123 g of L-valine methyl ester hydrochloride, 1.18 g of a pale yellow crystal of (S)-2-amino-1,1-di(3,5-di-tert-butylphenyl)-3-phenyl-1-propanol was obtained.

$^1$H-NMR (300 MHz, CDCl$_3$, TMS standard)

δ (ppm): 7.54 to 7.52 (4H, m), 7.33 to 7.17 (7H, m), 4.33 (1H, s), 4.14 (1H, t), 2.65 to 2.64 (1H, m), 2.46 to 2.41 (1H, m), 1.33 (18H, s), 1.30 (18H, s), 1.27 (2H, s)

$^{13}$C-NMR (75 MHz, CDCl$_3$, TMS standard)

δ (ppm): 150.35, 150.03, 145.99, 143.60, 140.45, 129.18, 128.64, 126.30, 120.41, 120.01, 119.82, 119.68, 79.32, 59.60, 37.15, 34.94, 34.71, 31.60, 31.58,

Production Example 5 of Optically Active Salicylideneaminoalcohol Compound

To a 50 mL round-bottom flask were added 1.12 g of (S)-2-amino-1,1-di(3,5-di-tert-butylphenyl)-3-phenyl-1-propanol, 0.3579 g of 5-nitrosalicylaldehyde and 5.6 mL of toluene. The resulting mixture was stirred at 80° C. for 1 hour. The resulting mixture was cooled to room temperature, and then concentrated under reduced pressure. To the resulting residue were added 7.0 mL of n-heptane and 0.5 mL of ethyl acetate, and the resulting mixture was heated to 80° C. The resulting solution was cooled to 20° C., and the precipitated crystal was taken out by filtration. The crystal taken out was washed with 7.0 mL of n-heptane, and dried under reduced pressure to obtain 1.26 g of a yellow crystal of (S)—N-(5-nitrosalicylidene)-2-amino-1,1-di(3,5-di-tert-butylphenyl)-3-phenyl-1-propanol.

$^1$H-NMR (300 MHz, CDCl$_3$, TMS standard)

δ (ppm): 14.75 (1H, brs), 8.11 to 8.07 (1H, m), 7.77 (1H, d), 7.54 (2H, d), 7.44 to 7.06 (10H, m), 6.82 (1H, d), 4.32 (1H, d), 3.68 (1H, s), 3.24 to 3.02 (2H, m), 1.41 (18H, s), 1.24 (18H, s)

$^{13}$C-NMR (75 MHz, CDCl$_3$, TMS standard)

δ (ppm): 173.10, 165.38, 151.47, 151.34, 143.85, 143.08, 138.97, 138.09, 130.05, 129.89, 129.42, 127.51, 122.16, 121.88, 121.22, 121.16, 115.85, 81.59, 78.73, 38.09, 35.80, 35, 66, 32.33, 32.15

Production Example 5 of Asymmetric Copper Complex

To a 100 mL four-neck flask substituted with nitrogen were added 1.02 g of (S)—N-(5-nitrosalicylidene)-2-amino-1,1-di(3,5-di-tert-butylphenyl)-3-phenyl-1-propanol, 0.2958 g of a copper (II) acetate monohydrate and 59.2 mL of toluene. The resulting mixture was stirred at 80° C. for 1 hour. The resulting mixture was cooled to room temperature, and 0.63 mL of a methanol solution of sodium methylate (sodium methylate content: 28% by weight) was added. The resulting mixture was stirred at room temperature for 30 minutes. The resulting reaction mixture was washed with 17.7 mL of water, and then dried with anhydrous sodium sulfate. After sodium sulfate was removed by filtration, the resulting filtrate was concentrated under reduced pressure. The resulting residue was dissolved in 10.0 mL of toluene at 80° C., and 10.0 mL of n-heptane was added dropwise to the resulting solution. The resulting mixture was cooled to 20° C., and the precipitated crystal was taken out by filtration. The crystal taken out was washed with 2.0 mL of n-heptane, and dried under reduced pressure to obtain 0.9946 g of a deep green crystal of a complex of (S)—N-(5-nitrosalicylidene)-2-amino-1,1-di(3,5-di-tert-butylphenyl)-3-phenyl-1-propanol and copper.

MS spectrum (FD-MS) m/z; 1477 (100.0%), 1478 (81.6%), 1476 (46.8%), 1479 (42.2%), 1475 (27.0%), 1480 (10.4%)

Calculated value of the molecular weight of the copper complex (binuclear complex): 1476.94

Example 5

According to the same manner as in Example 1 except that 77.7 mg of the complex of (S)—N-(5-nitrosalicylidene)-2-amino-1,1-di(3,5-di-tert-butylphenyl)-3-phenyl-1-propanol and copper obtained in Production Example 5 of asymmetric copper complex was used in place of 69.7 mg of the complex of (S)—N-(5-nitrosalicylidene)-2-amino-1,1-di(3,5-di-tert-butylphenyl)-1-propanol and copper in Example 1, a solution containing optically active ethyl 3-acetoxymethyl-2,2-dimethylcyclopropanecarboxylate was obtained.

Yield: 61.9%, cis form ratio: 87.6%, optical purity of cis form: 92.9% e.e.

Production Example 6 of Optically Active Aminoalcohol

A 200 mL round-bottom four-neck flask equipped with a Dimroth condenser with a nitrogen introducing tube attached thereto, a thermometer, a magnetic rotator and a dropping funnel was heated under reduced pressure, nitrogen was then introduced into the flask, pressure in the flask was returned to normal pressure, and the flask was cooled to room temperature. After 1.12 g of magnesium and a minor amount of iodine were added to the flask, a small amount of a solution obtained by mixing 12.00 g of 3,5-di-tert-butylbromobenzene and 60.0 mL of dehydrated tetrahydrofuran was added dropwise. The flask was heated, it was conformed that the Grignard reaction was initiated. Thereafter, the remaining solution was added dropwise to the flask over 30 minutes. The resulting mixture was refluxed for 1.5 hours. After the resulting reaction mixture was cooled to −15° C., 1.00 g of L-isoleucine methyl ester hydrochloride was added. The resulting mixture was raised to room temperature and then further refluxed for 2 hours. The resulting reaction mixture was cooled to 0 to 5° C. To the reaction mixture were added dropwise 36.0 mL of an aqueous saturated ammonium chloride solution, and further 15.0 mL of water. The resulting mixture was stirred at 20° C. for 30 minutes, and extracted with 36.0 mL of diethyl ether three times. The resulting organic layers were mixed, and dried with anhydrous sodium sulfate. After sodium sulfate was removed by filtration, the resulting filtrate was concentrated. The resulting residue was purified by silica gel column chromatography (ethyl acetate/hexane=2/98~40/60) to obtain 0.5874 g of a yellow white crystal of (2S,3S)-2-amino-1,1-di(3,5-di-tert-butylphenyl)-3-methyl-1-pentanol.

$^1$H-NMR (300 MHz, CDCl$_3$, TMS standard)

δ (ppm): 7.49 (2H, d), 7.36 (2H, d), 7.25 to 7.19 (2H, m), 4.30 (1H, brs), 3.73 (1H, d), 1.73 (1H, m), 1.34 (18H, s), 1.31 (2H, brs), 1.28 (18H, s), 1.21 (2H, m), 0.89 (3H, d), 0.69 (3H, t)

$^{13}$C-NMR (75 MHz, CDCl$_3$, TMS standard)

δ (ppm): 150.83, 150.37, 147.37, 144.58, 121.07, 120.96, 120.86, 120.42, 81.34, 63.02, 35.78, 35.66, 35.58, 32.32, 32.25, 23.63, 19.72, 13.07

Production Example 6 of Optically Active Salicylideneaminoalcohol Compound

To a 50 mL round-bottom flask were added 0.5546 g of (2S, 3S)-2-amino-1,1-di(3,5-di-tert-butylphenyl)-3-methyl-1-pentanol, 0.1877 g of 5-nitrosalicylaldehyde and 2.8 mL toluene. The resulting mixture was stirred at 80° C. for 1 hour. The resulting mixture was cooled to room temperature, and then concentrated under reduced pressure. To the resulting residue were added 7.0 mL of n-heptane and 0.5 mL of ethyl acetate. The resulting mixture was heated to 80° C. The resulting solution was cooled to 20° C., and the precipitated crystal was taken out by filtration. The crystal taken out was dried under reduced pressure to obtain 0.6638 g of a yellow crystal of (2S,3S)—N-(5-nitrosalicylidene)-2-amino-1,1-di(3,5-di-tert-butylphenyl)-3-methyl-1-pentanol.

$^1$H-NMR (300 MHz, CDCl$_3$, TMS standard)

δ (ppm): 14.91 (1H, brs), 8.11 to 8.07 (1H, m), 7.96 (1H, d), 7.75 (1H, d), 7.35 to 7.33 (3H, m), 7.26 to 7.21 (3H, m), 6.78 (1H, d), 3.96 (1H, s), 2.77 (1H, s), 1.94 (1H, m), 1.32 (18H, s), 1.29 (2H, m), 1.21 (18H, s), 0.94 (3H, d), 0.78 (3H, t)

$^{13}$C-NMR (75 MHz, CDCl$_3$, TMS standard)

δ (ppm): 173.76, 164.90, 150.62, 150.55, 143.36, 142.51, 136.94, 129.58, 128.93, 121.31, 121.07, 120.60, 120.50, 114.98, 82, 18, 79.76, 35, 83, 35.02, 34.94, 31.53, 31.41, 24.76, 18.81, 12.06

Production Example 6 of Asymmetric Copper Complex

To a 100 mL four-neck flask substituted with nitrogen were added 0.5255 g of (2S,3S)—N-(5-nitrosalicylidene)-2- amino-1,1-di(3,5-di-tert-butylphenyl)-3-methyl-1-pentanol, 0.1600 g of a copper (II) acetate monohydrate and 32.0 mL of toluene. The resulting mixture was stirred at 80° C. for 1 hour. After the resulting mixture was cooled to room temperature, 0.32 mL of a methanol solution of sodium methylate (sodium methylate content: 28% by weight) was added. The resulting mixture was stirred at room temperature for 30 minutes. To the resulting reaction mixture were added 170 mL of toluene and 9.6 mL of water and, after stirring, the layers were separated into the organic layer and the aqueous layer. The organic layer was dried with anhydrous sodium sulfate. After sodium sulfate was removed by filtration, the resulting filtrate was concentrated under reduced pressure. The resulting residue was dissolved in 8.0 mL of toluene at 80° C. After 2.0 mL of n-heptane was added dropwise to the resulting solution, the resulting mixture was cooled to 20° C. The precipitated crystal was taken out by filtration. The crystal taken out was washed with a mixed solution of 1.0 mL of toluene and 0.3 mL of n-heptane, and dried under reduced pressure to obtain 0.4679 g of a deep green crystal of a complex of (2S,3S)—N-(5-nitrosalicylidene)-2-amino-1,1-di(3,5-di-tert-butylphenyl)-3-methyl-1-pentanol and copper.

MS spectrum (FD-MS) m/z: 1410 (100.0%), 1409 (94.4%), 1411 (60.1%), 1408 (59.5%), 1407 (52.6%), 1412 (19.9%), 1413 (18.5%), 1406 (10.5%)

Calculated value of the molecular weight of the copper complex (binuclear complex): 1408.90

Example 6

According the same manner as in Example 1 except that 74.8 mg of the complex of (2S,3S)—N-(5-nitrosalicylidene)-2-amino-1,1-di(3,5-di-tert-butylphenyl)-3-methyl-1-pentanol and copper obtained in Production Example 6 of asymmetric copper complex was used in place of 69.7 mg of the complex of (S)—N-(5-nitrosalicylidene)-2-amino-1,1-di(3,5-di-tert-butylphenyl)-1-propanol and copper in Example 1, a solution containing optically active ethyl 3-acetoxymethyl-2,2-dimethylcyclopropanecarboxylate was obtained.

Yield: 51.3%, cis form ratio: 90.7% optical purity of cis form: 96.8% e.e.

Example 7

To a 25 mL Schlenk tube substituted with nitrogen were added 74.8 mg of the complex of (2S,3S)—N-(5-nitrosalicylidene)-2-amino-1,1-di(3,5-di-tert-butylphenyl)-3-methyl-1-pentanol and copper obtained in Production Example 6 of asymmetric copper complex, 3.8 mL of 1-acetoxy-3-methyl-2-butene, 11.2 mL of ethyl acetate and 11.8 µL of phenylhydrazine. After the resulting mixture was adjusted at 10° C., a solution obtained by mixing 1.14 g of ethyl diazoacetate and 1.8 mL of 1-acetoxy-3-methyl-2-butene was added dropwise to the mixture over 4.6 hours. The resulting mixture was further stirred and held at 10° C. for 30 minutes to obtain a solution containing optically active ethyl 3-acetoxy methyl-2,2-dimethylcyclopropanecarboxylate.

Yield: 69.0%, cis form ratio: 92.2%, optical purity of cis form: 98.5% e.e.

Reference Example 2

To a 500 mL round-bottom four-neck flask equipped with a Dimroth condenser with a nitrogen introducing tube attached thereto, a thermometer, a magnetic rotator and a dropping funnel were added 25.25 g of 4-hydroxy-3,5-di-tert-butylbromobenzene and 250.0 mL of dehydrated dimethylformamide. The resulting mixture was cooled to −41° C., and 4.82 g of 60% by weight sodium hydride was added at −40 to −50° C. The resulting mixture was stirred at −40±2° C. for 2 hours to allow to react. To the resulting reaction mixture was added dropwise 7.60 mL of methyl iodide at the same temperature. The temperature of the resulting mixture was raised to 4° C. over 4.5 hours. The resulting reaction mixture was stirred at room temperature overnight, and poured into 500 g of ice water. The resulting mixture was extracted with 200 mL of ethyl acetate three times. The resulting organic layers were mixed, and dried with anhydrous magnesium sulfate. After magnesium sulfate was removed by filtration, the resulting filtrate was concentrated under reduced pressure. The resulting residue was purified by silica gel column chromatography (hexane) to obtain 25.30 g of a colorless crystal of 4-methoxy-3,5-di-tert-butylbromobenzene.

Purity (GC): 99.9%

GC-MS m/z: 300, 298 (calculated value of the molecular weight: 299.25)

Production Example 7 of Optically Active Aminoalcohol

A 300 mL round-bottom four-neck flask equipped with a Dimroth condenser with a nitrogen introducing tube attached thereto, a thermometer, a magnetic rotator and a dropping funnel was heated under reduced pressure, nitrogen was then introduced into the flask, pressure in the flask was returned to normal pressure, and the flask was cooled to room temperature. After 1.99 g of magnesium and a minor amount of iodine were added to the flask, a small amount of a solution obtained by mixing 25.30 g of 4-methoxy-3,5-di-tert-butylbromobenzene and 119.0 mL of dehydrated tetrahydrofuran was added dropwise. The flask was heated, and it was confirmed that the Grignard reaction was initiated. Thereafter, the remaining solution was added dropwise over 30 minutes. The resulting mixture was refluxed for 1.5 hours. After the resulting reaction mixture was cooled to −10° C., 1.45 g of L-alanine methyl ester hydrochloride was added. The temperature of the resulting mixture was raised to room temperature, and the mixture was further refluxed for 3 hours. The resulting reaction mixture was cooled to 0 to 5° C. To the reaction mixture were added dropwise 70.0 mL of an aqueous saturated ammonium chloride solution, and further 20.0 mL of water. The resulting mixture was stirred at 20° C. for 12 minutes. The resulting mixture was extracted with 70.0 mL of diethyl ether three times. The resulting organic layers were mixed, and dried with anhydrous sodium sulfate. After sodium sulfate was removed by filtration, the resulting filtrate was concentrated. The resulting residue was purified by silica gel column chromatography (ethyl acetate/hexane=2/98~30/70) to obtain 3.32 g of a pale yellow solid of (S)-2-amino-1,1-di(4-methoxy-3,5-di-tert-butylphenyl)-3-methyl-1-butanol.

$^1$H-NMR (300 MHz, CDCl$_3$, TMS standard)

δ (ppm): 7.49 (2H, s), 7.34 (2H, s), 4.01 (1H, m), 3.86 (1H, brs), 3.67 (3H, s), 3.66 (3H, s), 1.44 (18H, s), 1.42 (18H, s), 1.22 (2H, br.s), 0.94 (3H, d)

$^{13}$C-NMR (75 MHz, CDCl$_3$, TMS standard)

δ (ppm): 158.58, 158.29, 143.46, 142.94, 141.10, 139.19, 124.95, 124.84, 79.58, 64.76, 53, 42, 36.58, 36.50, 32.91, 21.75, 18.07

Production Example 7 of Optically Active Salicylideneaminoalcohol Compound

To a 50 mL round-flask were added 3.32 g of (S)-2-amino-1,1-di(4-methoxy-3,5-di-tert-butylphenyl)-1-propanol, 1.0956 g of 5-nitrosalicylaldehyde and 20.0 mL of toluene. The resulting mixture was stirred at 80° C. for 1 hour. The resulting mixture was cooled to room temperature, and then concentrated under reduced pressure. To the resulting residue were added 20.0 mL of n-heptane and 2.5 mL of ethyl acetate. The resulting mixture was heated to 80° C. The resulting solution was cooled to 20° C., and the precipitated crystal was taken out by filtration. The crystal taken out was washed with 5.0 mL of n-hexane, and dried under reduced pressure to obtain 3.25 g of a yellow crystal of (S)—N-(5-nitrosalicylidene)-2-amino-1,1-di(4-methoxy-3,5-di-tert-butylphenyl)-1-propanol.

$^1$H-NMR (300 MHz, CDCl$_3$, TMS standard)

δ (ppm): 14.46 (1H, brs), 8.11 to 8.06 (1H, m), 7.99 (1H, d), 7.79 (1H, d), 7.36 (2H, s), 7.27 (2H, d), 6.74 (1H, d), 4.42 (1H, m), 3.68 (3H, s), 3.57 (3H, s), 3.24 (1H, brs), 1.47 (3H, d), 1.42 (18H, s), 1.31 (18H, s)

$^{13}$C-NMR (75 MHz, CDCl$_3$, TMS standard)

δ (ppm): 173.98, 164.40, 159.40, 159.29, 143.82, 143.80, 138.34, 137.68, 137.52, 130.29, 129.55, 125.54, 125.41, 121.72, 115.74, 81.14, 69.75, 64.99, 64.93, 36.62, 36.55, 32.82, 32.70, 17.02

Production Example 7 of Asymmetric Copper Complex

To a 300 mL four-neck flask substituted with nitrogen were added 2.86 g of (S)—N-(5-nitrosalicylidene)-2-amino-1,1-di(4-methoxy-3,5-di-tert-butylphenyl)-1-propanol, 0.8211 g of a copper (II) acetate monohydrate and 164.2 mL of toluene. The resulting mixture was stirred at 80° C. for 1 hour. After the resulting mixture was cooled to room temperature, 1.70 mL of a methanol solution of sodium methylate (sodium methylate content: 28% by weight) was added. The resulting mixture was stirred at room temperature for 30 minutes. The resulting reaction mixture was washed with 49.2 mL of water, and then dried with anhydrous sodium sulfate. After sodium sulfate was removed by filtration, the resulting filtrate was concentrated under reduced pressure. The resulting residue was dissolved in 16.4 mL of toluene at 80° C., and 16.4 mL of n-heptane was added dropwise to the resulting solution. The resulting mixture was cooled to 20° C., and the precipitated crystal was taken out by filtration. The crystal taken out was washed with 5.0 mL of hexane, and dried under reduced pressure to obtain 2.96 g of a deep green crystal of a complex of (S)—N-(5-nitrosalicylidene)-2-amino-1,1-di(4-methoxy-3,5-di-tert-butylphenyl)-1-propanol and copper.

MS spectrum (FD-MS) m/z: 1443 (100.0%), 1444 (95.6%), 1446 (86.8%), 1445 (82.2%), 1447 (73.0%), 1442 (23.1%), 1448 (14.7%), 1441 (3.6%)

Calculated value of the molecular weight of the copper complex (binuclear complex): 1444.84

Example 8

According to the same manner as in Example 1 except that 76.0 mg of the complex of (S)—N-(5-nitrosalicylidene)-2-amino-1,1-di(4-methoxy-3,5-di-tert-butylphenyl)-1-propanol and copper obtained in Production Example 7 of asymmetric copper complex was used in place of 69.7 mg of the complex of (S)—N-(5-nitrosalicylidene)-2-amino-1,1-di(3,5-di-tert-butylphenyl)-1-propanol and copper in Example 1, a solution containing optically active ethyl 3-acetoxymethyl-2,2-dimethylcyclopropanecarboxylate was obtained.

Yield: 75.6%, cis form ratio; 80.8%, optical purity of cis form: 89.9% e.e.

Reference Example 3

To a 1000 mL round-bottom four-neck flask equipped with a Dimroth condenser with a nitrogen introducing tube attached thereto, a thermometer, a magnetic rotator and a dropping funnel were added 50.00 g of 4-hydroxy-3,5-di-tert-butylbromobenzene and 500.0 mL of dehydrated N,N-dimethylformamide. The resulting mixture was cooled to −46° C. To the mixture was added 13.74 g of 60% by weight sodium hydride at −40 to −50° C. The resulting mixture was stirred at −40±2° C. for 3 hours to allow to react. To the resulting reaction mixture was added dropwise 99.57 mL of n-butyl iodide at the same temperature, and the temperature of the resulting mixture was raised to 10° C. over 4 hours. The resulting reaction mixture was stirred at room temperature overnight, and poured into 1000 g of ice water. The resulting mixture was extracted with 400 mL of ethyl acetate three times. The resulting organic layers were mixed and dried with anhydrous magnesium sulfate. After sodium sulfate was removed by filtration, the resulting filtrate was concentrated under reduced pressure. The resulting residue was purified by silica gel column chromatography (hexane) to obtain a crude product containing 4-n-butoxy-3,5-di-tert-butylbromobenzene. The resulting crude product was heated to 130° C. under reduced pressure to obtain 40.56 g of colorless oil-like 4-n-butoxy-3,5-di-tert-butylbromobenzene.

Purity (GC): 99.9%

GC-MS m/z: 342, 340 (calculated value of the molecular weight: 341.33)

$^1$H-NMR (300 MHz, CDCl$_3$, TMS standard)

δ (ppm): 7.35 (2H, s), 3.70 (2H, t), 1.86 (2H, m), 1.45 (2H, m), 1.42 (18H, s), 0.99 (3H, t)

$^{13}$C-NMR (75 MHz, CDCl$_3$, TMS standard)

δ (ppm): 158.09, 146.68, 130.33, 116.84, 77.37, 36.71, 32.58, 32.36, 19.75, 14.86

Production Example 8 of Optically Active Aminoalcohol

A 300 mL round-bottom four-neck flask equipped with a Dimroth condenser with a nitrogen introducing tube attached thereto, a thermometer, a magnetic rotator and a dropping funnel was heated under reduced pressure, nitrogen was then introduced into the flask, pressure in the flask was returned to normal pressure, and the flask was cooled to room temperature. After 1.34 g of magnesium and a minor amount of iodine were added to the flask, a small amount of a solution obtained by mixing 20.00 g of 4-n-butoxy-3,5-di-tert-butylbromobenzene and 100.0 mL of dehydrated tetrahydrofuran was added dropwise. The flask was heated, and it was confirmed that the Grignard reaction was initiated. Thereafter, the resulting solution was added dropwise over 20 minutes. The resulting mixture was refluxed for 1.5 hours. After the resulting reaction mixture was cooled to −10° C., 1.01 g of L-alanine methyl ester hydrochloride was added. The temperature of the resulting mixture was raised to room temperature, and the mixture was further refluxed for 3 hours. The resulting reaction mixture was cooled to 0 to 5° C. To the reaction mixture were added dropwise 60.0 mL of an aqueous saturated ammonium chloride solution, and further 20.0 mL of water. The resulting mixture was stirred at 20° C. for 15 minutes, and extracted with 70.0 mL of diethyl ether three times. The resulting organic layers were mixed, and dried with anhydrous sodium sulfate. After sodium sulfate was removed by filtration, the resulting filtrate was concentrated. The resulting residue was purified by silica gel column chromatography (ethyl acetate/hexane=2/98~30/70) to obtain 2.98 g of a pale yellow solid of (S)-2-amino-1,1-di(4-n-butoxy-3,5-di-tert-butylphenyl)-1-propanol.

$^1$H-NMR (300 MHz, CDCl$_3$, TMS standard)

δ (ppm): 7.44 (2H, s), 7.30 (2H, s), 3.96 (1H, m), 3.88 (1H, brs), 3.64 (4H, m), 1.81 (4H, m), 1.42 (4H, m), 1.39 (19H, s), 1.37 (19H, s), 0.98 to 0.90 (9H, m)

$^{13}$C-NMR (75 MHz, CDCl$_3$, TMS standard)

δ (ppm): 157.15, 156.85, 143.39, 142.87, 140.79, 138.90, 125.05, 124.93, 79.61, 76.87, 76.83, 53.46, 36.62, 36.54, 32.88, 32.50, 19.80, 18.07, 14.90

Production Example 8 of Optically Active Salicylideneaminoalcohol Compound

To a 50 mL round-bottom flask were added 2.93 g of (S)-2-amino-1,1-di(4-n-butoxy-3,5-di-tert-butylphenyl)-1-propanol, 0.7539 g of 5-nitrosalicylaldehyde and 14.6 mL of toluene. The resulting mixture was stirred at 80° C. for 1 hour. The resulting reaction mixture was cooled to room temperature, and concentrated under reduced pressure. To the resulting residue were added 10.0 mL of n-heptane and 3.0 mL of ethyl acetate. The resulting mixture was heated to 80° C., and the resulting solution was cooled to 20° C. The precipitated crystal was taken out by filtration. The crystal taken out was dried under reduced pressure to obtain 2.33 g of a yellow crystal of (S)—N-(5-nitrosalicylidene)-2-amino-1,1-di(4-n-butoxy-3,5-di-tert-butylphenyl)-1-propanol.

$^1$H-NMR (300 MHz, CDCl$_3$, TMS standard)

δ (ppm): 14.51 (1H, brs), 8.11 to 8.07 (1H, m), 7.96 (1H, d), 7.71 (1H, s), 7.35 (2H, s), 7.26 (2H, s), 6.74 (1H, d), 4.38 (1H, m), 3.69 to 3.47 (4H, m), 3.19 (1H, brs), 1.88 to 1.76 (4H, m), 1.48 (3H, d), 1.41 (18H, s), 1.29 (18H, s), 1.01 to 0.93 (6H, m)

$^{13}$C-NMR (75 MHz, CDCl$_3$, TMS standard)

δ (ppm): 174.16, 164.39, 157.99, 157.88, 143.81, 143.75, 138.05, 137.60, 137.26, 130.31, 129.54, 125.57, 125.40, 121.79, 115.65, 81.17, 77.15, 69.94, 36.66, 36.59, 32.79, 32.67, 32.42, 19.78, 19.65, 16.99, 14.89

Production Example 8 of Asymmetric Copper Complex

To a 100 mL four-neck flask substituted with nitrogen were added 1.50 g of (S)—N-(5-nitrosalicylidene)-2-amino-1,1-di(4-n-butoxy-3,5-di-tert-butylphenyl)-1-propanol, 0.3826 g of a copper (II) acetate monohydrate and 76.5 mL of toluene. The resulting mixture was stirred at 80° C. for 1 hour. After the resulting mixture was cooled to room temperature, 0.79 mL of a methanol solution of sodium methylate (sodium methylate content: 28% by weight) was added. The resulting mixture was stirred at room temperature for 30 minutes. The resulting reaction mixture was washed with 23.0 mL of water, and then dried with anhydrous sodium sulfate. After sodium sulfate was removed by filtration, the resulting filtrate was concentrated under reduced pressure. The resulting residue was dissolved in 11.0 mL of toluene at 80° C., and 33.0 mL of n-heptane was added dropwise to the resulting solution. The resulting mixture was cooled to 20° C., and the precipitated crystal was taken out by filtration. The crystal taken out was washed with 5.0 mL of n-heptane, and dried under reduced pressure to obtain 0.5797 g of a deep green crystal of a complex of (S)—N-(5-nitrosalicylidene)-2-amino-1,1-di(4-n-butoxy-3,5-di-tert-butylphenyl)-1-propanol and copper.

MS spectrum (FD-MS): 1614 (100.0%), 1613 (99.8%), 1611 (91.7%), 1615 (90.0%), 1612 (75.2%), 1717 (49.5%), 1616 (44.0%), 1618 (24.8%), 1610 (11.4%), 1609 (6.1%), 1608 (3.5%), 1619 (2.8%), 1607 (1.9%)

Calculated value of the molecular weight of the copper complex (binuclear complex): 1613.16

Example 9

According to the same manner as in Example 1 except that 84.9 mg of the complex of (S)—N-(5-nitrosalicylidene)-2-amino-1,1-di(4-n-butoxy-3,5-di-tert-butylphenyl)-1-propanol and copper obtained in Production Example 8 of asymmetric copper complex was used in place of 69.7 mg of the complex of (S)—N-(5-nitrosalicylidene)-2-amino-1,1-di(3,5-di-tert-butylphenyl)-1-propanol and copper in Example 1, a solution containing optically active ethyl 3-acetoxymethyl-2,2-dimethylcyclopropanecarboxylate was obtained.

Yield: 73.1%, cis form ratio: 78.6%, optical purity of cis form: 85.2% e.e.

Example 10

To a 25 mL Schlenk tube substituted with nitrogen were added 72.8 mg of the complex of (S)—N-(5-nitrosalicylidene)-2-amino-1,1-di(3,5-di-tert-butylphenyl)-3-methyl-1-butanol and copper obtained in Production Example 2 of asymmetric copper complex, 17.1 mg of triethoxyaluminum, 3.8 mL of 1-acetoxy-3-methyl-2-butene and 11.8 μL of phenylhydrazine. The resulting mixture was adjusted at 0° C., and a solution obtained by mixing 1.14 g of ethyl diazoacetate and 1.8 mL of 1-acetoxy-3-methyl-2-butene was added dropwise over 4.6 hours. The resulting mixture was stirred at 0° C. for 30 minutes to obtain a solution containing optically active ethyl 3-acetoxymethyl-2,2-dimethylcyclopropanecarboxylate.

Yield: 72.4%, cis form ratio: 91.4%, optical purity of cis form: 96.6% e.e.

Example 11

To a 25 mL Schlenk tube substituted with nitrogen were added 72.8 mg of the complex of (S)—N-(5-nitrosalicylidene)-2-amino-1,1-di(3,5-di-tert-butylphenyl)-3-methyl-1-butanol and copper obtained in Production Example 2 of asymmetric copper complex, 29.8 mg of tetraisopropoxytitanium, 3.8 mL of 1-acetoxy-3-methyl-2-butene and 11.8 μL of phenylhydrazine. The resulting mixture was adjusted at 10° C., and a solution obtained by mixing 1.14 g of ethyl diazoacetate and 1.8 mL of 1-acetoxy-3-methyl-2-butene was added dropwise over 4.6 hours. The resulting mixture was stirred at 10° C. for 30 minutes to obtain a solution containing optically active ethyl 3-acetoxymethyl-2,2-dimethylcyclopropanecarboxylate.

Yield: 69.7%, cis form ratio: 90.9%, optical purity of cis form: 97.9% e.e.

Example 12

To a 25 mL Schlenk tube substituted with nitrogen were added 72.8 mg of the complex of (S)—N-(5-nitrosalicylidene)-2-amino-1,1-di(3,5-di-tert-butylphenyl)-3-methyl-1-butanol and copper obtained in Production Example 2 of asymmetric copper complex, 33.2 mg of tetraisopropoxyzirconium, 3.8 mL of 1-acetoxy-3-methyl-2-butene and 11.8 μL of phenylhydrazine. The resulting mixture was adjusted at 10° C., and a solution obtained by mixing 1.14 g of ethyl diazoacetate and 1.8 mL of 1-acetoxy-3-methyl-2-butene was added dropwise over 4.6 hours. The resulting mixture was stirred at 10° C. for 30 minutes to obtain a solution containing optically active ethyl 3-acetoxymethyl-2,2-dimethylcyclopropanecarboxylate.

Yield: 69.7%, cis form ratio: 91.4%, optical purity of cis form: 97.5% e.e.

Production Example 9 of Optically Active Salicylideneaminoalcohol Compound

To a 50 mL round-bottom flask were added 0.8004 g of (S)-2-amino-1,1-di(3,5-di-tert-butylphenyl)-3-methyl-1-butanol, 0.2703 g of 3-nitrosalicylaldehyde and 4.0 mL of toluene. The resulting mixture was stirred at 80° C. for 1 hour. The resulting mixture was cooled to room temperature, and then concentrated under reduced pressure to obtain 0.89 g of a yellow solid of (S)—N-(3-nitrosalicylidene)-2-amino-1,1-di (3,5-di-tert-butylphenyl)-3-methyl-1-butanol.

$^1$H-NMR (300 MHz, CDCl$_3$, TMS standard)

δ (ppm): 15.21 (1H, brs), 8.11 to 8.07 (1H, m), 7.62 (1H, s), 7.37 to 7.35 (3H, m), 7.24 to 7.10 (4H, m), 6.53 (1H, t), 3.98 (1H, d), 2.79 (1H, brs), 2.26 (1H, m), 1.33 (18H, s), 1.16 (18H, s), 1.08 (3H, d), 0.93 (3H, d)

$^{13}$C-NMR (75 MHz, CDCl$_3$, TMS standard)

δ (ppm): 165.98, 165.38, 151.40, 151.32, 144.17, 143.04, 140.72, 139.46, 133.14, 121.92, 121.02, 120.90, 120.39, 113.70, 82.76, 79.30, 35.73, 35.61, 32.24, 32.05, 29.44, 23.43, 18.97

Production Example 9 of Asymmetric Copper Complex

To a 100 mL four-neck flask substituted with nitrogen were added 0.86 g of (S)—N-(3-nitrosalicylidene)-2-amino-1,1-di (3,5-di-tert-butylphenyl)-3-methyl-1-butanol, 0.2377 g of a copper (II) acetate monohydrate and 48.0 mL of toluene. The resulting mixture was stirred at 80° C. for 1 hour. After the resulting mixture was cooled to room temperature, 0.52 mL of a methanol solution of sodium methylate (sodium methylate content: 28% by weight) was added. The resulting mixture was stirred at room temperature for 30 minutes. The resulting reaction mixture was washed with 14.3 mL of water, and then dried with anhydrous sodium sulfate. After sodium sulfate was removed by filtration, the resulting filtrate was concentrated under reduced pressure. The resulting residue was dissolved in 1.5 mL of toluene at 80° C., and 7.0 mL of n-heptane was added dropwise to the resulting solution. The resulting mixture was cooled to 20° C., and the precipitated crystal was taken out by filtration. The crystal taken out was washed with 2.0 mL of n-heptane, and dried under reduced pressure to obtain 0.7894 g of a deep green crystal of a complex of (S)—N-(3-nitrosalicylidene)-2-amino-1,1-di(3,5-di-tert-butylphenyl)-3-methyl-1-butanol and copper.

MS spectrum (FD-MS) m/z: 1381 (100.0%), 1379 (86.5%), 1382 (84.8%), 1380 (83.2%), 1383 (70.1%), 1384 (40.1%), 1385 (29.2%), 1378 (9.9%), 1386 (8.8%), 1387 (5.9%), 1388 (1.2%), 1377 (1.1%), 1376 (0.7%)

Calculated value of the molecular weight of the copper complex (binuclear complex): 1380.85

Example 13

According to the same manner as in Example 1 except that 72.7 mg of the complex of (S)—N-(3-nitrosalicylidene)-2-amino-1,1-di(3,5-di-tert-butylphenyl)-3-methyl-1-butanol and copper obtained in Production Example 9 of asymmetric copper complex was used in place of 69.7 mg of the complex of (S)—N-(5-nitrosalicylidene)-2-amino-1,1-di(3,5-di-tert-butylphenyl)-1-propanol and copper in Example 1, a solution containing optically active ethyl 3-acetoxymethyl-2,2-dimethylcyclopropanecarboxylate was obtained.

Yield: 65.1%, cis form ration: 88.6%, optical purity of cis form ratio: 93.6% e.e.

Production Example 10 of Optically Active Salicylideneaminoalcohol Compound

To a 50 mL round-bottom flask were added 0.8009 g of (S)-2-amino-1,1-di(3,5-di-tert-butylphenyl)-3-methyl-1-butanol, 0.3463 g of 3,5-dinitrosalicylaldehyde and 4.0 mL of toluene. The resulting mixture was stirred at 80° C. for 1 hour. The resulting mixture was cooled to room temperature, and then concentrated under reduced pressure. To the resulting residue were added 10.0 mL of n-heptane and 2.0 mL of ethyl acetate, and the resulting mixture was heated to 80° C. The resulting solution was cooled to 20° C., and the precipitated crystal was taken out by filtration. The crystal taken out was dried under reduced pressure to obtain 0.3766 g of a yellow crystal of (S)—N-(3,5-dinitrosalicylidene)-2-amino-1,1-di (3,5-di-tert-butylphenyl)-3-methyl-1-butanol.

$^1$H-NMR (300 MHz, CDCl$_3$, TMS standard)

δ (ppm): 14.39 (1H, brs), 8.94 (1H, d), 8.13 (1H, d), 7.70 (1H, d), 7.41 (1H, d), 7.31 (2H, d), 7.23 to 7.20 (3H, m), 4.17 (1H, d), 2.80 (1H, s), 2.35 (1H, m), 1.35 (18H, s), 1.16 (18H, s), 1.09 (3H, d), 1.02 (3H, d)

$^{13}$C-NMR (75 MHz, CDCl$_3$, TMS standard)

δ (ppm): 171.00, 166.15, 151.27, 151.10, 142.41, 141.07, 140.88, 135.96, 131.20, 128.55, 121.97, 120.22, 120.10, 116.76, 82.08, 76.80, 35.09, 34.99, 31.50, 31.32, 28.67, 22.64, 17.94

Production Example 10 of Asymmetric Copper Complex

To a 100 mL four-neck flask substituted with nitrogen were added 0.3376 g of (S)—N-(3,5-dinitrosalicylidene)-2-amino-1,1-di(3,5-di-tert-butylphenyl)-3-methyl-1-butanol, 0.0980 g of a copper (II) acetate monohydrate and 20.0 mL of toluene. The resulting mixture was stirred at 80° C. for 1 hour. After the resulting mixture was cooled to room temperature, 0.20 mL of a methanol solution of sodium methylate (sodium methylate content: 28% by weight) was added. The resulting mixture was stirred at room temperature for 30 minutes. The resulting reaction mixture was washed with 5.9 mL of water, and dried with anhydrous sodium sulfate. After sodium sulfate was removed by filtration, the resulting filtrate was concentrated under reduced pressure. The resulting residue was dissolved in 2.5 mL of toluene at 80° C., and 9.0 mL of n-heptane was added dropwise to the resulting solution. The resulting mixture was cooled to 20° C., and the precipitated crystal was taken out by filtration. The crystal taken out was washed with a mixed solution of 0.2 mL of toluene and 0.6 mL of n-heptane, and dried under reduced pressure to obtain 0.3231 g of a deep green crystal of a complex of (S)—N-(3,5-dinitrosalicylidene)-2-amino-1,1-di(3,5-di-tert-butylphenyl)-3-methyl-1-butanol and copper.

MS spectrum (FD-MS) m/z: 1471 (100.0%), 1473 (44.6%), 1470 (32.7%), 1472 (26.9%), 1474 (6.7%), 1469 (0.2%)

Calculated value of the molecular weight of the copper complex (binuclear complex): 1470.85

Example 14

According to the same manner as in Example 1 except that 77.4 mg of the complex of (S)—N-(3,5-dinitrosalicylidene)-

2-amino-1,1-di(3,5-di-tert-butylphenyl)-3-methyl-1-butanol and copper obtained in Production Example 10 of asymmetric copper complex was used in place of 69.7 mg of the complex of (S)—N-(5-nitrosalicylidene)-2-amino-1,1-di(3,5-di-tert-butylphenyl)-1-propanol and copper in Example 1, a solution containing optically active ethyl 3-acetoxymethyl-2,2-dimethylcyclopropanecarboxylate was obtained.

Yield: 63.1%, cis form ratio: 87.2%, optical purity of cis form: 93.6% e.e.

Production Example 11 of Optically Active Salicylideneaminoalcohol Compound

To a 50 mL round-bottom flask were added 0.8007 g of (S)-2-amino-1,1-di(3,5-di-tert-butylphenyl)-3-methyl-1-butanol, 0.4104 g of 3-bromo-5-nitrosalicylaldehyde and 4.0 mL of toluene. The resulting mixture was stirred at 80° C. for 1 hour. The resulting mixture was cooled to room temperature, and then concentrated under reduced pressure. To the resulting residue were added 6.0 mL of n-heptane and 2.5 mL of ethyl acetate. The resulting mixture was heated to 80° C. The resulting solution was cooled to 20° C., and the precipitated crystal was taken out by filtration. The crystal taken out was dried under reduced pressure to obtain 0.5330 g of a yellow crystal of (S)—N-(3-bromo-5-nitrosalicylidene)-2-amino-1,1-di(3,5-di-tert-butylphenyl)-3-methyl-1-butanol.

$^1$H-NMR (300 MHz, CDCl$_3$, TMS standard)

δ (ppm): 14.58 (1H, brs), 8.50 (1H, d), 7.92 (1H, d), 7.57 (1H, d), 7.40 (1H, d), 7.33 to 7.20 (5H, m), 4.08 (1H, d), 2.81 (1H, s), 2.31 (1H, m), 1.35 (18H, s), 1.15 (18H, s), 1.10 (3H, d), 0.99 (3H, d)

$^{13}$C-NMR (75 MHz, CDCl$_3$, TMS standard)

δ (ppm): 174.52, 165.82, 151.03, 150.89, 142.73, 141.53, 134.27, 132.16, 130.86, 121.70, 121.69, 120.34, 120.17, 119.07, 111.74, 82.13, 76.52, 35.07, 34.95, 31.53, 31.33, 28.68, 22.66, 17.91

Production Example 11 of Asymmetric Copper Complex

To a 100 mL four-neck flask substituted with nitrogen were added 0.4880 g of (S)—N-(3-bromo-5-nitrosalicylidene)-2-amino-1,1-di(3,5-di-tert-butylphenyl)-3-methyl-1-butanol, 0.1349 g of a copper (II) acetate monohydrate and 27.0 mL of toluene. The resulting mixture was stirred at 80° C. for 1 hour. After the resulting mixture was cooled to room temperature, 10 mL of a 5% by weight aqueous sodium bicarbonate solution was added. The resulting mixture was stirred at room temperature for 30 minutes. The resulting mixture was washed with 8.1 mL of water, and then dried with anhydrous sodium sulfate. After sodium sulfate was removed by filtration, the resulting filtrate was concentrated under reduced pressure. The resulting residue was dissolved in 4.0 mL of toluene at 80° C., and 7.0 mL of n-heptane was added dropwise to the resulting solution. The resulting mixture was cooled to 20° C., and the precipitated crystal was taken out by filtration. The crystal taken out was washed with a mixed solution of 0.3 mL of toluene and 0.8 mL of n-heptane, and dried under reduced pressure to obtain 0.4798 g of a deep green crystal of a complex of (S)—N-(3-bromo-5-nitrosalicylidene)-2-amino-1,1-di(3,5-di-tert-butylphenyl)-3-methyl-1-butanol and copper.

MS spectrum (FD-MS) m/z: 1538 (100.0%), 1540 (94.9%), 1539 (91.8%), 1542 (73.8%), 1541 (68.5%), 1536 (64.1%), 1537 (54.1%), 1543 (24.9%), 1535 (16.6%), 1544 (7.9%)

Calculated value of the molecular weight of the copper complex (binuclear complex): 1538.63

Example 15

According to the same manner as in Example 1 except that 81.0 mg of the complex of (S)—N-(3-bromo-5-nitrosalicylidene)-2-amino-1,1-di(3,5-di-tert-butylphenyl)-3-methyl-1-butanol and copper obtained in Production Example 11 of asymmetric copper complex was used in place of 69.7 mg of the complex of (S)—N-(5-nitrosalicylidene)-2-amino-1,1-di(3,5-di-tert-butylphenyl)-1-propanol and copper in Example 1, a solution containing optically active ethyl 3-acetoxymethyl-2,2-dimethylcyclopropanecarboxylate was obtained.

Yield: 71.0%, cis form ratio: 86.8%, optical purity of cis form: 94.2% e.e.

Production Example 12 of Optically Active Salicylideneaminoalcohol Compound

To a 50 mL round-bottom flask were added 0.9004 g of (S)-2-amino-1,1-di(3,5-di-tert-butylphenyl)-3-methyl-1-butanol, 0.2550 g of 3-fluorosalicylaldehyde and 4.5 mL of toluene. The resulting mixture was stirred at 80° C. for 1 hour. The resulting mixture was cooled to room temperature, and then concentrated under reduced pressure to obtain 0.93 g of a yellow solid of (S)—N-(3-fluorosalicylidene)-2-amino-1,1-di(3,5-di-tert-butylphenyl)-3-methyl-1-butanol.

$^1$H-NMR (300 MHz, CDCl$_3$, TMS standard)

δ (ppm): 13.94 (1H, brs), 7.84 (1H, d), 7.42 (2H, d), 7.30 to 7.02 (5H, m), 6.75 (1H, d), 6.66 to 6.59 (1H, m), 3.89 (1H, d), 2.66 (1H, s), 2.21 (1H, m), 1.32 (18H, s), 1.19 (18H, s), 1.02 (3H, d), 0.86 (3H, d)

$^{13}$C-NMR (75 MHz, CDCl$_3$, TMS standard)

δ (ppm): 166.36, 166.32, 154.18, 152.92, 152.74, 150.94, 150.92, 145.13, 143.81, 127.00, 126.95, 121.36, 121.28, 121.11, 120.58, 120.52, 119.31, 119.08, 117.56, 117.47, 82.66, 82.11, 35.69, 35.58, 32.26, 32.12, 29.58, 23.45, 19.10

Production Example 12 of Asymmetric Copper Complex

To a 100 mL four-neck flask substituted with nitrogen were added 0.89 g of (S)—N-(3-fluorosalicylidene)-2-amino-1,1-di(3,5-di-tert-butylphenyl)-3-methyl-1-butanol, 0.2601 g of a copper (II) acetate monohydrate and 52.0 mL of toluene. The resulting mixture was stirred at 80° C. for 1 hour. After the resulting mixture was cooled to room temperature, 0.57 mL of a methanol solution of sodium methylate (sodium methylate content; 28% by weight) was added. The resulting mixture was stirred at room temperature for 30 minutes. The resulting reaction mixture was washed with 16.0 mL of water, and then dried with anhydrous sodium sulfate. After sodium sulfate was removed by filtration, the resulting filtrate was concentrated under reduced pressure to obtain 0.9709 g of a deep green solid of a complex of (S)—N-(3-fluorosalicylidene)-2-amino-1,1-di(3,5-di-tert-butylphenyl)-3-methyl-1-butanol and copper.

MS spectrum (FD-MS) m/z: 1327 (100.0%), 1326 (89.6%), 1328 (84.8%), 1325 (81.1%), 1329 (70.6%), 1324 (56.5%), 1330 (45.4%), 1331 (27.8%), 1332 (14.3%), 1333 (4.2%), 1323 (3.6%), 1322 (1.9%), 1334 (1.5%), 1335 (1.2%), 1337 (0.9%)

Calculated value of the molecular weight of the copper complex (binuclear complex): 1326.83

Example 16

According to the same manner as in Example 1 except that 69.8 mg of the complex of (S)—N-(3-fluorosalicylidene)-2-amino-1,1-di(3,5-di-tert-butylphenyl)-3-methyl-1-butanol and copper obtained in Example 12 of asymmetric copper complex was used in place of 69.7 mg of the complex of (S)—N-(5-nitrosalicylidene)-2-amino-1,1-di(3,5-di-tert-butylphenyl)-1-propanol and copper in Example 1, a solution containing optically active ethyl 3-acetoxymethyl-2,2-dimethylcyclopropanecarboxylate was obtained.

Yield: 16.6%, cis form ratio: 82.9%, optically purity of cis form: 82.8% e.e.

Production Example 13 of Optically Active Salicylideneaminoalcohol Compound

To a 50 mL round-bottom flask were added 0.9005 g of (S)-2-amino-1,1-di(3,5-di-tert-butylphenyl)-3-methyl-1-butanol, 0.2906 g of 3,5-difluorosalicylaldehyde and 4.5 mL of toluene. The resulting mixture was stirred at 80° C. for 1 hour. The resulting mixture was cooled to room temperature, and then concentrated under reduced pressure. To the resulting residue was added 2.0 mL of n-heptane, followed by heating to 80° C. The resulting solution was cooled to 20° C., and the precipitated crystal was taken out by filtration. The crystal taken out was dried under reduced pressure to obtain 0.5560 g of a yellow crystal of (S)—N-(3,5-difluorosalicylidene)-2-amino-1,1-di(3,5-di-tert-butylphenyl)-3-methyl-1-butanol.

$^1$H-NMR (300 MHz, CDCl$_3$, TMS standard)
δ (ppm): 13.70 (1H, brs), 7.78 (1H, s), 7.40 (2H, d), 7.30 to 7.15 (4H, m), 6.91 to 6.84 (1H, m), 6.52 to 6.48 (1H, m), 3.88 (1H, d), 2.60 (1H, s), 2.23 (1H, m), 1.32 (18H, s), 1.20 (18H, s), 0.99 (3H, d), 0.86 (3H, d)

$^{13}$C-NMR (75 MHz, CDCl$_3$, TMS standard)
δ (ppm): 165.27, 150.99, 148.91, 148.70, 144.96, 143.75, 121.46, 121.34, 121.15, 121.01, 111.75, 111.46, 108.56, 108.20, 107.91, 82.71, 82.56, 35.70, 35.59, 32.25, 32.12, 29.63, 23.45, 19.16

Production Example 13 of Asymmetric Copper Complex

To a 100 mL four-neck flask substituted with nitrogen were added 0.5140 g of (S)—N-(3,5-difluorosalicylidene)-2-amino-1,1-di(3,5-di-tert-butylphenyl)-3-methyl-1-butanol, 0.1622 g of a copper (II) acetate monohydrate and 32.4 mL of toluene. The resulting mixture was stirred at 80° C. for 1 hour. After the resulting mixture was cooled to room temperature, 10 mL of a 5% by weight aqueous sodium bicarbonate solution was added. The resulting mixture was stirred at room temperature for 30 minutes. The resulting mixture was washed with 9.7 mL of water, and then dried with anhydrous sodium sulfate. After sodium sulfate was removed by filtration, the resulting filtrate was concentrated under reduced pressure to obtain 0.5768 g of a deep green solid of a complex of (S)—N-(3,5-difluorosalicylidene)-2-amino-1,1-di(3,5-di-tert-butylphenyl)-3-methyl-1-butanol and copper.

MS spectrum (FD-MS) m/z: 1363 (100.0%), 1361 (81.0%), 1364 (79.1%), 1362 (75.9%), 1365 (65.0%), 1366 (43.9%), 1367 (25.9%), 1368 (11.0%), 1360 (2.48%), 1369 (2.1%), 1370 (1.2%), 1359 (1.04%), 1371 (0.1%)

Calculated value of the molecular weight of the copper complex (binuclear complex): 1362.81

Example 17

According to the same manner as in Example 1 except that 71.7 mg of the complex of (S)—N-(3,5-difluorosalicylidene)-2-amino-1,1-di(3,5-di-tert-butylphenyl)-3-methyl-1-butanol and copper obtained in Production Example 13 of asymmetric copper complex was used in place of 69.7 mg of the complex of (S)—N-(5-nitrosalicylidene)-2-amino-1,1-di(3,5-di-tert-butylphenyl)-1-propanol and copper in Example 1, a solution containing optically active ethyl 3-acetoxymethyl-2,2-dimethylcyclopropanecarboxylate was obtained.

Yield: 28.8%, cis form ratio: 88.0%, optical purity of cis form: 93.0% e.e.

Production Example 14 of Optically Active Salicylideneaminoalcohol Compound

To a 50 mL round-bottom flask were added 0.8005 g of (S)-2-amino-1,1-di(3,5-di-tert-butylphenyl)-3-methyl-1-butanol, 0.2944 g of 5-(methoxycarbonyl)salicylaldehyde and 4.0 mL of toluene. The resulting mixture was stirred at 80° C. for 1 hour. The resulting reaction mixture was cooled to room temperature, and then concentrated under reduced pressure to obtain 0.9754 g of a yellow solid of (S)—N-[5-(methoxycarbonyl)salicylidene]-2-amino-1,1-di(3,5-di-tert-butylphenyl)-3-methyl-1-butanol.

$^1$H-NMR (300 MHz, CDCl$_3$, TMS standard)
δ (ppm): 14.29 (1H, brs), 7.93 to 7.87 (2H, m), 7.76 (1H, d), 7.40 (2H, d), 7.31 to 7.14 (4H, m), 6.88 (1H, d), 3.87 (1H, d), 3.86 (3H, s), 2.72 (1H, s), 2.23 (1H, m), 1.32 (18H, s), 1.20 (18H, s), 0.98 (3H, d), 0.87 (3H, d)

$^{13}$C-NMR (75 MHz, CDCl$_3$, TMS standard)
δ (ppm): 168.39, 167.17, 166.22, 150.97, 150.93, 144.89, 143.81, 134.92, 134.66, 121.46, 121.39, 121.22, 120.13, 120.21, 118.89, 118.68, 118.12, 82.70, 82.12, 52.57, 35.69, 35, 58, 32.25, 32.12, 29.68, 23.39, 19.13

Production Example 14 of Asymmetric Copper Complex

To a 100 mL four-neck flask substituted with nitrogen were added 0.9320 g of (S)—N-[5-(methoxycarbonyl)salicylidene]-2-amino-1,1-di(3,5-di-tert-butylphenyl)-3-methyl-1-butanol, 0.2698 g of a copper (II) acetate monohydrate and 54.0 mL of toluene. The resulting mixture was stirred at 80° C. for 1 hour. After the resulting reaction mixture was cooled to room temperature, 10 mL of a 5% by weight aqueous sodium bicarbonate solution was added. The resulting mixture was stirred at room temperature for 30 minutes. The resulting mixture was washed with 16.2 mL of water, and then dried with anhydrous sodium sulfate. After sodium sulfate was removed by filtration, the resulting filtrate was concentrated under reduced pressure. The resulting residue was dissolved in 1.5 mL of toluene at 80° C., and 7.0 mL of n-heptane was added dropwise to the resulting solution. The resulting mixture was cooled to 20° C., and the precipitated crystal was taken out by filtration. The crystal taken out was washed with a mixed solution of 0.5 mL of toluene and 2.0 mL of n-heptane, and concentrated under reduced pressure to obtain 0.8862 g of a deep green crystal of a complex of (S)—N-[5-(methoxycarbonyl)salicylidene]-2-amino-1,1-di(3,5-di-tert-butylphenyl)-3-methyl-1-butanol and copper.

MS spectrum (FD-MS) m/z: 1407 (100.0%), 1405 (72.0%), 1408 (62.1%), 1406 (60.9%), 1409 (55.8%), 1410 (41.8%), 1411 (25.4%), 1412 (12.3%), 1413 (2.8%)

Calculated value of the molecular weight of the copper complex (binuclear complex): 1406.93

Example 18

According to the same manner as in Example 1 except that 69.8 mg of the complex of (S)—N-[5-(methoxycarbonyl)

salicylidene]-2-amino-1,1-di-(3,5-di-tert-butylphenyl)-3-methyl-1-butanol and copper obtained in Production Example 14 of asymmetric copper complex was used in place of 69.7 mg of the complex of (S)—N-(5-nitrosalicylidene)-2-amino-1,1-di(3,5-di-tert-butylphenyl)-1-propanal and copper in Example 1, a solution containing optically active ethyl 3-acetoxymethyl-2,2-dimethylcyclopropanecarboxylate was obtained.

Yield: 20.1%, cis form ratio: 80.8%, optical purity of cis form: 83.8% e.e.

Example 19

To a 50 mL Schlenk tube substituted with nitrogen were added 74.8 mg of the complex of (2S,3S)—N-(5-nitrosalicylidene)-2-amino-1,1-di(3,5-di-tert-butylphenyl)-3-methyl-1-pentanol and copper obtained in Production Example 6 of asymmetric copper complex, 3.9 mg of lithium methoxide, 3.8 mL of 1-acetoxy-3-methyl-2-butene, 11.2 mL of ethyl acetate and 11.8 μL of phenylhydrazine. The resulting mixture was adjusted at 10° C., and a solution obtained by mixing 1.14 g of ethyl diazoacetate and 1.8 mL of 1-acetoxy-3-methyl-2-butene was added dropwise over 4.6 hours. The resulting mixture was stirred at 10° C. for 30 minutes to obtain a solution containing optically active ethyl 3-acetoxymethyl-2,2-dimethylcyclopropanecarboxylate.

Yield: 67.3%, cis form ratio=94.8%, optically purity of cis form: 98.5% e.e.

Example 20

To a 50 mL Schlenk tube substituted with nitrogen were added 72.8 mg of the complex of (S)—N-(5-nitrosalicylidene)-2-amino-1,1-di(3,5-di-tert-butylphenyl)-3-methyl-1-butanol and copper obtained in Production Example 2 of asymmetric copper complex, 3.8 mL of 1-acetoxy-3-methyl-2-butene, 11.2 mL of ethyl acetate and 11.8 μL of phenylhydrazine. After the resulting mixture was adjusted at 10° C., a solution obtained by mixing 1.14 g of ethyl diazoacetate and 1.8 mL of 1-acetoxy-3-methyl-2-butene was added dropwise over 4.6 hours. The resulting mixture was stirred at 10° C. for 30 minutes to obtain a solution containing optically active ethyl 3-acetoxymethyl-2,2-dimethylcyclopropanecarboxylate.

Yield: 71.3%, cis form ratio: 94.7%, optical purity of cis form: 98.8% e.e.

Example 21

To a 50 mL Schlenk tube substituted with nitrogen were added 72.8 mg of the complex of (S)—N-(5-nitrosalicylidene)-2-amino-1,1-di(3,5-di-tert-butylphenyl)-3-methyl-1-butanol and copper obtained in Production Example 2 of asymmetric copper complex, 8.0 mL of 1-acetoxy-3-methyl-2-butene and 11.8 μL of phenylhydrazine. After the resulting mixture was adjusted at 10° C., a solution obtained by mixing 1.14 g of ethyl diazoacetate and 1.8 mL of 1-acetoxy-3-methyl-2-butene was added dropwise over 4.6 hours. The resulting mixture was stirred at 10° C. for 30 minutes to obtain a solution containing optically active ethyl 3-acetoxymethyl-2,2-dimethylcyclopropanecarboxylate.

Yield: 80.3%, cis form ratio: 90.2%, optical purity of cis form: 97.2% e.e.

Example 22

To a 25 mL Schlenk tube substituted with nitrogen were added 72.8 mg of the complex of (S)—N-(5-nitrosalicylidene)-2-amino-1,1-di(3,5-di-tert-butylphenyl)-3-methyl-1-butanol and copper obtained in Production Example 2 of asymmetric copper complex, 4.0 mg of lithium methoxide, 3.8 mL of 1-acetoxy-3-methyl-2-butene and 11.8 μL of phenylhydrazine. After the resulting mixture was adjusted at 10° C., a solution obtained by mixing 1.14 g of ethyl diazoacetate and 1.8 mL of 1-acetoxy-3-methyl-2-butene was added dropwise over 4.6 hours. The resulting mixture was stirred at 10° C. for 30 minutes to obtain a solution containing optically active ethyl 3-acetoxymethyl-2,2-dimethylcyclopropanecarboxylate.

Yield: 72.5%, cis form ratio: 90.4%, optical purity of cis form: 97.2% e.e.

Example 23

To a 25 mL Schlenk tube substituted with nitrogen were added 72.8 mg of the complex of (S)—N-(5-nitrosalicylidene)-2-amino-1,1-di(3,5-di-tert-butylphenyl)-3-methyl-1-butanol and copper obtained in Production Example 2 of asymmetric copper complex, 15.1 mg of triethoxyborane, 3.8 mL of 1-acetoxy-3-methyl-2-butene and 11.8 μL of phenylhydrazine. After the resulting mixture was adjusted at 10° C., a solution obtained by mixing 1.14 g of ethyl diazoacetate and 1.8 mL of 1-acetoxy-3-methyl-2-butene was added dropwise over 4.6 hours. The resulting mixture was stirred at 10° C. for 30 minutes to obtain a solution containing optically active ethyl 3-acetoxymethyl-2,2-dimethylcyclopropanecarboxylate.

Yield: 71.1%, cis form ratio: 90.5%, optical purity of cis form: 97.5% e.e.

Example 24

To a 50 mL Schlenk tube substituted with nitrogen were added 94.5 mg of the complex of (S)—N-(5-nitrosalicylidene)-2-amino-1,1-di(3,5-di-tert-butylphenyl)-3-methyl-1-butanol and copper obtained in Production Example 2 of asymmetric copper complex, 20.8 mL of 1-acetoxy-3-methyl-2-butene and 15.3 μL of phenylhydrazine. After the resulting mixture was adjusted at 10° C., a solution obtained by mixing 2.97 g of ethyl diazoacetate and 4.8 mL of 1-acetoxy-3-methyl-2-butene was added dropwise over 12.6 hours. The resulting mixture was stirred at 10° C. for 30 minutes to obtain a solution containing optically active ethyl 3-acetoxymethyl-2,2-dimethylcyclopropanecarboxylate.

Yield: 89.7%, cis form ratio: 93.5%, optical purity of cis form: 98.1% e.e.

INDUSTRIAL APPLICABILITY

Since according to the present invention, an optically active cyclopropanecarboxylic acid ester compound can be produced at a good cis form ratio and a good optical purity, this is industrially advantageous.

The invention claimed is:

1. A process for producing an optically active cyclopropanecarboxylic acid ester compound represented by the formula (4):

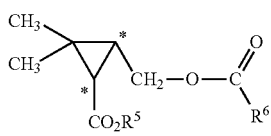
(4)

(wherein $R^5$, $R^6$ and * each represents the same meaning as defined below), comprising reacting a diazoacetic acid ester represented by the formula (2):

(2)

(wherein $R^5$ represents an alkyl group having 1 to 15 carbon atoms or an aryl group having 6 to 10 carbon atoms) with a compound represented by the formula (3):

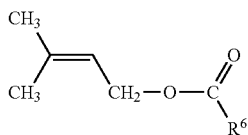
(3)

(wherein $R^6$ represents an alkyl group having 1 to 15 carbon atoms, an aryl group having 6 to 10 carbon atoms or an aralkyl group having 7 to 20 carbon atoms), in the presence of an asymmetric copper complex obtained by reacting a copper compound and an optically active salicylideneaminoalcohol compound represented by the formula (1):

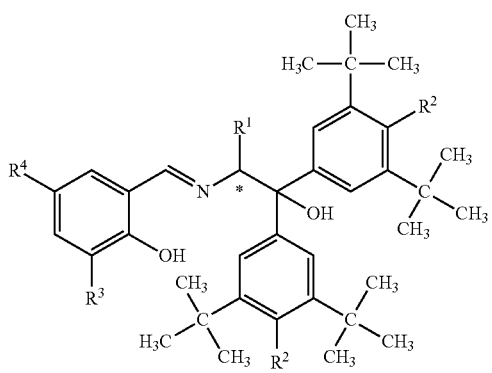
(1)

(wherein $R^1$ represents an alkyl group having 2 to 4 carbon atoms, an aryl group having 6 to 10 carbon atoms or an aralkyl group having 7 to 20 carbon atoms, $R^2$ represents a hydrogen atom, an alkyl group having 1 to 4 carbon atoms or an alkoxy group having 1 to 10 carbon atoms, $R^3$ represents a hydrogen atom, a nitro group or a bromine atom, $R^4$ represents a hydrogen atom or a nitro group, and * represents an asymmetric center);

wherein the optically active cyclopropanecarboxylic acid ester compound has a cis form ratio (ratio (%) of a cis form relative to a total of a cis form and a trans form) of 85% or more.

2. The production process according to claim 1, wherein the copper compound is a divalent copper compound.

3. The production process according to claim 1, wherein the copper compound is copper acetate.

4. The production process according to claim 1, wherein $R^4$ is a nitro group.

5. The production process according to claim 1, wherein $R^2$ is a hydrogen atom.

6. The production process according to claim 1, wherein $R^5$ is an ethyl group, and $R^6$ is a methyl group.

7. The production process according to claim 1, wherein the reaction of the diazoacetic acid ester represented by the formula (2) with the compound represented by the formula (3) is performed in the presence of a Lewis acid.

8. The production process according to claim 7, wherein the Lewis acid is a metal alkoxide having Lewis acidity.

9. The production process according to claim 1, wherein the reaction of the diazoacetic acid ester represented by the formula (2) with the compound represented by the formula (3) is performed in the presence of a lithium compound.

10. The production process according to claim 9, wherein the lithium compound is a lithium alkoxide having 1 to 4 carbon atoms.

11. The production process according to claim 1, wherein $R^1$ is —CH(CH$_3$)$_2$, —CH$_2$CH$_3$, —CH$_2$CH(CH$_3$)$_2$, a benzyl group, or —CH(CH$_3$)CH$_2$CH$_3$.

* * * * *